US012774296B2

(12) United States Patent
Liao et al.

(10) Patent No.: US 12,774,296 B2
(45) Date of Patent: Oct. 27, 2026

(54) SUBSTITUTED PYRIDIN-2-AMINES AS TLR8 AGONISTS

(71) Applicants: TSINGHUA UNIVERSITY, Beijing (CN); BEIJING SYNTHETIC VACCINE BIOSCIENCES CO., LTD, Beijing (CN)

(72) Inventors: Xuebin Liao, Beijing (CN); Zhisong Wang, Beijing (CN); Yan Zhang, Beijing (CN)

(73) Assignees: TSINGHUA UNIVERSITY, Beijing (CN); BEIJING SYNTHETIC VACCINE BIOSCIENCES CO., LTD, Beijing (CN)

( * ) Notice: Subject to any disclaimer, the term of this patent is extended or adjusted under 35 U.S.C. 154(b) by 527 days.

(21) Appl. No.: 18/259,762

(22) PCT Filed: Dec. 31, 2021

(86) PCT No.: PCT/CN2021/143703
§ 371 (c)(1),
(2) Date: Jun. 28, 2023

(87) PCT Pub. No.: WO2022/143985
PCT Pub. Date: Jul. 7, 2022

(65) Prior Publication Data

US 2024/0116962 A1 Apr. 11, 2024

(30) Foreign Application Priority Data

Dec. 31, 2020 (CN) ......................... 202011644306.2

(51) Int. Cl.

| | |
|---|---|
| ***C07D 213/02*** | (2006.01) |
| ***A61K 45/06*** | (2006.01) |
| ***C07D 213/73*** | (2006.01) |
| ***C07D 401/10*** | (2006.01) |
| ***C07D 413/10*** | (2006.01) |
| ***C07D 471/04*** | (2006.01) |
| ***C07D 491/107*** | (2006.01) |
| ***C07F 9/58*** | (2006.01) |

(52) U.S. Cl.
CPC ................ *C07F 9/58* (2013.01); *A61K 45/06* (2013.01); *C07D 213/73* (2013.01); *C07D 401/10* (2013.01); *C07D 413/10* (2013.01); *C07D 471/04* (2013.01); *C07D 491/107* (2013.01)

(58) Field of Classification Search
CPC .............................. A61K 31/44; C07D 213/02
USPC ........................................... 514/352; 546/311
See application file for complete search history.

(56) References Cited

U.S. PATENT DOCUMENTS

2006/0128669 A1 6/2006 Murai et al.

FOREIGN PATENT DOCUMENTS

| | | | | |
|---|---|---|---|---|
| CN | 101516369 A | 8/2009 | | |
| CN | 102026970 A | 4/2011 | | |
| CN | 102834380 A | 12/2012 | | |
| CN | 109438343 A | 3/2019 | | |
| CN | 109776335 A | 5/2019 | | |
| EP | 4253383 A1 | * | 10/2023 | ........... C07D 471/04 |
| WO | 2009049421 A1 | 4/2009 | | |
| WO | 2010088177 A1 | 8/2010 | | |
| WO | 2020198026 A1 | 10/2020 | | |
| WO | 2021071821 A1 | 4/2021 | | |
| WO | 2021178488 A1 | 9/2021 | | |

OTHER PUBLICATIONS

Jordan, V. C. Nature Reviews: Drug Discovery, 2, 2003, 205. (Year: 2003).*
Dörwald, F. Zaragoza. Side Reactions in Organic Synthesis: A Guide to Successful Synthesis Design, Weinheim: WILEY-VCH Verlag Gmbh & Co. KGaA, 2005, Preface. (Year: 2005).*
Vippagunta, et al. Advanced Drug Delivery Reviews, 48, 2001, 18. (Year: 2001).*
Wolff, Manfred E., Ed. Burger's Medicinal Chemistry and Drug Discovery—Fifth Edition, vol. 1: Principles and Practice, New York: John Wiley & Sons, 1994, 975-977. (Year: 1994).*
CAS Registry Database, RN: 1413281-42-1, entered STN: Dec. 10, 2012, accessed by Examiner D. M. Willis on Feb. 9, 2026.*
Z. Cai et al., "Copper-Catalyzed Cyclization of Oxime Acetates with 2-Benzylidenemalononitriles for Synthesis of 2-Aminonicotinonitriles", Acta Chimica Sinica, vol. 72, No. 8, Aug. 15, 2014, pp. 914-919. (English abstract provided.).
International Search Report w/English translation for PCT/CN2021/143703 mailed Apr. 6, 2022, 8 pages.
Written Opinion of the ISA for PCT/CN2021/143703 mailed Apr. 6, 2022, 6 pages.

* cited by examiner

*Primary Examiner* — Douglas M Willis
(74) *Attorney, Agent, or Firm* — NIXON & VANDERHYE, PC

(57) ABSTRACT

Disclosed in the present invention are a pyridine-2-amine derivative of Formula (I) and a pharmaceutical composition and use thereof. The pyridine-2-amine derivative can be used as a TLR8 selective agonist, has the characteristics of high selectivity, strong activity and high safety, can be used for preventing and/or treating diseases related to TLR activity, for example, diseases caused by or related to pathogen infection, immunological diseases, inflammation, and tumors, can also be used for preparing a vaccine adjuvant to enhance immune response, and has better application prospects and research and development value.

(I)

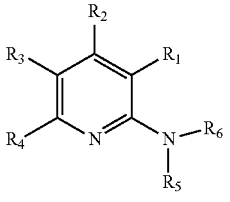

18 Claims, No Drawings

SUBSTITUTED PYRIDIN-2-AMINES AS TLR8 AGONISTS

CROSS-REFERENCE TO RELATED APPLICATIONS

This application is the U.S. national phase of International Application No. PCT/CN2021/143703 filed Dec. 31, 2021, which designated the U.S. and claims priority to CN 202011644306.2 filed Dec. 31, 2020, the entire contents of each of which are hereby incorporated by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

Field of the Invention

The present invention relates to the technical field of pharmaceuticals, and particularly to a pyridin-2-amine derivative that can be used as a TLR8 selective agonist, a pharmaceutical composition and use thereof.

Description of Related Art

Toll-like receptors (TLR1, 2, and 3-13) are a very important class of receptors that specifically recognize pathogen-associated molecular patterns (PAMPs). These receptors are widely expressed on immune cells and epithelial cells. Among them, TLR1, TLR2, TLR4, TLR5, TLR6, and TLR10 are expressed on the cell surface to rapidly recognize bacterial metabolites. TLR3, TLR7, TLR8, and TLR9 are expressed in endosomes mainly for monitoring and recognizing viral nucleic acids. TLR3 recognizes double-stranded RNA, TLR7 and TLR8 mainly recognize viral single-stranded RNA in cytoplasm, and TLR9 recognizes unmethylated CG coenzyme I (CPG), thereby modulating responses of bacterial DNA and certain viruses.

TLRs can specifically recognize pathogen-associated molecular patterns (PAMPs), play an important role in both innate immunity and adaptive immunity, and are bridges connecting the innate immunity and the adaptive immunity. Among them, TLR8 can recruit specific adaptor protein MyD88 after recognizing viral single-stranded RNA or artificially synthesized purine-like small molecule compounds, activate a series of signaling cascade reactions, initiate innate immune responses, and induce high-level systemic adaptive immune responses to kill cells infected with viruses, thereby completely eliminating the viruses. In clinical experiments, TLR8 agonists have been used for treating chronic viral infectious diseases, such as hepatitis B and hepatitis C. In the vast majority of individuals infected with HIV-1, the viral reservoir in $CD4^+$ T lymphocytes with latent infection is responsible for the viral rebound, thus hindering effect of the antiviral therapy (ART) and presenting a significant challenge to curing AIDS. Various strategies for HIV-1 therapy are currently in progress. One hypothesis is that activating the viral reservoirs may make them more susceptible to immune-mediated killing. Activation of TLR8 is an important means for efficient activation of latent viral reservoirs. TLR8 expressed by activated myeloid dendritic cells can induce the secretion of TNF-α to activate the HIV viral reservoir in adjacent $CD4^+$ T cells with latent infection in a paracrine manner, whereas the $CD4^+$ T cells themselves do not express TLR8.

At present, TLR7 agonists have made a very important progress in the field of HIV treatment, and the therapeutic prospect of TLR8 agonists is to be researched, which may be limited by the limited number of high-selectivity TLR8 agonists currently available. As reported in the existing studies, the activation of TLR8 appears to be more important in replication and transcription of HIV viruses than TLR7. The activation of TLR8 can activate not only the latent viral reservoir in DC cells, but also latent viral reservoir in adjacent $CD4^+$ T cells. In order to study the effect of TLR8 activation in silencing HIV viruses in the viral reservoir in $HIV^+$ patients subjected to highly potent antiretroviral therapy and the effect of TLR8 agonists in AIDS therapy, it is important to design and synthesize highly selective and potent TLR8 agonists.

BRIEF SUMMARY OF THE INVENTION

The present invention provides a pyridin-2-amine derivative or a salt thereof, which can be used as a TLR8 selective agonist and has characteristics of high selectivity, strong activity and good safety. Specifically, the pyridin-2-amine derivative described above has the following structure:

(I)

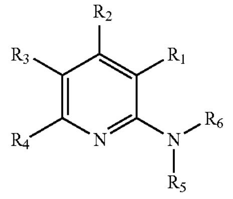

wherein, $R_1$-$R_4$ are independently selected from: hydrogen, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted aralkyl, substituted or unsubstituted heterocyclyl, substituted or unsubstituted heterocyclylalkyl, $—COR_7$, $—C(O)OR_7$, $—C(O)NR_7R_8$, $—CH{=}NR_7$, $—CN$, $—OR_7$, $—OC(O)R_7$, $—S(O)_t—R_7$, $—NR_7R_8$, $—NR_7C(O)R_8$, $—NO_2$, $—N{=}CR_7R_8$, and halogen;

or any two of $R_1$-$R_4$ (e.g., $R_1$ and $R_2$, $R_2$ and $R_3$, or $R_3$ and $R_4$), together with the carbon atoms attached thereto, form substituted or unsubstituted aryl or heterocyclyl;

$R_5$ and $R_6$ are independently selected from: hydrogen, substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted aralkyl, substituted or unsubstituted heterocyclyl, substituted or unsubstituted heterocyclylalkyl, $-COR_7$, $-C(O)OR_7$, and $-C(O)NR_7R_8$;

or $R_5$ and $R_6$, together with the nitrogen atom attached thereto, form substituted or unsubstituted heterocyclyl; t is selected from 0, 1, and 2;

$R_7$ and $R_8$ are independently selected from: hydrogen, substituted or unsubstituted alkyl, substituted or unsubstituted cycloalkyl, substituted or unsubstituted alkenyl, substituted or unsubstituted aryl, substituted or unsubstituted heterocyclyl, and halogen.

In one embodiment of the present invention, $R_3$ and $R_4$, together with the carbon atoms attached thereto, form substituted or unsubstituted aryl or heterocyclyl; for example, the pyridin-2-amine derivative described above may have a structure shown below:

(II)

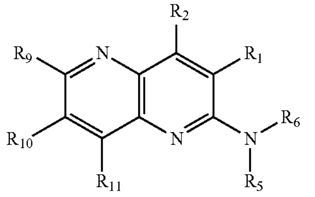

wherein, $R_9$-$R_{11}$ are independently selected from: substituted or unsubstituted alkyl, substituted or unsubstituted cycloalkyl, substituted or unsubstituted cycloalkylalkyl, substituted or unsubstituted alkenyl, substituted or unsubstituted aryl, substituted or unsubstituted aralkyl, substituted or unsubstituted heterocyclyl, substituted or unsubstituted heterocyclylalkyl, $-COR_7$, $-C(O)OR_7$, $-C(O)NR_7R_8$, $-CH{=}NR_7$, $-CN$, $-OR_7$, $-OC(O)R_7$, $-S(O)_t-R_7$, $-NR_7R_8$, $-NR_7C(O)R_8$, $-NO_2$, $-N{=}CR_7R_8$, and halogen.

In one embodiment of the present invention, $R_9$ is $-L-A$, and the pyridin-2-amine derivative described above has a structure shown below:

(II-1)

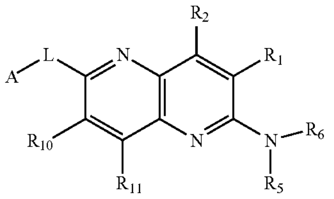

wherein,

L is a linking group having the following structure:

$$-(CH_2)_m-X-(CH_2)_n-,$$

X is selected from: one or a combination of two or more of a single bond, $-O-$, $-S-$, $-CO-$, $-C(O)O-$, $-OC(O)-$, $-CONH-$, $-NHCO-$, $-NR_7-$,

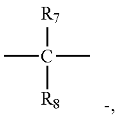

and $-S(O)_t-$; m is an integer from 0 to 10, and n is an integer from 0 to 10;

A is substituted or unsubstituted aryl or heteroaryl, such as

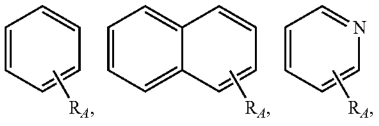

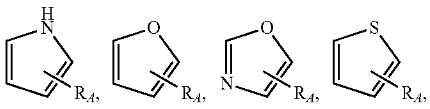

or

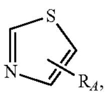

wherein $R_A$ is one or more independent substituents on the ring and has the following structure: $-Z-Y$; Z is selected from: one or a combination of two or more of

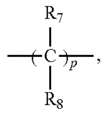

$-O-$, $-S-$, $-CO-$, $-C(O)O-$, $-OC(O)-$, $-CONH-$, $-NHCO-$, $-NR_7-$, and $-S(O)_t-$, p being an integer from 0 to 10; Y is selected from: H, halogen, $-CF_3$, $-OR_7$, $-COR_7$, $-C(O)OR_7$, $-C(O)NR_7R_8$, $-OC(O)R_7$, $-S(O)_t-R_7$, $-NR_7R_8$, $-NR_7C(O)R_8$, $-NR_7OR_8$, $-N_3$, $-CN$,

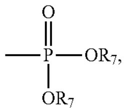

and substituted or unsubstituted heterocyclyl (in particular nitrogen-containing heterocyclyl).

In one embodiment of the present invention, in formula II-1, A is

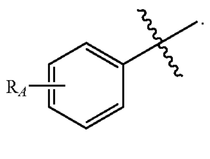

Specifically, the pyridin-2-amine derivative described above has a structure shown below:

(II-2)

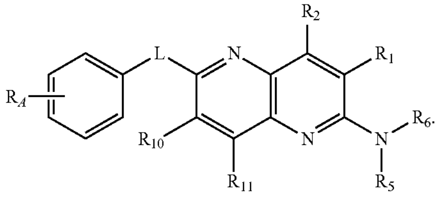

More specifically, the pyridin-2-amine derivative described above has a structure shown below:

(II-3)

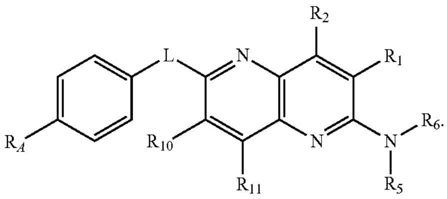

In another embodiment of the present invention, $R_3$ is —L—A, and the pyridin-2-amine derivative described above has a structure shown below:

(III)

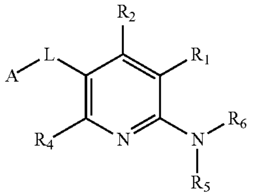

wherein,

L is a linking group having the following structure:

$-(CH_2)_m-X-(CH_2)_n-$,

X is selected from: one or a combination of two or more of a single bond, —O—, —S—, —CO—, —C(O)O—, —OC(O)—, —CONH—, —NHCO—, —$NR_7$—,

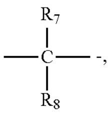

and —$S(O)_t$—; m is an integer from 0 to 10, and n is an integer from 0 to 10;

A is substituted or unsubstituted aryl or heteroaryl, such as

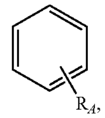 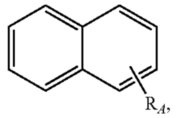 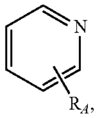

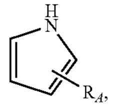 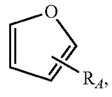 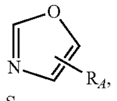 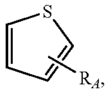 or

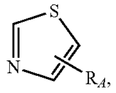

wherein $R_A$ is one or more independent substituents on the ring and has the following structure: —Z—Y; Z selected from: one or a combination of two or more of

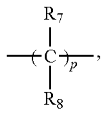

—O—, —S—, —CO—, —C(O)O—, —OC(O)—, —CONH—, —NHCO—, —$NR_7$—, and —$S(O)_t$—, p is an integer from 0 to 10; Y is selected from: H, deuterium, halogen, —$CF_3$, —$OR_7$, —$COR_7$, —$C(O)OR_7$, —$C(O)NR_7R_8$, —$OC(O)R_7$, —$S(O)_t$—$R_7$, —$NR_7R_8$, —$NR_7C(O)R_8$, —$NR_7OR_8$, —$N_3$, —CN,

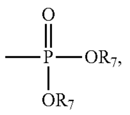

substituted or unsubstituted heterocyclyl (in particular nitrogen-containing heterocyclyl).

In one embodiment of the present invention, in formula III, A is

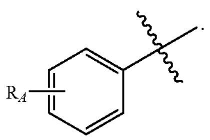

Specifically, the pyridin-2-amine derivative described above has a structure shown below:

(III-1)

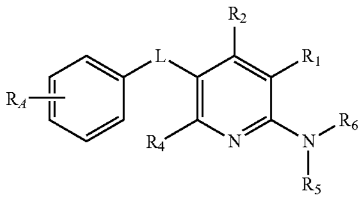

More specifically, the pyridin-2-amine derivative described above has a structure shown below:

(III-2)

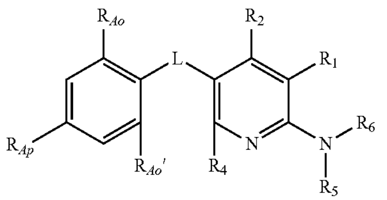

wherein $R_{Ap}$, $R_{A0}$, and $R_{A0}$' are independent substituents on the ring, each having the definition as described above for $R_A$.

Specifically, in the structure of the pyridin-2-amine derivative described above:

In one embodiment of the present invention, X is a single bond.

Specifically, m is selected from: 0, 1, 2, 3, 4, and 5.

Specifically, n is selected from: 0, 1, 2, 3, 4, and 5.

In one embodiment of the present invention, L is $-CH_2-$ or $-CH_2CH_2-$.

Specifically, p is selected from: 0, 1, 2, 3, 4, and 5.

Specifically, Z is selected from:

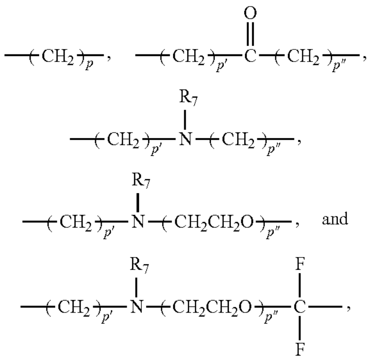

wherein p, p', and p" are independently selected from: 0, 1, 2, 3, 4, and 5, and $R_7$ is H or alkyl (e.g., methyl); more specifically, Z is selected from:

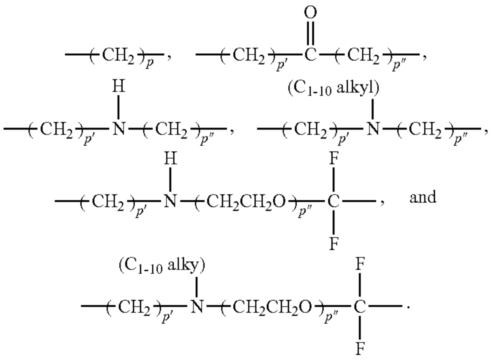

Specifically, Y is selected from: H, F, Cl, Br, $-OR_7$, $-COR_7$, $-C(O)OR_7$, $-OC(O)R_7$, $-NR_7R_8$,

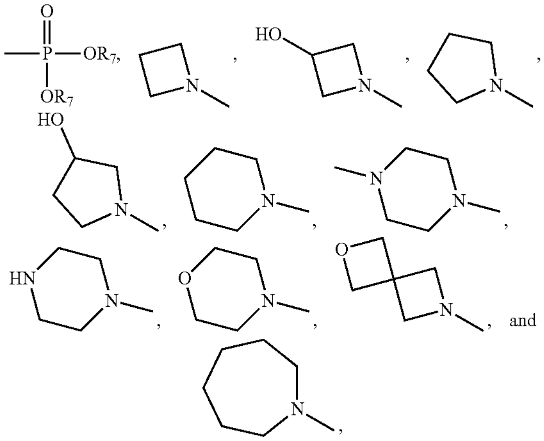

wherein $R_7$ and $R_8$ are independently selected from: H, alkyl, and cycloalkyl (e.g., cyclopropyl); and more specifically, Y is selected from: F, Cl, Br, —OH, —O($C_{1-10}$ alkyl), —COOH, —COO($C_{1-10}$ alkyl), $-NH_2$, —NH($C_{1-10}$ alkyl), —NH($C_{3-10}$ cycloalkyl), —N($C_{1-10}$ alkyl)($C_{1-10}$ alkyl),

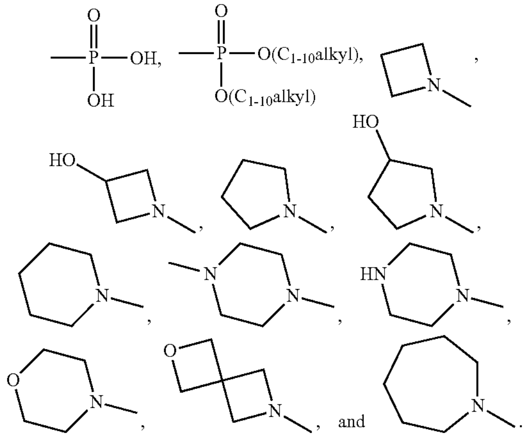

In one embodiment of the present invention, $R_1$ is $$-(CH_2)_a-Q-(CH_2)_b-CH_3,$$

wherein a is an integer from 0 to 10, b is an integer from 0 to 10, and Q is selected from: a single bond, —O—, —S—, —CO—, —C(O)O—, —OC(O)—, —CONH—, —NHCO—, and $-NR_7-$, and $R_7$ is H or alkyl; specifically, Q is selected from: a single bond, —O—, —NH—, and —N($C_{1-10}$ alkyl)-; specifically, a is selected from: 0, 1, 2, 4, and 5; and specifically, b is selected from: 0, 1, 2, 4, and 5. In an embodiment of the present invention, $R_1$ is $-CH_2CH_2CH_2CH_2CH_3-CH_2CH_2CH_2OCH_3$, and $-NHCH_2CH_2CH_2CH_3$ Specifically, $R_2$ is selected from: H, substituted or unsubstituted alkyl, halogen, —SH, $-OR_7$, $-COR_7$, $-C(O)OR_7$, $-OC(O)R_7$, $-C(O)NR_7R_8$, $-NR_7R_8$, and $-NR_7C(O)R_8$, wherein $R_7$ and $R_8$ are independently selected from: H, alkyl, and cycloalkyl; and more specifically, $R_2$ is selected from: H, $C_{1-10}$ alkyl, halogen, —SH, —OH, —O($C_{1-10}$ alkyl), —COOH, —COO($C_{1-10}$ alkyl), —C(O)NH($C_{1-10}$ alkyl), —C(O)N($C_{1-10}$ alkyl)($C_{1-10}$ alkyl), $-NH_2$, —NH($C_{1-10}$ alkyl), and —N($C_{1-10}$ alkyl)($C_{1-10}$ alkyl). In one embodiment of the present invention, $R_2$ is H.

Specifically, $R_4$ is selected from: H, substituted or unsubstituted alkyl, halogen, —SH, —$OR_7$, —$COR_7$, —C(O)$OR_7$, —OC(O)$R_7$, —C(O)$NR_7R_8$, —$NR_7R_8$, and —$NR_7$C(O)$R_8$, wherein $R_7$ and $R_8$ are independently selected from: H, alkyl, and cycloalkyl; and more specifically, $R_4$ is selected from: H, $C_{1-10}$ alkyl, halogen, —SH, —OH, —O($C_{1-10}$ alkyl), —COOH, —COO($C_{1-10}$ alkyl), —C(O)NH($C_{1-10}$ alkyl), —C(O)N($C_{1-10}$ alkyl)($C_{1-10}$ alkyl), —$NH_2$, —NH($C_{1-10}$ alkyl), and —N($C_{1-10}$alkyl)($C_{1-10}$ alkyl). In an embodiment of the present invention, $R_4$ is H or $C_{1-10}$ alkyl (e.g., methyl).

Specifically, $R_5$ and $R_6$ are independently selected from: H and substituted or unsubstituted alkyl. In an embodiment of the present invention, $R_5$ and $R_6$ are both H.

Specifically, $R_{10}$ and $R_{11}$ are independently selected from: H, substituted or unsubstituted alkyl, halogen, —SH, —$OR_7$, —$COR_7$, —C(O)$OR_7$, —OC(O)$R_7$, —C(O)$NR_7R_8$, —$NR_7R_8$, and —$NR_7$C(O)$R_8$, wherein $R_7$ and $R_8$ are independently selected from: H, alkyl, and cycloalkyl; and more specifically, $R_{10}$ and $R_{11}$ are independently selected from: H, $C_{1-10}$ alkyl, halogen, —SH, —OH, —O($C_{1-10}$ alkyl), —COOH, —COO($C_{1-10}$ alkyl), —C(O)NH($C_{1-10}$ alkyl), —C(O)N($C_{1-10}$ alkyl)($C_{1-10}$ alkyl), —$NH_2$, —NH($C_{1-10}$ alkyl), and —N($C_{1-10}$ alkyl)($C_{1-10}$ alkyl). In an embodiment of the present invention, $R_{10}$ and $R_{11}$ are both H.

Specifically, the pyridin-2-amine derivative described above has the following structure:

| No. | Structural formula |
|---|---|
| N1 | 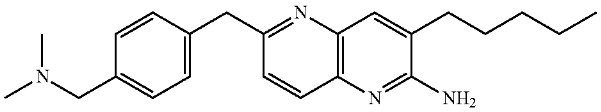 [SMILES: CCCCCc1cc2nc(Cc3ccc(CN(C)C)cc3)ccc2nc1N] |
| N2 | 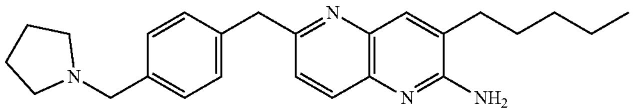 [SMILES: CCCCCc1cc2nc(Cc3ccc(CN4CCCC4)cc3)ccc2nc1N] |
| N3 | 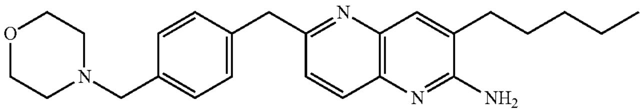 [SMILES: CCCCCc1cc2nc(Cc3ccc(CN4CCOCC4)cc3)ccc2nc1N] |
| 10 | 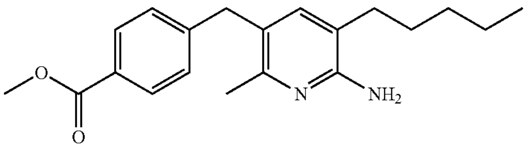 [SMILES: CCCCCc1cc(Cc2ccc(C(=O)OC)cc2)c(C)nc1N] |
| 12 | 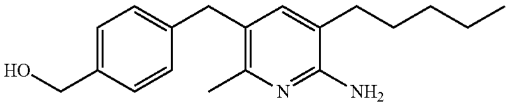 [SMILES: CCCCCc1cc(Cc2ccc(CO)cc2)c(C)nc1N] |
| 17 | 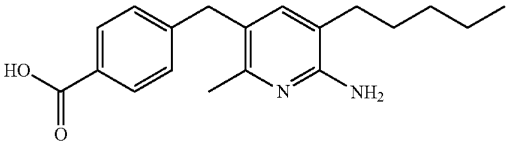 [SMILES: CCCCCc1cc(Cc2ccc(C(=O)O)cc2)c(C)nc1N] |
| N4 | 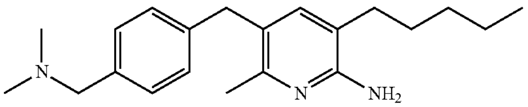 [SMILES: CCCCCc1cc(Cc2ccc(CN(C)C)cc2)c(C)nc1N] |
| N5 | 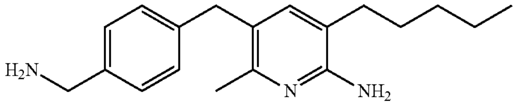 [SMILES: CCCCCc1cc(Cc2ccc(CN)cc2)c(C)nc1N] |
| N6 | 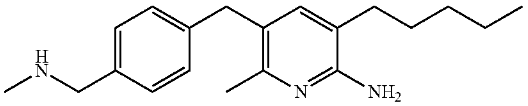 [SMILES: CCCCCc1cc(Cc2ccc(CNC)cc2)c(C)nc1N] |

-continued
| No. | Structural formula |
|---|---|
| N7 | 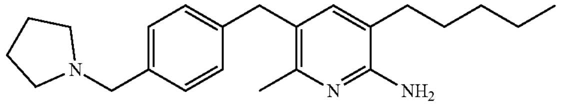 [SMILES: CCCCCc1cc(Cc2ccc(CN3CCCC3)cc2)c(C)nc1N] |
| N8 | 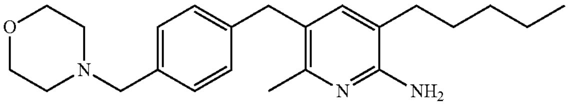 [SMILES: CCCCCc1cc(Cc2ccc(CN3CCOCC3)cc2)c(C)nc1N] |
| N9 | 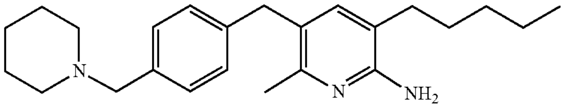 [SMILES: CCCCCc1cc(Cc2ccc(CN3CCCCC3)cc2)c(C)nc1N] |
| N10 | 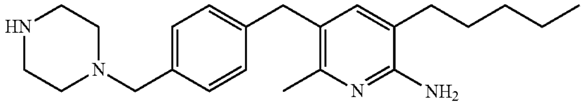 [SMILES: CCCCCc1cc(Cc2ccc(CN3CCNCC3)cc2)c(C)nc1N] |
| N11 | 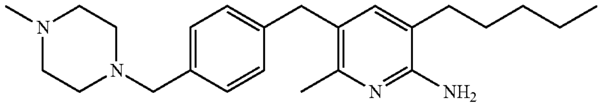 [SMILES: CCCCCc1cc(Cc2ccc(CN3CCN(C)CC3)cc2)c(C)nc1N] |
| N12 | 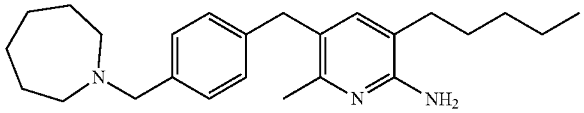 [SMILES: CCCCCc1cc(Cc2ccc(CN3CCCCCC3)cc2)c(C)nc1N] |
| N13 | 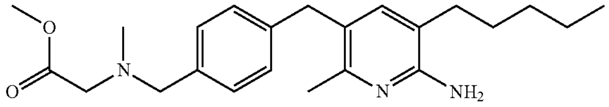 [SMILES: CCCCCc1cc(Cc2ccc(CN(C)CC(=O)OC)cc2)c(C)nc1N] |
| N14 | 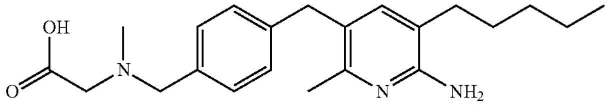 [SMILES: CCCCCc1cc(Cc2ccc(CN(C)CC(=O)O)cc2)c(C)nc1N] |
| N15 | 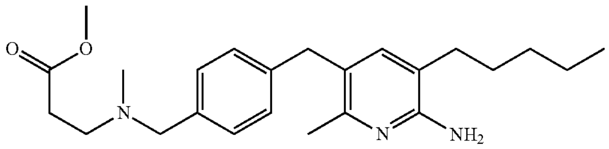 [SMILES: CCCCCc1cc(Cc2ccc(CN(C)CCC(=O)OC)cc2)c(C)nc1N] |
| N16 | 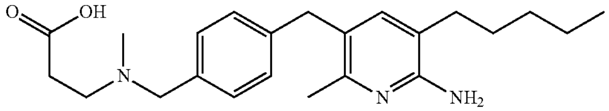 [SMILES: CCCCCc1cc(Cc2ccc(CN(C)CCC(=O)O)cc2)c(C)nc1N] |
| N17 | 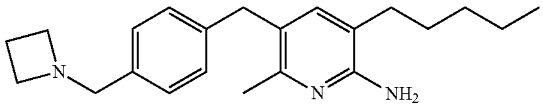 [SMILES: CCCCCc1cc(Cc2ccc(CN3CCC3)cc2)c(C)nc1N] |
| N18 | 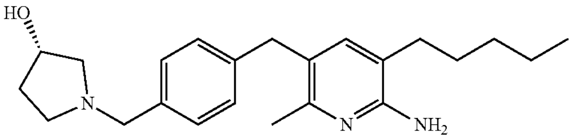 [SMILES: CCCCCc1cc(Cc2ccc(CN3CC[C@H](O)C3)cc2)c(C)nc1N] |

-continued
| No. | Structural formula |
|---|---|
| N19 | 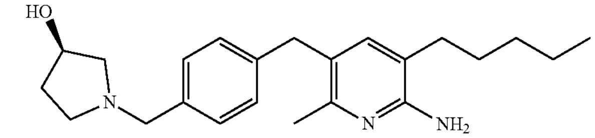 |
| N20 | 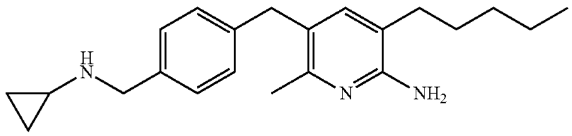 [SMILES: CCCCCc1cc(Cc2ccc(CNC3CC3)cc2)c(C)nc1N] |
| N21 | 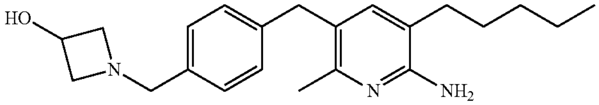 [SMILES: CCCCCc1cc(Cc2ccc(CN3CC(O)C3)cc2)c(C)nc1N] |
| N22 | 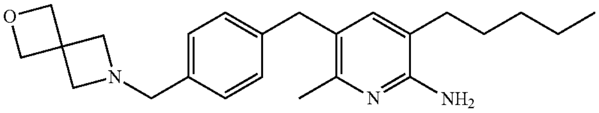 [SMILES: CCCCCc1cc(Cc2ccc(CN3CC4(COC4)C3)cc2)c(C)nc1N] |
| N23 | 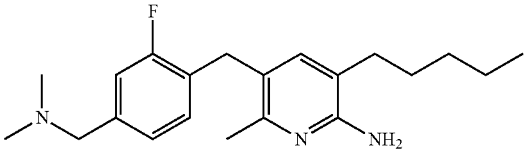 |
| N24 | 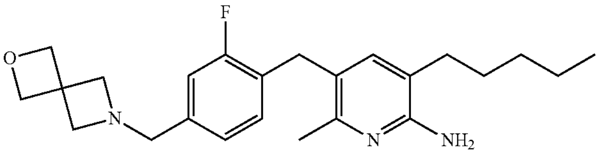 [SMILES: CCCCCc1cc(Cc2ccc(CN3CC4(COC4)C3)cc2F)c(C)nc1N] |
| N25 | 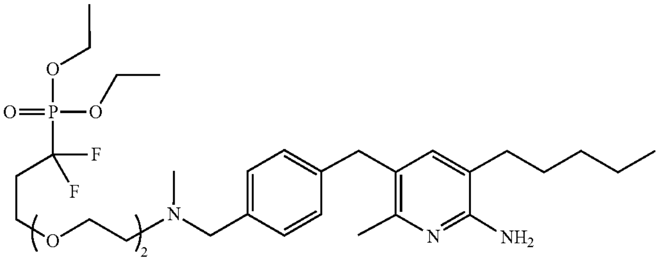 |
| N26 | 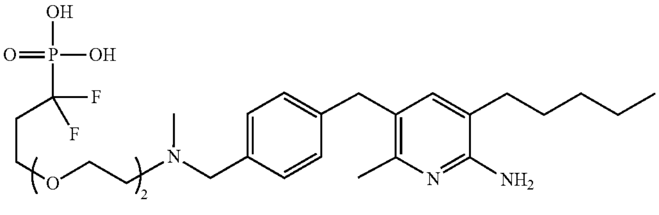 |
| N27 | 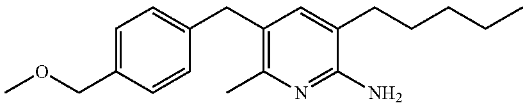 [SMILES: CCCCCc1cc(Cc2ccc(COC)cc2)c(C)nc1N] |
| N28 | 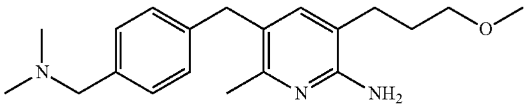 |

-continued
| No. | Structural formula |
|---|---|
| N29 | 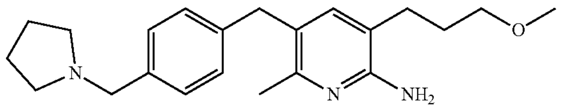 |
| N30 | 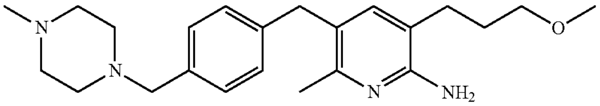 |
| N31 | 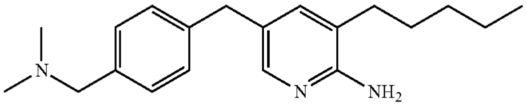 [SMILES: CCCCCc1cc(Cc2ccc(CN(C)C)cc2)cnc1N] |
| N32 | 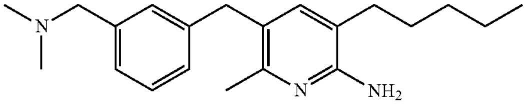 [SMILES: CCCCCc1cc(Cc2cccc(CN(C)C)c2)c(C)nc1N] |
| N33 | 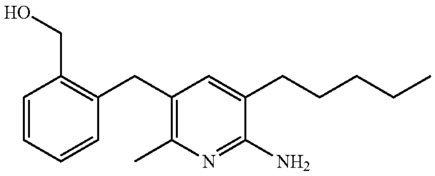 [SMILES: CCCCCc1cc(Cc2ccccc2CO)c(C)nc1N] |
| N34 | 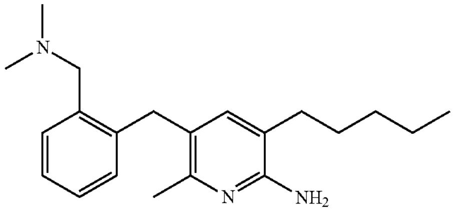 [SMILES: CCCCCc1cc(Cc2ccccc2CN(C)C)c(C)nc1N] |
| N35 | 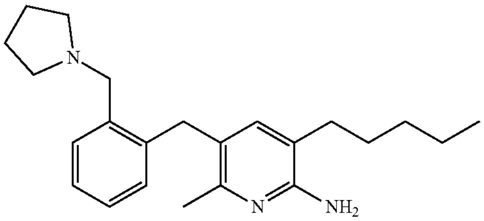 [SMILES: CCCCCc1cc(Cc2ccccc2CN2CCCC2)c(C)nc1N] |
| N36 | 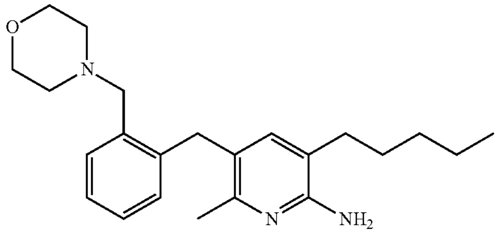 [SMILES: CCCCCc1cc(Cc2ccccc2CN2CCOCC2)c(C)nc1N] |
| N37 | 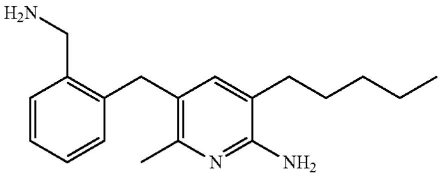 [SMILES: CCCCCc1cc(Cc2ccccc2CN)c(C)nc1N] |

-continued
| No. | Structural formula |
| --- | --- |
| N38 | 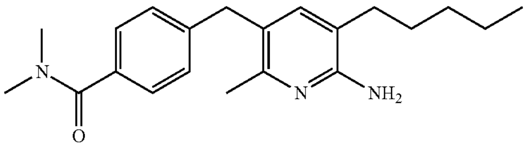 [SMILES: CCCCCc1cc(Cc2ccc(C(=O)N(C)C)cc2)c(C)nc1N] |
| N39 | 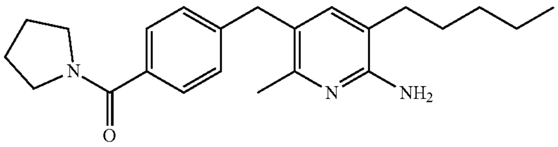 [SMILES: CCCCCc1cc(Cc2ccc(C(=O)N3CCCC3)cc2)c(C)nc1N] |
| N40 | 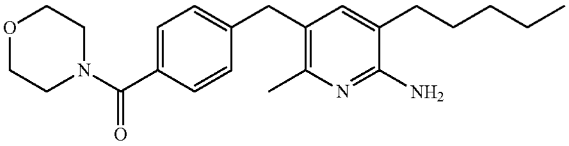 [SMILES: CCCCCc1cc(Cc2ccc(C(=O)N3CCOCC3)cc2)c(C)nc1N] |
| N41 | 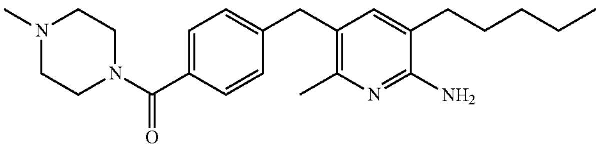 [SMILES: CCCCCc1cc(Cc2ccc(C(=O)N3CCN(C)CC3)cc2)c(C)nc1N] |
| N42 | 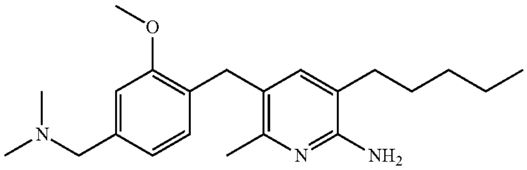 [SMILES: CCCCCc1cc(Cc2ccc(CN(C)C)cc2OC)c(C)nc1N] |
| N43 | 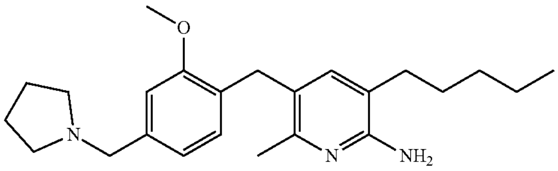 [SMILES: CCCCCc1cc(Cc2ccc(CN3CCCC3)cc2OC)c(C)nc1N] |
| N44 | 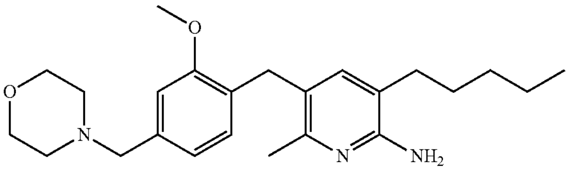 [SMILES: CCCCCc1cc(Cc2ccc(CN3CCOCC3)cc2OC)c(C)nc1N] |
| N45 | 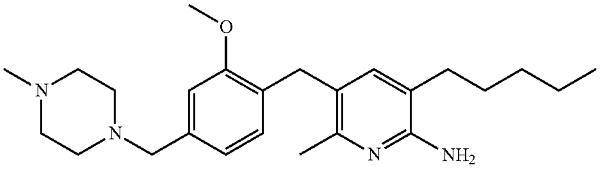 [SMILES: CCCCCc1cc(Cc2ccc(CN3CCN(C)CC3)cc2OC)c(C)nc1N] |
| N46 | 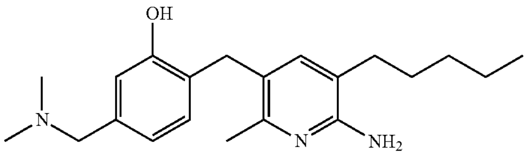 [SMILES: CCCCCc1cc(Cc2ccc(CN(C)C)cc2O)c(C)nc1N] |

-continued
| No. | Structural formula |
|---|---|
| N47 | 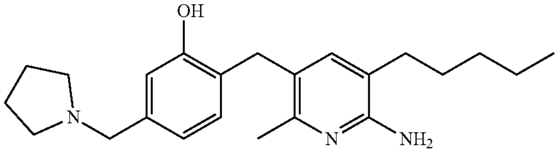 [SMILES: CCCCCc1cc(Cc2ccc(CN3CCCC3)cc2O)c(C)nc1N] |
| N48 | 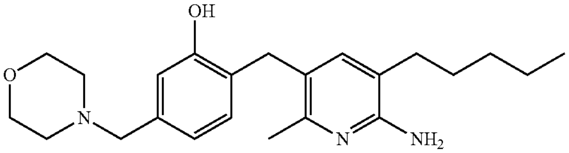 [SMILES: CCCCCc1cc(Cc2ccc(CN3CCOCC3)cc2O)c(C)nc1N] |
| N49 | 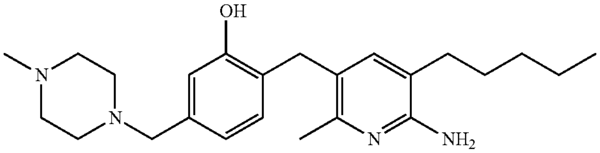 [SMILES: CCCCCc1cc(Cc2ccc(CN3CCN(C)CC3)cc2O)c(C)nc1N] |
| N50 | 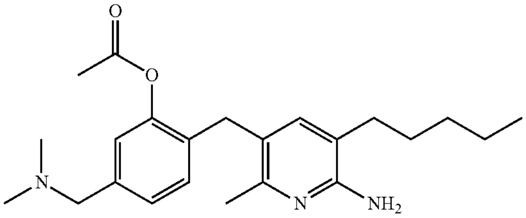 [SMILES: CCCCCc1cc(Cc2ccc(CN(C)C)cc2OC(C)=O)c(C)nc1N] |
| N51 | 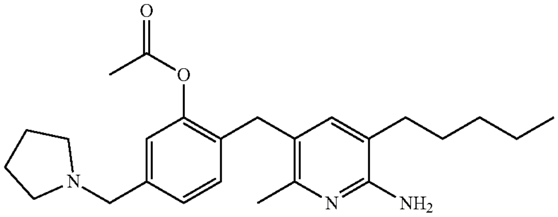 [SMILES: CCCCCc1cc(Cc2ccc(CN3CCCC3)cc2OC(C)=O)c(C)nc1N] |
| N52 | 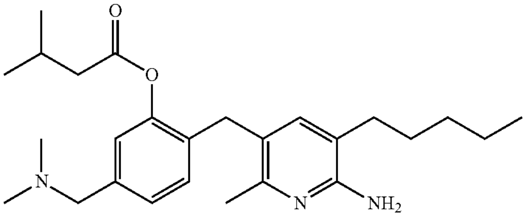 [SMILES: CCCCCc1cc(Cc2ccc(CN(C)C)cc2OC(=O)CC(C)C)c(C)nc1N] |
| N53 | 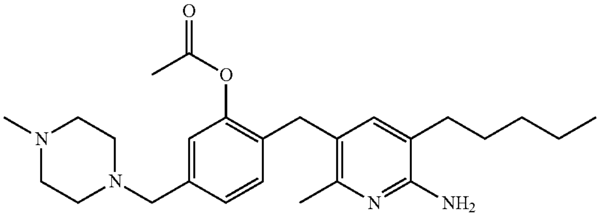 [SMILES: CCCCCc1cc(Cc2ccc(CN3CCN(C)CC3)cc2OC(C)=O)c(C)nc1N] |
| N54 | 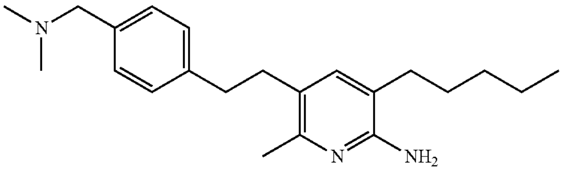 [SMILES: CCCCCc1cc(CCc2ccc(CN(C)C)cc2)c(C)nc1N] |

-continued

| No. | Structural formula |
|---|---|
| N55 | 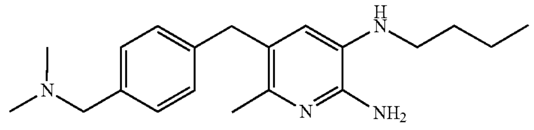 [SMILES: CCCCNc1cc(Cc2ccc(CN(C)C)cc2)c(C)nc1N] |
| N56 | 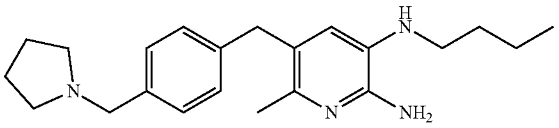 [SMILES: CCCCNc1cc(Cc2ccc(CN3CCCC3)cc2)c(C)nc1N] |
| N57 | 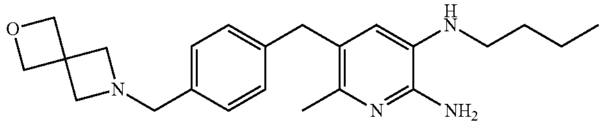 [SMILES: CCCCNc1cc(Cc2ccc(CN3CC4(COC4)C3)cc2)c(C)nc1N] |
| N58 | 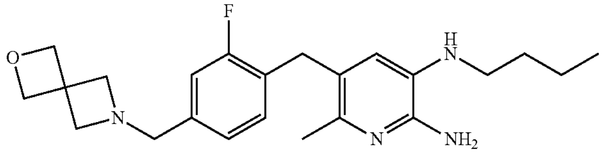 [SMILES: CCCCNc1cc(Cc2ccc(CN3CC4(COC4)C3)cc2F)c(C)nc1N] |

The present invention further provides a pharmaceutically acceptable salt, a stereoisomer, an ester, a prodrug, a solvate, or an isotopic derivative of the pyridin-2-amine derivative described above.

The present invention further provides a pharmaceutical composition, which comprises the pyridin-2-amine derivative, or the pharmaceutically acceptable salt, the stereoisomer, the ester, the prodrug, the solvate, or the isotopic derivative thereof described above, and a pharmaceutically acceptable excipient.

Specifically, the pharmaceutically acceptable excipient described above includes, but is not limited to, a sweetener, a diluent, a stabilizer, an emulsifier, a dispersant, a preservative, a colorant, a flavor enhancer, a surfactant, a wetting agent, a disintegrant, a suspending agent, an isotonic agent, a solvent, and the like.

Specifically, the pharmaceutical composition described above can be prepared into tablets, pills, capsules, powders, granules, ointments, emulsions, suspensions, solutions, suppositories, injections, inhalants, gels, and the like.

Specifically, routes of administration of the pharmaceutical composition described above include, but are not limited to, oral, rectal, transmucosal, topical, transdermal, inhalational, parenteral, sublingual, intravaginal, intranasal, intramuscular, subcutaneous, and intravenous administration.

Specifically, the pharmaceutical composition described above can further comprise at least one additional therapeutic agent, such as a chemotherapeutic agent, an immune activator, an antiangiogenic agent, a cytokine, a hormone, a polynucleotide, an antibody, and an immunologically active fragment.

Specifically, examples of the antibody described above include, but are not limited to: PR0542, which is an anti-HIVgp120 antibody fused to CD4 (Progenics/Genzyme Transgenics); MDX-010 (Medarex, N.J.), which is a humanized anti-CTLA-4 antibody; SYNAGIS (MedImmune, Md.), which is a humanized anti-respiratory syncytial virus (RSV) monoclonal antibody; HERCEPTIN (trastuzumab) (Genentech, Calif.), which is a humanized anti-HER2 monoclonal antibody; humanized anti-CD18 F(ab')2 (Genentech); CDP860, which is a humanized anti-CD18 F(ab')2 (Celltech, UK); Ostavir, which is a human anti-hepatitis B virus antibody (Protein Design Lab/Novartis); PROTOVIR™, which is a humanized anti-CMVIgG1 antibody (Protein Design Lab/Novartis); MAK-195 (SEGARD), which is a murine TNF-α F(ab')2 (Knoll Pharma/BASF); IC14, which is an anti-CD14 antibody (ICOS Pharm); a humanized anti-VEGFIgG1 antibody (Genentech); OVAREX™, which is a murine anti-CA125 antibody (Altarex); PANOREX™, which is a murine anti-17-JA cell surface antigen IgG2a antibody (Glaxo Wellcome/Centocor); BEC2, which is a murine anti-idiotype (GD3 epitope) IgG antibody (ImClone System); IMC-C225, which is a chimeric anti-EGFR IgG antibody (ImClone System); VITAXIN™, which is a humanized anti-aVP3 integrin antibody (Applied Molecular Evolution/MedImmune); Campath 1H/LDP-03, which is a humanized anti-CD52 IgG1 antibody (Leukosite); SmartM195, which is a humanized anti-CD33 IgG antibody (Protein Design Lab/Kanebo); RITUXAN™ (rituximab™), which is a chimeric anti-CD20 IgG1 antibody (IDEC Pharm/Genentech, Roche/Zettyaku); LYMPHOCIDE™, which is a humanized anti-CD22 IgG antibody (Immunomedics); SmartID10, which is a humanized anti-HLA antibody (Protein Design Lab); ONCOLYM™ (Lym-1), which is a radiolabeled murine anti-HLADR antibody (Techniclone); ABX-IL8, which is a human anti-IL8 antibody (Abgenix); anti-CD11a, which is a humanized IgG1 antibody (Genentech/Xoma); ICM3, which is a humanized anti-ICAM3 antibody (ICOS Pharm); IDEC-114, which is a primatized anti-CD80 antibody (IDEC Pharm/Mitsubishi); ZEVALIN™, which is a radiolabeled murine anti-CD20 antibody (IDEC/Schering AG); IDEC-131, which is a humanized anti-CD40L antibody (IDEC/Eisai); IDEC-151, which is a primatized anti-CD4 antibody (IDEC); IDEC-152, which is a primatized anti-CD23 antibody (IDEC/Seikagaku); SMART anti-CD3, which is a humanized anti-CD3 IgG (Protein Design Lab); 5G1.1, which is a humanized anti-complement factor 5 (C5) antibody (Alexion Pharm); D2E7, which is a humanized anti-TNF-α antibody (CAT/BASF); CDP870, which is a humanized anti-TNF-α Fab fragment (Celltech); IDEC-151, which is a primatized anti-CD4 IgG1 antibody (IDEC Pharm/SmithKline Beecham); MDX-CD4, which is a human anti-CD4 IgG antibody (Medarex/Eisai/Genmab); CDP571, which is a humanized anti-TNF-α IgG4 antibody (Celltech); LDP-02, which is a humanized anti-α4β7 antibody (LeukoSite/Genentech); OrthoCloneOKT4A, which is a humanized anti-CD4 IgG antibody (Ortho Biotech); ANTOVA™, which is a humanized anti-CD40L IgG antibody (Biogen); ANTEGREN™ which is a humanized anti-VLA-4 IgG antibody (Elan); MDX-33, which is a human anti-CD64 (FcγR) antibody (Medarex/Centeon); SCH55700, which is a humanized anti-IL-5 IgG4 antibody (Celltech/Schering); SB-240563 and SB-240683, which are humanized anti-IL-5 and anti-IL-4 antibodies, respectively (SmithKline Beecham); rhuMab-E25, which is a humanized anti-IgE IgG1 antibody (Genentech/Norvartis/Tanox Biosystems); ABX-CBL, which is a murine anti-CD147 IgM antibody (Abgenix); BTI-322, which is a rat anti-CD2 IgG antibody (Medimmune/BioTransplant); Orthoclone/OKT3, which is a murine anti-CD3 IgG2a antibody (ortho Biotech); SIMULECT™, which is a chimeric anti-CD25 IgG1 antibody (Novartis Pharm); LDP-01, which is a humanized anti-β2-integrin IgG antibody (LeukoSite); anti-LFA-1, which is a murine anti-CD18 F(ab')2 (Pasteur-Merieux/Immunotech); CAT-152, which is a human anti-TGF-β2 antibody (Cambridge Ab Tech); CorsevinM, which is a chimeric anti-Factor VII antibody (Centocor); MDX-1106, which is a PD-1 antibody (bristol-myerssquibb); and MDX-1105, which is a PDL1 antibody (Roche).

In one embodiment of the present invention, the antibody described above is an HIV antibody and a PD-1 antibody. Specifically, examples of the anti-cancer agent described above include, but are not limited to: acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterones, caracemide, carbetimer, carboplatin, carmustine, carubicin hydrochloride, carzelesin, cedefingol, chlorambucil, cirolemycin, cisplatin, cladribine, crisinatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine sodium phosphate, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon α-2a, interferon α-2b, interferon α-n1, interferon α-n3, interferon β-Ia, interferon γ-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurine, tirapazamine, toremifene citrate, trestolone acetate, triciribine phosphate, trimetrexate, trimetrexate glucuronate, triptorelin, tubulozole hydrochloride, uramustine, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, and zorubicin hydrochloride. Other anti-cancer agents that can be used include, but are not limited to: 5-ethynyluracil, abiraterone, aclarubicin, acylfulvene, adecyphenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein 1, antiandrogen, prostate cancer, antiestrogen, antineoplaston, antisense oligonucleotides, aphidicolin glycinate, apoptosis gene regulators, apoptosis regulators, apurinic acid, ara-CDP-DL-PTBA, arginine deaminase, asulacrine, atamestane, atrimustine, axinastatin 1, axinastatin 2, axinastatin 3, azasetron, azalomycin, azatyrosine, baccatin III derivatives, balanol, batimastat, BCR/ABL antagonists, benzochlorin, benzoylstaurosporine, β-lactam derivatives, β-alethine, betaclamycin B, betulinic acid, bFGF inhibitors, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL2, capecitabine, carboxamide-amino-triazole, carboxyamidotriazole, CaRestM3, CARN700, cartilage derived inhibitors, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogues, conagenin, crambescidin 816, crisinatol, cryptophycin 8, cryptophycin A derivatives, curacin A, cyclopentanthraquinone, cycloplatam, cypemycin, cytarabine ocfosfate, cytolytic factor, cytostatin, daclix-imab, decitabine, dehydrodidemnin B, deslorelin, dexamethasone, dexifosfamide, dexrazoxane, dexverapamil, diaziquone, didemnin B, didox, diethyl n-spermine, dihydro-5-azacytidine, dihydrotaxol, 9-dioxamycin, diphenylspiromustine, docetaxel, docosanol, dolasetron, doxifluridine, droloxifene, dronabinol, duocarmycin SA, ebselen, ecomustine, edelfosine, edrecolomab, eflornithine, elemene, emitefur, epirubicin, epristeride, estramustine analogues, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadoliniumtexaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, flavin, idoxifene, idramantone, ilmofosine, ilomastat, imidazoacridone, imiquimod, immunostimulant peptides, insulin-like growth factor 1 receptor inhibitors, interferon agonists, interferons, interleukins, iobenguane, iododoxorubicin, 4-ipomeanol, iroplact, irsogladine, isobengazole, isohomohalicondrin B, itasetron, jasplakinolide, kahalalide F, lamellarin-N-triacetic acid, lanreotide, leinamycin, lenograstim, lentinan sulfate, leptolstatin, letrozole, leukemia inhibiting factors, leukocyte α interferon, leuprorelin+estrogen+progesterone, leuprorelin, levamisole, liarozole, linear polyamine analogues, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetiumtexaphyrin, lysofylline, lytic peptides, maitansine, mannostatin A, marimastat, masoprocol, maspin, matrilysin inhibitors, matrix metalloproteinase inhibitors, menogaril, merbarone, metirelin, methioninase, metoclopramide, MIF inhibitors, mifepristone, miltefosine, mirimostim, mismatched double-stranded RNA, mitoguazone, mitolactol, mitomycin analogues, mitonafide, mitotoxin fibroblast growth factor-saporin, mitoxantrone, mofarotene, molgramostim, monoclonal antibodies, human chorionic gonadotropin, monophosphoryl lipid A+mycobacterial cell wall skeleton, mopidanol, multidrug resistance gene inhibitors, multiple tumor suppressor 1-based therapies, mustard anticancer agents, mycaperoxide B, mycobacterial cell wall extracts, myriaporone, N-acetyldinaline, N-substituted benzamides, nafarelin, nagrestip, naloxone+pentazocine, naparvin, naphterpin, nartograstim, nedaplatin, nemorubicin, neridronic acid, neutral endopeptidase, nilutamide, nisamycin, nitric oxide modulators, nitroxide antioxidants, nitrullyn, O6-benzylguanine, octreotide, okicenone, oligonucleotides, onapristone, ondansetron, ondansetron, oracin, oral cytokine inducers, ormaplatin, osaterone, oxaliplatin, oxaunomycin, paclitaxel, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitors, platinum complexes, platinum compounds, platinum-triamine complexes, porfimer sodium, porfiromycin, prednisone, propylbisacridone, prostaglandin J2, proteasome inhibitors, protein A-based immunomodulators, protein kinase C inhibitors, protein kinase C inhibitors, microalgal, protein tyrosine phosphatase inhibitors, purine nucleoside phosphorylase inhibitors, purpurin, pyrazoline acridines, pyridoxalated hemoglobin polyoxyethylene conjugates, raf antagonists, raltitrexed, ramosetron, ras farnesyl protein transferase inhibitors, ras inhibitors, ras-GAP inhibitors, demethylated retelliptine, rhenium Re186 etidronate, rhizomycin, ribozymes, RII retinamide, rogletimide, rohitukine, romurtide, roquinimex, rubiginone B1, ruboxyl, safingol, saintopin, SarCNU, sarcophytol A, sargramostim, Sdil mimetics, semustine, senescence-derived inhibitor 1, sense oligonucleotides, signal transduction inhibitors, signal transduction modulators, single chain antigen-binding proteins, sizofuran, sobuzoxane, sodium borocaptate, sodium phenylacetate, solverol, somatomedin binding proteins, sonermin, sparfosic acid, spicamycin D, spiromustine, splenopentin, spongistatin 1, squalamine, stem cell inhibitors, stem cell division inhibitors, stipiamide, stromelysin inhibitors, sulfinosine, superactive vasoactive intestinal peptide antagonists, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thiocoraline, thrombopoietin, thrombopoietin mimetics, thymalfasin, thymopoietin receptor agonists, thymotrinan, thyroid stimulating hormone, tin ethyl etiopurpurin, tirapazamine, titanocene dichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostin, UBC inhibitors, ubenimex, urogenital sinus-derived growth inhibitory factor, urokinase receptor antagonists, vapreotide, variolin B, vector systems, erythrocyte gene therapy, velaresol, veramine, verdins, verteporfin, vinorelbine, vinxaltine, vitaxin, vorozole, zanoterone, zeniplatin, zilascorb, and zinostatin stimalamer.

The present invention further provides use of the pyridin-2-amine derivative, or the pharmaceutically acceptable salt, the stereoisomer, the ester, the prodrug, the solvate, or the isotopic derivative thereof and the pharmaceutical composition described above in preparing a medicament for preventing and/or treating a disease associated with TLR activity.

In one embodiment of the present invention, the TLR described above is TLR8.

The present invention further provides use of the pyridin-2-amine derivative, or the pharmaceutically acceptable salt, the stereoisomer, the ester, the prodrug, the solvate, or the isotopic derivative thereof and the pharmaceutical composition described above in preparing a medicament for preventing and/or treating a disease caused by or associated with pathogen infection, an immunological disease, an inflammation, or a tumor.

Specifically, the pathogen can be a microorganism, parasite, (protozoon, worm, etc.) or other vehicles; specifically, the microorganism described above can be selected from: one or more of a virus, a *chlamydia*, a *rickettsia*, a *mycoplasma*, a bacterium, a spirochete, a fungus, and the like. Specifically, examples of the virus described above include, but are not limited to: Ebola virus disease, anthrax disease, condyloma *acuminatum*, verruca simplex, plantar wart, respiratory syncytial virus (RSV), hepatitis B virus (HBV), hepatitis C, dengue virus, herpes simplex virus (e.g., HSV-I, HSV-II, CMV, or VZV), molluscum contagiosum, cowpox, smallpox, lentivirus, human immunodeficiency virus (HIV), human papilloma virus (HPV), cytomegalovirus (CMV), varicella-zoster virus (VZV), rhinovirus, enterovirus, adenovirus, influenza virus, parainfluenza virus, mumps virus, measles virus, papovavirus, flavivirus, retrovirus, arenavirus (e.g., LCM, Junin virus, Machupo virus, Guanarito virus, and Lassa fever), and filovirus (e.g., Ebola virus or Marburg virus); particularly, HIV and HBV.

Specifically, the immunological diseases described above are autoimmune diseases, including but not limited to: systemic lupus erythematosus, rheumatoid arthritis, inflammatory bowel disease, Sjogren's syndrome, polymyositis, vasculitis, Wegener's granulomatosis, sarcoidosis, ankylosing spondylitis, Reiter's syndrome, psoriatic arthritis, Behcet's syndrome, and the like.

Specifically, examples of the tumor described above include, but are not limited to: human sarcomas and carcinomas, such as fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic carcinoma, prostate carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchial carcinoma, hepatoma, bile duct carcinoma, choriocarcinoma, seminoma, embryonal carcinoma, nephroblastoma, cervical carcinoma, testicular tumor, lung carcinoma, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, such as acute lymphocytic leukemia and acute myeloblastic leukemia (myeloblastic, promyelocytic, myelmonocytic, monocytic, and erythrocytic leukemias); chronic leukemias (chronic myeloid (granulocytic) leukemia and chronic lymphocytic leukemia); and polycythemia vera, lymphomas (Hodgkin's disease and non-Hodgkin's disease), multiple myeloma, Waldenstrom's macroglobulinemia, and heavy chain disease; particularly, colon carcinoma, bladder carcinoma, melanoma, meningioma, lung carcinoma, or pancreatic carcinoma.

The present invention further provides use of the pyridin-2-amine derivative, or the pharmaceutically acceptable salt, the stereoisomer, the ester, the prodrug, the solvate, or the isotopic derivative thereof and the pharmaceutical composition described above in preparing a vaccine adjuvant.

The present invention further provides use of the pyridin-2-amine derivative, or the pharmaceutically acceptable salt, the stereoisomer, the ester, the prodrug, the solvate, or the isotopic derivative thereof and the pharmaceutical composition described above in a medicament for enhancing an immune response.

Specifically, the medicament described above selectively modulates TLR8.

The present invention further provides use of the pyridin-2-amine derivative, or the pharmaceutically acceptable salt, the stereoisomer, the ester, the prodrug, the solvate, or the isotopic derivative thereof and the pharmaceutical composition described above in a medicament for enhancing a chemotherapeutic effect.

The present invention further provides use of the pyridin-2-amine derivative, or the pharmaceutically acceptable salt, the stereoisomer, the ester, the prodrug, the solvate, or the isotopic derivative thereof and the pharmaceutical composition described above in a medicament for enhancing an anti-HIV effect.

The present invention further provides use of the pyridin-2-amine derivative, or the pharmaceutically acceptable salt, the stereoisomer, the ester, the prodrug, the solvate, or the isotopic derivative thereof and the pharmaceutical composition described above in a medicament for preventing HIV rebound.

The present invention further provides a method for preventing and/or treating a disease associated with TLR activity, comprising a step of administering to a subject in need thereof an effective amount of the pyridin-2-amine derivative or the pharmaceutically acceptable salt, the stereoisomer, the ester, the prodrug, the solvate, or the isotopic derivative thereof, or the pharmaceutical composition described above.

The present invention further provides a method for preventing and/or treating a disease caused by or associated with pathogen infection, an immunological disease, an inflammation, or a tumor, comprising a step of administering to a subject in need thereof an effective amount of the pyridin-2-amine derivative or the pharmaceutically acceptable salt, the stereoisomer, the ester, the prodrug, the solvate, or the isotopic derivative thereof, or the pharmaceutical composition described above.

The present invention further provides a method for enhancing an immune response, comprising a step of administering to a subject in need thereof an effective amount of the pyridin-2-amine derivative or the pharmaceutically acceptable salt, the stereoisomer, the ester, the prodrug, the solvate, or the isotopic derivative thereof, or the pharmaceutical composition described above.

The present invention further provides a method for enhancing a chemotherapeutic effect, comprising a step of administering to a subject in need thereof an effective amount of the pyridin-2-amine derivative or the pharmaceutically acceptable salt, the stereoisomer, the ester, the prodrug, the solvate, or the isotopic derivative thereof, or the pharmaceutical composition described above.

The present invention further provides a method for enhancing an anti-HIV effect, comprising a step of administering to a subject in need thereof an effective amount of the pyridin-2-amine derivative or the pharmaceutically acceptable salt, the stereoisomer, the ester, the prodrug, the solvate, or the isotopic derivative thereof, or the pharmaceutical composition described above.

Specifically, the subject described above is a mammal, particularly a human.

BRIEF DESCRIPTION OF THE SEVERAL VIEWS OF THE DRAWING(S)

Not Applicable.

DETAILED DESCRIPTION OF THE INVENTION

Unless otherwise defined, all scientific and technical terms used in the present invention have the same meaning as commonly understood by those skilled in the art to which the present invention relates.

The term "alkyl" refers to a linear or branched hydrocarbon chain radical which does not contain unsaturated bonds and is linked to the rest of the molecule via a single bond. Typical alkyl groups contain 1 to 12 (e.g., 1, 2, 3, 4, 5, 6, 7, 8, 9, 10, 11, or 12) carbon atoms, such as methyl, ethyl, n-propyl, isopropyl, n-butyl, tert-butyl, n-pentyl, n-hexyl, n-heptyl, and the like. If alkyl is substituted with cycloalkyl, it is correspondingly "cycloalkylalkyl", such as cyclopropylmethyl. If alkyl is substituted with aryl, it is correspondingly "aralkyl", such as benzyl, benzhydryl or phenethyl. If alkyl is substituted with heterocyclyl, it is correspondingly "heterocyclylalkyl".

The term "alkenyl" refers to a linear or branched hydrocarbon chain radical containing at least two carbon atoms and at least one unsaturated bond, which is linked to the rest of the molecule via a single bond. Typical alkenyl groups contain 2 to 12 (e.g., 2, 3, 4, 5, 6, 7, 8, 9, 10, 11, or 12) carbon atoms, such as ethenyl, 1-methyl-ethenyl, 1-propenyl, 2-propenyl, or butenyl.

The term "alkynyl" refers to a linear or branched hydrocarbon chain radical containing at least two carbon atoms and at least one carbon-carbon triple bond, which is linked to the rest of the molecule via a single bond. Typical alkynyl groups contain 2 to 12 (e.g., 2, 3, 4, 5, 6, 7, 8, 9, 10, 11, or 12) carbon atoms, such as ethynyl, propynyl (e.g., 1-propynyl or 2-propynyl), or butynyl (e.g., 1-butynyl, 2-butynyl, or 3-butynyl).

The term "cycloalkyl" refers to alicyclic hydrocarbons. Typical cycloalkyl groups contain 1 to 4 monocyclic and/or fused rings, and 3 to 18 (e.g., 3, 4, 5, 6, 7, 8, 9, 10, 11, or 12) carbon atoms, such as cyclopropyl, cyclohexyl, or adamantyl.

The term "aryl" refers to a monocyclic or polycyclic radical, including polycyclic radicals containing monoaryl and/or fused aryl groups. Typical aryl groups contain 1 to 3 monocyclic or fused rings and 6 to 18 (e.g., 6, 7, 8, 9, 10, 12, 14, 16, or 18) carbon ring atoms, such as phenyl, naphthyl, biphenyl, indenyl, phenanthryl, or anthracyl.

The term "heterocyclyl" includes heteroaromatic and heteroalicyclic groups containing 1 to 3 monocyclic and/or fused rings and 3 to 18 (e.g., 3, 4, 5, 6, 7, 8, 9, 10, 11, 12, 14, 16, or 18) ring atoms. The heteroaryl may contain 1, 2, or 3 heteroatoms selected from N, O, and S atoms. The heteroaryl includes, for example, coumarin, including 8-coumarin, quinolyl, including 8-quinolyl, isoquinolyl, pyridinyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl, and furopyridinyl. The heteroalicyclic groups may contain 1, 2, or 3 heteroatoms selected from N, O, and S atoms. The heteroalicyclic groups include, for example, aziridine, pyrrolidinyl, tetrahydrofuryl, dihydrofuran, tetrahydrothienyl, tetrahydrothiopyranyl, piperidinyl, morpholinyl, thiomorpholinyl, oxathianyl, piperazinyl, azetidinyl, oxetanyl, thietanyl, homopiperidinyl, oxiranyl, thiiranyl, azepinyl, oxazepanyl, diazepinyl, triazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolyl, dihydropyranyl, dihydrothienyl, pyrazolidinyl, imidazolinyl, imidazolidinyl, 3-azabicyclo[3.1.0]hexyl, 3-azabicyclo[4.1.0]heptyl, 3H-indolyl, quinolizinyl, and the like.

The groups described above may be substituted at one or more available positions with one or more suitable groups such as, OR', =O, SR', SOR', $SO_2R'$, $OSO_2R'$, $OSO_3R'$, $NO_2$, NHR', $N(R')_2$, =N—R', N(R')COR', $N(COR')_2$, $N(R')SO_2R'$, N(R')C(=NR')N(R')R', $N_3$, CN, halogen, COR', COOR', OCOR', OCOOR', OCONHR', $OCON(R')_2$, CONHR', $CON(R')_2$, CON(R')OR', $CON(R')SO_2R'$, $PO(OR')_2$, PO(OR')R', PO(OR')(N(R')R'), $C_1$-$C_{12}$ alkyl, $C_3$-$C_{10}$ cycloalkyl, $C_2$-$C_{12}$ alkenyl, $C_2$-$C_{12}$ alkynyl, aryl and heterocyclyl, wherein each R' group is independently selected from hydrogen, OH, $NO_2$, $NH_2$, SH, CN, halogen, COH, CO alkyl, COOH, $C_1$-$C_{12}$ alkyl, $C_3$-$C_{10}$ cycloalkyl, $C_2$-$C_{12}$ alkenyl, $C_2$-$C_{12}$ alkynyl, aryl and heterocyclyl. These groups themselves are substituted, and the substituents may be selected from the foregoing list.

"Halogen" refers to bromine, chlorine, iodine, or fluorine.

The term "TLR" refers to a Toll-like receptor.

The term "pharmaceutically acceptable" refers to materials that have no biologically or otherwise undesirable effects, e.g., the materials may be incorporated into a pharmaceutical composition to be administered to a patient without causing any undesirable biological effects or interacting in a deleterious manner with any of the other ingredients of the composition in which it is contained. When the term "pharmaceutically acceptable" is used to refer to a pharmaceutical carrier or an excipient, it means that the carrier or the excipient meets the required standards for toxicological and manufacturing tests or that it is included in the Inactive Ingredient Guide provided by the U.S. Food and Drug Administration.

The term "pharmaceutically acceptable salt" refers to an acidic or basic salt that is theoretically non-toxic, non-irritating, and non-allergic, and capable of achieving or providing clinically acceptable pharmacokinetic, absorption, distribution, and metabolic properties of pharmaceutical molecules to be capable of achieving intended purposes. The salt described in the present invention includes a pharmaceutically acceptable acid or basic salt of an acidic, basic, or amphoteric group in the compound. A list of suitable salts can be found in S. M. Birge, et al., *J. Pharm. Sci.,* 66, 1-19 (1977).

The term "pharmaceutical composition" refers to a product obtained by mixing or combining more than one active ingredient and includes both fixed and non-fixed combinations of active ingredients.

The term "TLR disease" or "disease associated with TLR activity" refers to any disease state associated with toll-like receptors.

The room temperature described in the present invention is 20-30° C.

The disclosures of the various publications, patents, and published patent specifications cited herein are hereby incorporated by reference in their entireties.

The technical schemes of the present invention will be clearly and completely described below with reference to the examples of the present invention, and it is obvious that the described examples are only a part of the examples of the present invention but not all of them. Based on the examples of the present invention, all other examples obtained by those of ordinary skills in the art without creative work shall fall within the protection scope of the present invention.

COMPOUND PREPARATION EXAMPLES

The raw materials and reagents employed in the present invention were all commercially available from commercial suppliers including, but not limited to: Aldrich Chemical Company and Lancaster Synthesis Ltd. Among them, dimethylformamide, tetrahydrofuran and dioxane were all super-dry solvents purchased from J&K Scientific and stored in a glovebox, and dichloromethane and acetone were taken from the solvent purification system, respectively. All glassware used for water-sensitive reactions was first dried in an oven at 100° C. The raw materials and reagents used were used directly without further treatment, unless otherwise indicated.

The $^{1}H$ NMR and $^{13}C$ NMR spectra were obtained using a Bruker DRX 400 type nuclear magnetic resonance spectrometer, chemical shifts being expressed in ppm. Tetramethylsilane internal standard (0.00 ppm), $CDCl_3$ or DMSO-d6 was used as a solvent (or other solvents). 1H NMR was represented as: s=singlet, d=doublet, t=triplet, m=multiplet, br=broadened, dd=doublet of doublet, dt=doublet of triplet. If the coupling constant was provided, it was expressed in Hz. Mass spectra were determined using a Finnigan Advantage type mass spectrometer with ionization mode of ESI. The compounds were purified by column chromatography (silica gel GF254: 200-400 mesh). The purity of the compounds, as determined by HPLC unless otherwise indicated, refers to an isolated yield.

Example 1: Preparation Method of Compound 3, Including the Steps as Follow (1) To a 100 mL of round-bottom flask was added methyl 3-amino-5-bromopyrimidine formate (2.3 g, 10.0 mmol), and 30 mL of tetrahydrofuran was added for dissolving. The mixture was cooled to 0° C., and then lithium aluminum hydride (760.0 mg, 20.0 mmol) was slowly added in batches. The mixture was successively stirred at 0° C. for 1.5 h. After the reaction was completed, 0.76 mL of water, 0.76 mL of 10% aqueous NaOH solution, and 2.28 mL of water were added to the reaction liquid in sequence to quench the reaction. Sonication was performed for 10 min, and then the reaction liquid was filtered. The filter residue was washed with acetone, and the filtrate was concentrated under reduced pressure and dried in vacuum to obtain a light yellow solid 1 (yield=58.0%), the reaction formula being as follows:

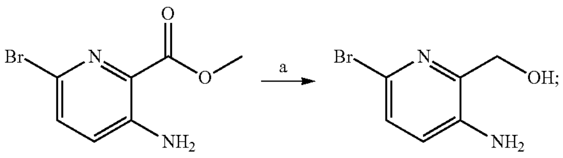

1

(2) Compound 1 (1.1 g, 5.0 mmol) was dissolved in 20 mL of dichloromethane, and manganese dioxide (0.97 g, 10.0 mmol) was added. The mixture was reacted at room temperature overnight. After the reaction was completed, the reaction liquid was filtered, and the filtrate was concentrated under reduced pressure and dried in vacuum to obtain a light yellow solid 2, the reaction formula being as follows:

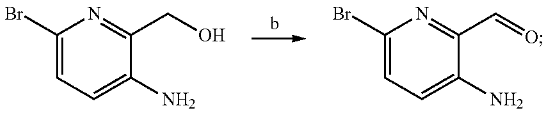

1 2

(3) Under nitrogen atmosphere, compound 2 (600.0 mg, 3.0 mmol) was dissolved in 10 mL of super-dry dimethyl sulfoxide, and n-heptanitrile (672.0 mg, 6.0 mmol) and sodium tert-butoxide (576.6 mg, 6.0 mmol) were added. The reaction liquid was heated to 60° C. and stirred for 2 h. After the reaction was completed, 20 mL of water was added to quench the reaction. The reaction liquid was extracted twice with ethyl acetate. The organic phases were combined, concentrated under reduced pressure, and purified by silica gel column chromatography (PE:EA=2:1) to obtain compound 3, the reaction formula being as follows:

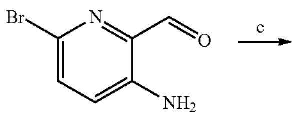

2

-continued

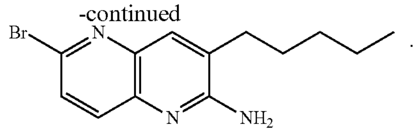

3

$^1H$ NMR (400 MHz, Chloroform-d) δ 7.87 (s, 1H), 7.78 (d, J=8.7 Hz, 1H), 7.53 (d, J=8.7 Hz, 1H), 5.33 (s, 2H), 5.07 (s, 1H), 2.57 (t, J=7.6 Hz, 2H), 1.79-1.66 (m, 2H), 1.50-1.31 (m, 4H), 1.02-0.82 (t, J=6.8 Hz, 3H). $^{13}C$ NMR (101 MHz, Chloroform-d) δ 156.57, 141.58, 140.36, 136.83, 135.35, 135.31, 128.57, 128.18, 77.26, 31.43, 30.87, 26.90, 22.48, 13.95. m/z:$[M+H]^+$ 294.2, 296.2.

Example 2: Preparation Method of Compound 6, Including the Steps as Follows (1) Under nitrogen atmosphere, compound 3 (588.0 mg, 2.0 mmol) obtained in Example 1 was dissolved in 5 mL of dry tetrahydrofuran, followed by the addition of methyl formate benzyl bromide (687.0 mg, 3.0 mmol), zinc powder (392.4 mg, 6.0 mmol), and $Ni(PPh_3)_2Cl_2$ (170.1 mg, 0.26 mmol) in sequence. The reaction liquid was stirred at room temperature for 8 h. After the reaction was completed, the reaction liquid was concentrated under reduced pressure and purified by column chromatography (PE:EA=1:1) to obtain compound 4, the reaction formula being as follows:

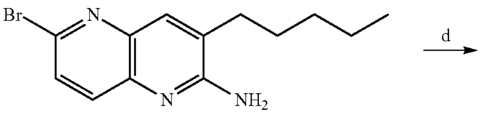

3

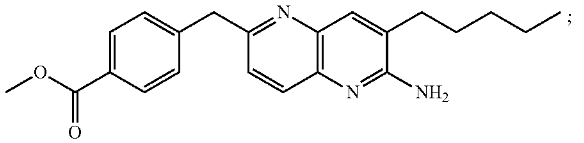

4

(2) Compound 4 (544.8 mg, 1.5 mmol) was dissolved in tetrahydrofuran (10 mL) and cooled to 0° C. Then lithium aluminum hydride (114.0 mg, 3.0 mmol) was slowly added in batches. The mixture was successively stirred at 0° C. for 2 h. After the reaction was completed, 114 μL of water, 114 μL of 10% aqueous NaOH solution, and 342 μL of water were added to the reaction liquid in sequence to quench the reaction. Sonication was performed for 10 min, and then the reaction liquid was filtered. The filter residue was washed with acetone, and the filtrate was concentrated under reduced pressure and dried in vacuum to obtain a yellow solid 5, the reaction formula being as follows:

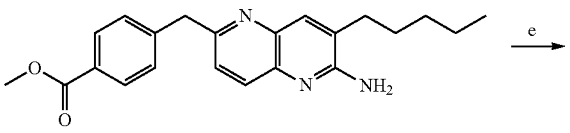

4

-continued

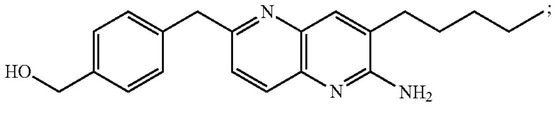

5

(3) Compound 5 (335.2 mg, 1 mmol) was dissolved in 5 mL of dry dichloromethane, and thionyl chloride (108.9 μL, 1.5 mmol) was slowly added dropwise. The reaction liquid was stirred at room temperature for 0.5 h. After the reaction was completed, the reaction liquid was concentrated under reduced pressure and dried to obtain a yellow powder 6, which was used directly without purification, the reaction formula being as follows:

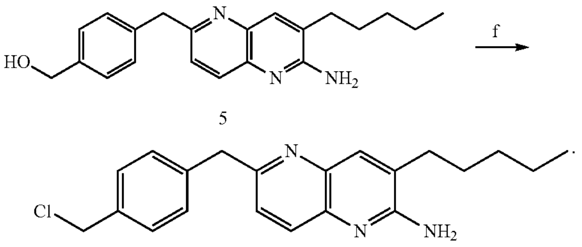

5

6

Example 3: Preparation Method of Compound N1, Including the Steps as Follows

Compound 6 prepared in Example 2 was used as a raw material. Compound 6 (88.3 mg, 0.25 mmol) was dissolved in 5 mL of dry methanol. Dimethylamine (0.375 mL, 2 M in methanol) and potassium carbonate (69.1 mg, 0.5 mmol) were added in sequence. The reaction liquid was stirred at 45° C. for 4 h. After the reaction was completed, the reaction liquid was filtered, and the filtrate was dried over anhydrous sodium sulfate, concentrated under reduced pressure, and purified by silica gel column chromatography to obtain a light yellow solid Ni, the reaction formula being as follows:

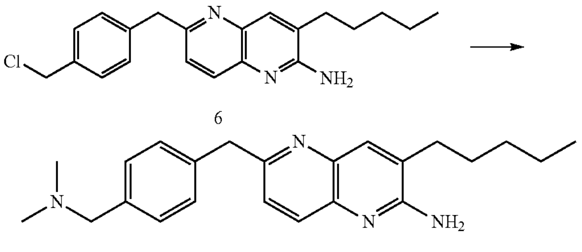

6

N1

$^1$H NMR (400 MHz, Chloroform-d) δ 7.95 (d, J=8.6 Hz, 1H), 7.84 (d, J=8.6 Hz, 1H), 7.27 (m, 4H), 5.00 (s, 2H), 4.29 (s, 2H), 3.47 (s, 2H), 2.61 (t, J=7.7 Hz, 2H), 2.29 (s, 6H), 1.80 (p, J=7.4 Hz, 2H), 1.44 (tq, J=13.7, 7.8, 6.0 Hz, 4H), 0.95 (t, J=6.8 Hz, 3H). $^{11}$C NMR (101 MHz, Chloroform-d) δ 157.27, 156.02, 140.58, 140.25, 138.64, 135.99, 133.56, 129.54, 129.10, 127.41, 124.01, 63.77, 45.04, 44.63, 31.57, 31.07, 27.18, 22.54, 13.98. m/z:$[M+H]^+$ 363.4.

Example 4: Synthesis of Compounds N2-N3

Compounds N2-N3 were obtained by replacing the compound dimethylamine with tetrahydropyrrole or morpholine according to the synthesis method of compound Ni in Example 3:

N2

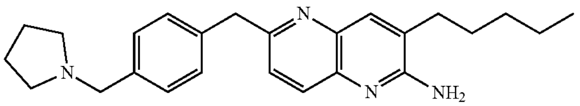

m/z:$[M+H]^+$ 389.4.

N3

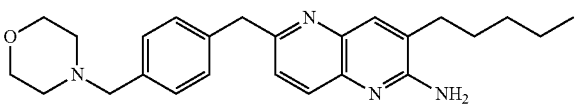

m/z:$[M+H]^+$ 405.4.

Example 5: Preparation Method of Compound 12a, Including the Steps as Follows (1) Under nitrogen atmosphere, 2-amino-3-bromo-5-methylpyridine (1.86 g, 10 mmol) was dissolved in 20 mL of toluene, and n-pentylboronic acid (1.39 g, 12 mmol), tripotassium phosphate trihydrate (5.33 g, 20 mmol), palladium acetate (112.2 mg, 0.5 mmol), and S-Phos (205.26 mg, 0.5 mmol) were added in sequence. The reaction liquid was heated to 110° C. and stirred for 3 h. After the reaction was completed, the reaction liquid was cooled to room temperature and filtered. The filtrate was dried over anhydrous sodium sulfate, concentrated under reduced pressure, and purified by silica gel column chromatography (DCM: MeOH=20:1) to obtain compound 8a, the reaction formula being as follows: Br %

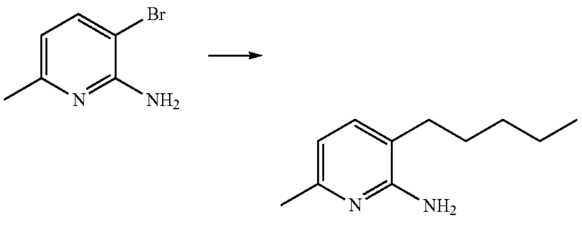

8a (2) Compound 8a (890.74 mg, 5 mmol) was dissolved in 10 mL of acetonitrile, and N-bromosuccinimide (978.89 mg, 5.5 mmol) was slowly added. The reaction liquid was stirred at room temperature for 30 min. After the reaction was completed, the reaction liquid was concentrated under reduced pressure and purified by silica gel column chromatography (PE:EA=1:1) to obtain compound 10a, the reaction formula being as follows:

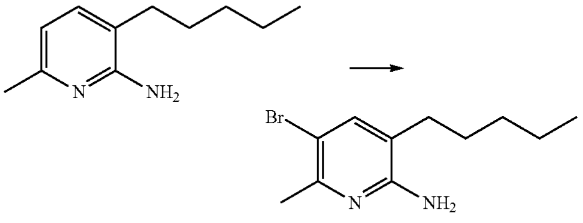

10a $^1$H NMR (400 MHz, Chloroform-d) δ 7.37 (s, 1H), 4.55 (s, 2H), 2.47 (s, 3H), 2.37 (t, J=7.8 Hz, 2H), 1.59 (m, 2H), 1.46-1.32 (m, 4H), 0.91 (t, J=6.8 Hz, 3H). $^{13}$C NMR (101 MHz, Chloroform-d) δ 154.9, 151.9, 140.2, 120.6, 108.9, 31.6, 30.2, 27.5, 23.7, 22.5, 14.1. m/z:[M+H]$^+$ 257.3, 259.3.

(3) Under nitrogen atmosphere, methyl 4-bromomethylbenzoate (1202.62 mg, 5.25 mmol) was dissolved in 10 mL of dry tetrahydrofuran, and zinc powder (686.6 mg, 10.5 mmol) was added. The reaction liquid was stirred at 0° C. for 5 h. After the reaction was completed, the reaction liquid was filtered to obtain zinc reagent. Compound 10a (900.11 mg, 3.5 mmol) was taken, and bis(dibenzylideneacetone) palladium (40.25 mg, 0.07 mmol), Q-Phos (49.7 mg, 0.07 mmol), and zinc reagent were added in sequence. The reaction liquid was heated to 80° C. and stirred for 3 h. After the reaction was completed, the reaction liquid was cooled to room temperature and filtered. The filtrate was dried over anhydrous sodium sulfate, concentrated under reduced pressure, and purified by silica gel column chromatography (DCM:MeOH=20:1) to obtain compound 12a, the reaction formula being as follows:

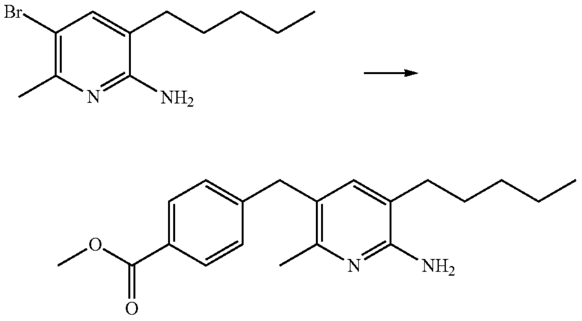

12a $^1$H NMR (400 MHz, Chloroform-d) δ 7.96 (d, J=7.8 Hz 1H), 7.18 (d, J=7.8 Hz, 1H), 7.05 (s, 1H), 3.92 (s, 3H), 2.39 (t, J=7.8 Hz, 2H), 1.59 (t, J=7.4 Hz, 1H), 1.36-1.32 (m, 4H), 0.91 (t, J=7.2 Hz, 2H). $^{13}$C NMR (101 MHz, Chloroform-d) δ 177.70, 167.08, 154.68, 146.35, 145.81, 139.84, 129.83, 128.44, 128.10, 122.79, 52.09, 37.71, 31.64, 30.33, 27.62, 22.50, 20.44, 14.05. m/z:[M+H]$^+$ 327.3.

Example 6: Synthesis of Compound 12b

Compound 12b was obtained by replacing n-pentylboronic acid with 2(3-methoxypropyl)(pinacolato)diboron according to the synthesis method of compound 12a in Example 5:

12b

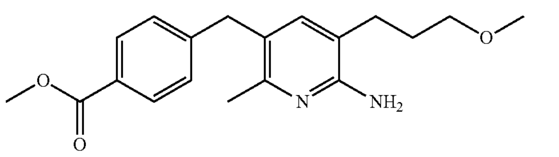

$^1$H NMR (400 MHz, Chloroform-d) δ 7.88 (d, J=7.8 Hz, 2H), 7.15 (d, J=7.8 Hz, 2H), 7.00 (s, 1H), 4.82 (m, 2H), 4.66 (s, 2H), 3.87 (s, 3H), 3.30 (t, J=6.0 Hz, 2H), 3.28 (s, 3H), 2.45 (t, J=7.4 Hz, 2H), 1.80 (m, 2H). $^{13}$C NMR (101 MHz, Chloroform-d) δ 177.82, 154.96, 151.78, 139.89, 139.52, 139.19, 130.98, 128.82, 128.50, 127.22, 123.74, 118.10, 71.17, 58.52, 37.45, 28.73, 26.57, 21.21. m/z:[M+H]$^+$ 329.3.

Example 7: Preparation Method of Compound 16a, Including the Steps as Follows (1) Compound 12a (489.3 mg, 1.5 mmol) was dissolved in 10 mL of dry tetrahydrofuran and cooled to 0° C. Lithium aluminum hydride (114.0 mg, 3.0 mmol) was slowly added in batches. The mixture was successively stirred at 0° C. for 1.5 h. After the reaction was completed, 114 μL of water, 114 μL of 10% aqueous NaOH solution, and 342 μL of water were added to the reaction liquid in sequence to quench the reaction. Sonication was performed for 10 min, and then the reaction liquid was filtered. The filter residue was washed with acetone, and the filtrate was dried over anhydrous sodium sulfate, concentrated under reduced pressure, and purified by silica gel column chromatography (DCM: MeOH=15:1) to obtain compound 14a, the reaction formula being as follows:

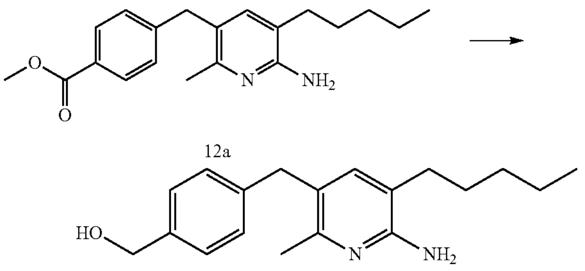

12a

14a $^1$H NMR (400 MHz, Chloroform-d) δ 7.26 (d, J=7.9 Hz, 2H), 7.07 (d, J=7.7 Hz, 2H), 7.00 (s, 1H), 4.66 (s, 2H), 4.31 (s, 2H), 3.84 (s, 2H), 2.38-2.34 (m, 2H), 2.24 (s, 3H), 1.61-1.54 (m, 2H), 1.32 (dq, J=7.5, 3.4 Hz, 4H), 0.89 (t, J=6.8 Hz, 3H). $^{13}$C NMR (101 MHz, Chloroform-d) δ 154.48, 152.18, 140.01, 139.18, 138.76, 128.57, 127.22, 123.89, 118.46, 64.97, 37.61, 31.72, 30.55, 27.82, 22.54, 21.48, 14.09. m/z:[M+H]$^+$ 299.3. (2) Compound 14a (298.2 mg, 1 mmol) was dissolved in 5 mL of dry dichloromethane, and thionyl chloride (108.9 μL, 1.5 mmol) was slowly added dropwise. The reaction liquid was stirred at room temperature for 0.5 h. After the reaction was completed, the reaction liquid was concentrated under reduced pressure and dried to obtain a yellow solid 16a, which was used directly without purification, the reaction formula being as follows:

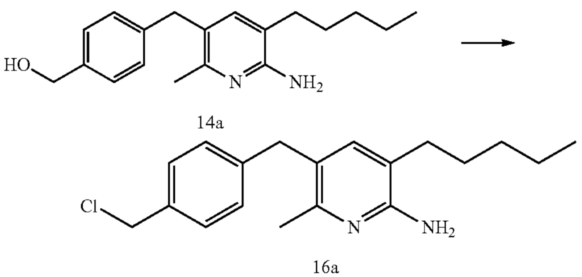

14a

16a

Example 8: Synthesis of Compound 14b

Compound 14b was obtained according to the synthesis method of compound 14a in Example 7:

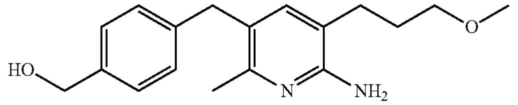

14b

$^1$H NMR (400 MHz, Chloroform-d) δ 7.25 (d, J=7.8 Hz, 2H), 7.05 (d, J=7.8 Hz, 2H), 7.00 (s, 1H), 4.87-4.73 (m, 2H), 4.64 (s, 2H), 3.81 (s, 2H), 3.35 (t, J=6.0 Hz, 2H), 3.31 (s, 3H), 2.47 (t, J=7.4 Hz, 2H), 1.81 (q, J=6.4 Hz, 2H). $^{13}$C NMR (101 MHz, Chloroform-d) δ 154.93, 151.75, 139.86, 139.53, 139.12, 130.93, 128.83, 128.49, 127.19, 123.67, 117.97, 71.13, 64.50, 58.51, 37.40, 28.7, 26.54, 21.01. m/z:$[M+H]^+$ 301.3.

Example 9: Synthesis of Compound 16b

Compound 16b was obtained according to the synthesis method of compound 16a in Example 7, the reaction formula being as follows:

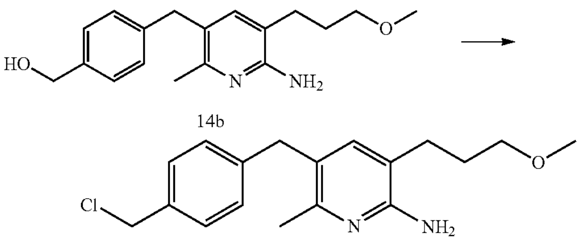

14b

16b

Example 10: Preparation Method of Compound N4

Compound 16a prepared in Example 7 was used as a raw material. Compound 13 (94.85 mg, 0.3 mmol) was dissolved in 5 mL of dry methanol. Dimethylamine (0.450 mL, 2 M in methanol) and potassium carbonate (82.93 mg, 0.6 mmol) were added in sequence. The reaction liquid was stirred at 45° C. for 4 h. After the reaction was completed, the reaction liquid was filtered, and the filtrate was dried over anhydrous sodium sulfate, concentrated under reduced pressure, and purified by silica gel column chromatography (DCM: MeOH=10:1) to obtain a white solid N4, the reaction formula being as follows:

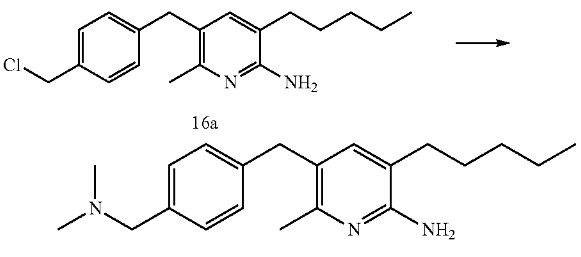

16a

N4

$^1$H NMR (400 MHz, Chloroform-d) δ 7.20 (d, J=7.8 Hz, 2H), 7.04 (d, J=7.8 Hz, 2H), 7.00 (s, 1H), 4.37 (s, 2H), 3.84 (s, 2H), 3.39 (s, 2H), 2.36 (t, J=7.8 Hz, 2H), 2.28 (s, 3H), 2.23 (s, 6H), 1.57 (m, 2H), 1.32 (m, 4H), 0.88 (t, J=6.8 Hz, 3H). $^{13}$C NMR (101 MHz, Chloroform-d) δ 154.4, 152.0, 139.4, 139.2, 136.3, 129.3, 128.4, 124.1, 118.5, 64.0, 45.3, 37.6, 31.7, 30.5, 27.8, 22.5, 21.5, 14.1. HRMS (ESI) calcd for: $C_{21}H_{32}N_3[M+H]^+$ 326.2596, found 326.2589.

Example 11: Preparation Method of Compound N5, Including the Steps as Follows (1) Compound 16a prepared in Example 7 was used as a raw material. Compound 13 (94.85 mg, 0.3 mmol) was dissolved in 5 mL of dry methanol. Bis(tert-butoxycarbonyl) amine (195.53 mg, 0.9 mmol) and potassium carbonate (82.93 mg, 0.6 mmol) were added in sequence. The reaction liquid was stirred at 45° C. for 5 h. After the reaction was completed, the reaction liquid was filtered, and the filtrate was dried over anhydrous sodium sulfate, concentrated under reduced pressure, and purified by silica gel column chromatography (DCM:MeOH=30:1) to obtain a yellow solid 22, the reaction formula being as follows:

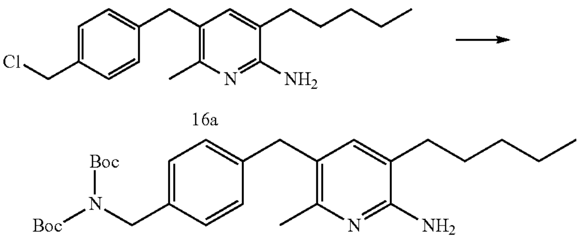

16a

22

(2) Compound 16 (49.73 mg, 0.1 mmol) was dissolved in 3 mL of dry dichloromethane, and trifluoroacetic acid (74.27 μL, 1 mmol) was slowly added dropwise. The reaction liquid was stirred at room temperature for 2 h. After the reaction was completed, saturated sodium bicarbonate solution was added dropwise to quench the reaction. The reaction liquid was extracted three times with dichloromethane/water. The organic phases were combined, dried over anhydrous sodium sulfate, concentrated under reduced pressure, and purified by silica gel column chromatography (DCM: MeOH=10:1) to obtain a light yellow solid N5, the reaction formula being as follows:

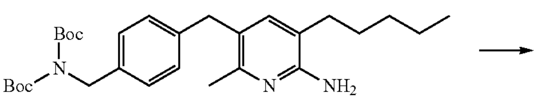

22

-continued

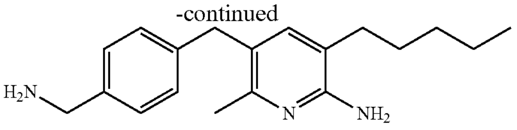

N5

$^1$H NMR (400 MHz, Chloroform-d) δ 7.21 (d, J=7.8 Hz, 2H), 7.06 (d, J=7.8 Hz, 2H), 7.01 (s, 1H), 4.41 (s, 2H), 3.84 (s, 2H), 3.82 (s, 2H), 2.37 (t, J=7.6 Hz, 2H), 2.28 (s, 3H), 2.05 (s, 2H), 1.57 (m, 2H), 1.32 (m, 4H), 0.90 (t, J=6.8 Hz, 3H). $^{13}$C NMR (101 MHz, Chloroform-d) δ 154.4, 151.9, 140.9, 139.3, 139.1, 128.6, 127.2, 124.0, 118.6, 46.1, 37.5, 31.7, 30.5, 27.8, 22.5, 21.4, 14.0. HRMS (ESI) calcd for: $C_{19}H_{28}N_3[M+H]^+$ 298.2283, found 298.2283.

Example 12: Preparation Method of Compounds N6-N26

Compounds N6-N26 were obtained by replacing the raw material dimethylamine with methylamine, tetrahydropyrrole, morpholine, piperidine, piperazine, cycloheptylamine, N-methylpiperazine, and the like according to the synthesis method of compound N4 in Example 10:

N6

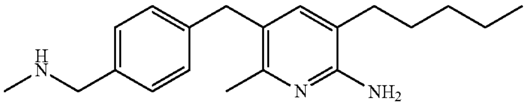

$^1$H NMR (400 MHz, Chloroform-d) δ 7.22-7.18 (d, J=8.0 Hz, 2H), 7.05 (d, J=8.0 Hz, 2H), 6.99 (s, 1H), 4.30 (s, 2H), 3.83 (s, 2H), 3.70 (s, 2H), 2.43 (s, 3H), 2.36 (t, J=7.8 Hz, 2H), 2.27 (s, 3H), 1.61-1.52 (m, 2H), 1.32 (m, 4H), 0.88 (t, J=6.8 Hz, 3H). $^{13}$C NMR (101 MHz, Chloroform-d) δ 154.4, 152.2, 139.3, 139.1, 137.8, 128.5, 128.3, 124.1, 118.4, 55.8, 37.6, 36.1, 31.7, 30.6, 27.8, 22.5, 21.6, 14.0. HRMS (ESI) calcd for: $C_{20}H_{30}N_3$ $[M+H]^+$ 312.2440, found 312.2443.

N7

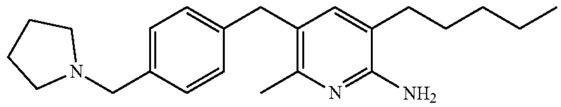

$^1$H NMR (400 MHz, Chloroform-d) δ 7.25 (d, J=7.7 Hz, 2H), 7.06 (d, J=7.7 Hz, 2H), 7.02 (s, 1H), 4.30 (s, 2H), 3.86 (s, 2H), 3.60 (s, 2H), 2.51 (m, 4H), 2.39 (t, J=7.8 Hz, 2H), 2.31 (s, 3H), 1.80 (m 4H), 1.60 (t, J=7.6 Hz, 2H), 1.35 (m, 4H), 0.94-0.88 (t, J=6.8 Hz, 3H). $^{13}$C NMR (101 MHz, Chloroform-d) δ 154.37, 152.2, 139.16, 139.08, 136.99, 129.00, 128.30, 124.19, 118.36, 60.41, 54.17, 37.57, 31.69, 30.55, 27.81, 23.42, 22.51, 21.59, 14.05. HRMS (ESI) calcd for: $C_{23}H_{34}N_3[M+H]^+$ 352.2753, found 352.2742.

N8

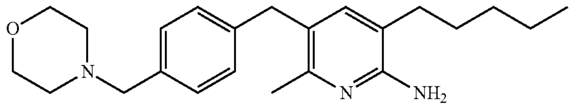

$^1$H NMR (400 MHz, Chloroform-d) δ 7.21 (d, J=7.7 Hz, 2H), 7.04 (d, J=7.7 Hz, 2H), 7.01 (s, 1H), 4.34 (s, 2H), 3.84 (s, 2H), 3.69 (t, J=4.6 Hz, 4H), 3.45 (s, 2H), 2.42 (t, J=4.5 Hz, 4H), 2.36 (d, J=7.8 Hz, 2H), 2.28 (s, 3H), 1.57 (m, 2H), 1.32 (m, 4H), 0.89 (t, J=6.6 Hz, 3H). $^{13}$C NMR (101 MHz, Chloroform-d) δ 154.39, 152.1, 139.50, 139.18, 135.34, 129.30, 128.32, 124.04, 118.44, 67.02, 63.16, 53.61, 37.56, 31.67, 30.52, 27.78, 22.51, 21.50, 14.05. HRMS (ESI) calcd for: $C_{23}H_{34}N_3O$ $[M+H]^+$ 368.2702, found 368.2700.

N9

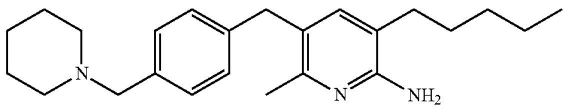

$^1$H NMR (400 MHz, Chloroform-d) δ 7.20 (d, J=7.8 Hz, 2H), 7.03 (d, J=7.8 Hz, 2H), 7.00 (s, 1H), 4.30 (s, 2H), 3.83 (s, 2H), 3.43 (s, 2H), 2.42-2.32 (m, 6H), 2.28 (s, 3H), 1.56 (m, 6H), 1.42 (m, 2H), 1.32 (m, 4H), 0.89 (t, J=6.8 Hz, 3H). $^{13}$C NMR (101 MHz, Chloroform-d) δ 154.39, 152.2, 139.16, 139.12, 136.05, 129.36, 128.18, 124.17, 118.38, 63.55, 54.45, 37.58, 31.68, 30.53, 27.79, 25.94, 24.38, 22.51, 21.57, 14.05. m/z:$[M+H]^+$ 366.4.

N10

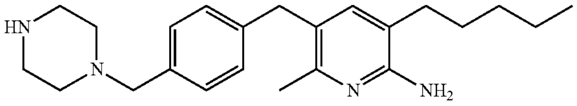

$^1$H NMR (400 MHz, Chloroform-d) δ 7.20 (d, J=7.8 Hz, 1H), 7.03 (d, J=7.8 Hz, 2H), 7.00 (s, 1H), 4.34 (s, 2H), 3.83 (s, 2H), 3.44 (s, 2H), 2.88 (m, 4H), 2.42-2.35 (m, 7H), 2.28 (s, 2H), 1.59-1.55 (m, 2H), 1.39-1.26 (m, 4H), 0.88 (t, J=6.8 Hz, 2H). $^{13}$C NMR (101 MHz, Chloroform-d) δ 154.41, 152.1, 139.4, 139.16, 135.56, 129.32, 128.26, 124.06, 118.43, 63.31, 54.22, 45.93, 37.56, 31.67, 30.52, 27.78, 22.51, 21.51, 14.05. m/z:$[M+H]^+$ 367.4.

N11

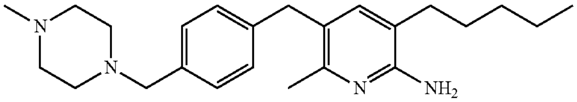

$^1$H NMR (400 MHz, Chloroform-d) δ 7.22 (d, J=7.8 Hz, 2H), 7.06 (d, J=7.8 Hz, 2H), 7.02 (s, 1H), 4.32 (s, 2H), 3.85 (s, 2H), 3.49 (s, 2H), 2.58-2.33 (m, 10H), 2.30 (s, 3H), 2.29 (s, 3H), 1.69-1.51 (m, 2H), 1.35 (m, 4H), 0.91 (t, J=6.8 Hz, 3H). $^{13}$C NMR (101 MHz, Chloroform-d) δ 154.41, 152.2, 139.3, 139.08, 135.75, 129.27, 128.26, 124.1, 118.4, 62.72, 55.15, 53.07, 46.05, 37.57, 31.67, 30.53, 27.79, 22.50, 21.58, 14.04. m/z:$[M+H]^+$ 381.5.

N12

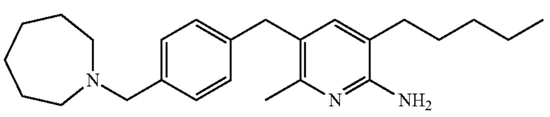

$^1H$ NMR (400 MHz, Chloroform-d) δ 7.48 (d, J=7.9 Hz, 2H), 7.12 (d, J=7.8 Hz, 2H), 7.02 (s, 1H), 4.67 (s, 2H), 3.95 (s, 2H), 3.80 (s, 2H), 2.71 (tt, J=11.3, 3.8 Hz, 1H), 2.40 (t, J=7.6 Hz, 2H), 2.27 (s, 3H), 2.16-2.08 (m, 2H), 1.83-1.76 (m, 2H), 1.58 (tt, J=19.4, 8.2 Hz, 6H), 1.35 (dt, J=7.4, 3.5 Hz, 4H), 1.19 (m, 4H), 0.93-0.89 (t, J=6.8 Hz, 3H). $^{13}C$ NMR (101 MHz, Chloroform-d) δ 154.27, 150.93, 141.05, 139.64, 130.11, 128.94, 123.43, 119.05, 55.20, 47.60, 37.42, 31.67, 30.38, 29.90, 27.74, 25.04, 24.55, 22.49, 20.91, 14.04. HRMS (ESI) calcd for: $C_{25}H_{38}N_3$ $[M+H]^+$ 380.3066, found 380.3069.

N13

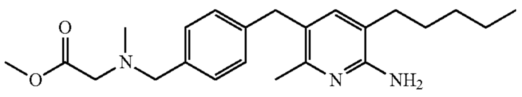

$^1H$ NMR (400 MHz, Chloroform-d) δ 7.25 (d, J=8.0 Hz, 2H), 7.07 (d, J=7.8 Hz, 2H), 7.03 (s, 1H), 4.41 (s, 2H), 3.86 (s, 2H), 3.72 (s, 3H), 3.65 (s, 2H), 3.26 (s, 2H), 2.42-2.37 (m, 5H), 2.31 (s, 3H), 1.63-1.57 (m, 2H), 1.35 (m, 4H), 0.91 (t, J=6.8 Hz, 3H). $^{13}C$ NMR (101 MHz, Chloroform-d) δ 171.49, 154.35, 151.90, 139.56, 139.26, 135.76, 129.25 (2C), 128.41(2C), 124.03, 118.52, 60.91, 57.44, 51.53, 42.40, 37.54, 31.68, 30.50, 27.77, 22.52, 21.44, 14.07. HRMS (ESI) calcd for: $C_{23}H_{34}N_3O_2$ $[M+H]^+$ 384.2651, found 384.2650.

N14

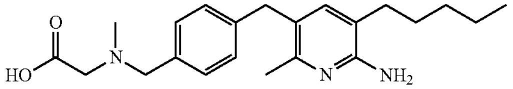

$^1H$ NMR (400 MHz, Methanol-$d_4$) δ 7.49 (d, J=8.0 Hz, 2H), 7.32 (s, 1H), 7.26 (d, J=7.8 Hz, 2H), 4.32 (s, 2H), 3.95 (s, 2H), 3.60 (s, 2H), 2.81 (s, 3H), 2.49 (t, J=7.6 Hz, 2H), 2.31 (s, 3H), 1.60 (m, 2H), 1.36 (m, 4H), 0.92 (m, 3H). $^{13}C$ NMR (101 MHz, Methanol-$d_4$) δ175.10, 154.21,147.57, 142.21, 141.44, 130.96 (2C), 128.89 (2C), 128.23, 122.86, 120.71, 59.20,57.49, 40.05, 36.22, 31.17, 29.31, 27.40, 22.18, 18.02, 13.03. HRMS (ESI) calcd for: $C_{22}H_{32}N_3O_2$ $[M+H]^+$ 370.2495, found 370.2495.

N15

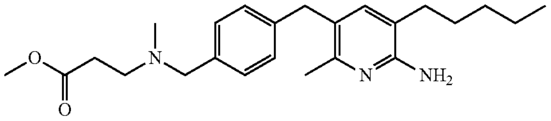

$^1H$ NMR (400 MHz, Chloroform-d) δ 7.20 (d, J=8.0 Hz, 2H), 7.06 (d, J=8.0 Hz, 2H), 7.04 (s, 1H), 4.41 (s, 2H), 3.86 (s, 2H), 3.68 (s, 3H), 3.49 (s, 2H), 2.75 (t, J=7.2 Hz, 2H), 2.53 (t, J=7.2 Hz, 2H), 2.39 (t, J=7.8 Hz, 2H), 2.31 (s, 3H), 2.21 (s, 3H), 1.60 (p, J=7.3 Hz, 2H), 1.35 (dq, J=7.3, 3.8, 3.3 Hz, 4H), 0.91 (t, J=6.8 Hz, 3H). $^{13}C$ NMR (101 MHz, Chloroform-d) δ 173.07, 154.32, 151.86, 139.30, 139.26, 136.39, 129.07(2C), 128.30 (2C), 124.09, 118.54, 61.74, 52.66, 51.61, 41.86, 37.52, 32.67, 31.68, 30.50, 27.78, 22.52, 21.42, 14.07. HRMS (ESI) calcd for: $C_{24}H_{36}N_3O_2$ $[M+H]^+$ 398.2808, found 398.2805.

N16

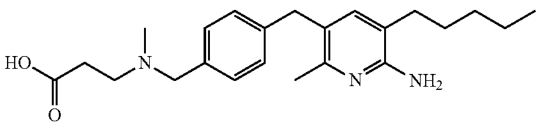

$^1H$ NMR (400 MHz, Methanol-$d_4$) δ 7.41 (d, J=8.2 Hz, 2H), 7.23 (d, J=8.0 Hz, 2H), 7.17 (s, 1H), 4.20 (s, 2H), 3.92 (s, 2H), 3.24 (t, J=6.8 Hz, 2H), 2.69 (s, 3H), 2.57 (t, J=6.8 Hz, 2H), 2.46 (t, J=7.8 Hz, 2H), 2.25 (s, 3H), 1.60 (m, 2H), 1.36 (m, 4H), 0.93 (t, J=6.8 Hz, 3H). $^{13}C$ NMR (101 MHz, Methanol-$d_4$) δ 176.75, 155.07, 150.10, 142.46, 139.98, 130.33 (2C), 128.91 (2C), 128.65, 122.85, 119.42, 59.01, 52.96, 38.28, 36.68, 31.28, 30.03, 29.60, 27.54, 22.30, 19.24, 13.03. m/z:$[M+H]^+$ 384.4.

N17

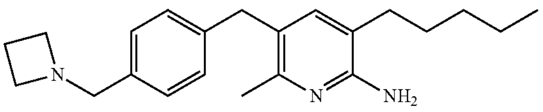

$^1H$ NMR (400 MHz, Methanol-$d_4$) δ 7.27 (d, J=8.0 Hz, 2H), 7.15 (d, J=8.0 Hz, 2H), 7.11 (s, 1H), 3.88 (s, 2H), 3.87 (s, 2H), 3.63 (t, J=7.6 Hz, 4H), 2.44 (t, J=7.7 Hz, 2H), 2.30-2.24 (m, 2H), 2.23 (s, 3H), 1.63-1.55 (m, 2H), 1.36 (tt, J=5.6, 3.1 Hz, 4H), 0.92 (t, J=6.9 Hz, 3H). $^{13}C$ NMR (101 MHz, Methanol-$d_4$) δ 155.13, 150.50, 141.10, 139.66, 131.79, 129.11, 128.53, 123.15, 119.10, 60.49, 54.05, 36.75, 31.30, 29.66, 27.57, 22.22, 19.49, 16.40, 13.06

N18

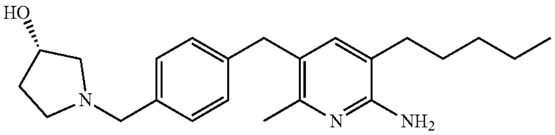

$^1H$ NMR (400 MHz, Chloroform-d) δ 7.26 (d, J=7.8 Hz, 2H), 7.06 (d, J=7.8 Hz, 2H), 7.04 (s, 1H), 4.54 (s, 2H), 4.37 (ddt, J=7.4, 5.0, 2.4 Hz, 1H), 3.85 (s, 2H), 3.68 (m, 3H), 2.96-2.86 (m, 1H), 2.77-2.63 (m, 2H), 2.45 (td, J=9.0, 6.1 Hz, 1H), 2.39 (t, J=7.8 Hz, 2H), 2.20 (dtd, J=15.7, 8.5, 7.8, 5.7 Hz, 1H), 1.85-1.74 (m, 1H), 1.63-1.54 (m, 2H), 1.35 (dp, J=7.4, 4.5, 3.8 Hz, 4H), 0.90 (t, J=6.8 Hz, 3H). $^{13}C$ NMR (101 MHz, Chloroform-d) δ 154.34, 151.48, 139.65, 139.45, 135.24, 129.19, 128.43, 123.85, 118.73, 70.92, 62.64, 59.77, 52.34, 37.47, 34.78, 31.65, 30.43, 27.73, 22.50, 21.22, 14.05.

N19

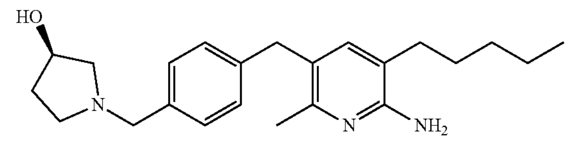

$^{1}$H NMR (400 MHz, Chloroform-d) δ 7.30 (d, J=7.8 Hz, 2H), 7.07 (d, J=7.8 Hz, 2H), 7.06 (s, 1H), 4.71 (s, 2H), 4.40 (ddt, J=7.3, 4.9, 2.3 Hz, 1H), 3.85 (s, 2H), 3.73 (s, 2H), 3.00 (ddd, J=9.7, 8.0, 6.1 Hz, 1H), 2.79 (qd, J=10.6, 3.7 Hz, 2H), 2.57 (td, J=9.1, 5.9 Hz, 1H), 2.40 (t, J=7.7 Hz, 2H), 2.30 (s, 3H), 2.20 (ddd, J=13.5, 8.6, 6.7 Hz, 1H), 1.89-1.80 (m, 1H), 1.63-1.54 (m, 2H), 1.34 (dq, J=7.4, 3.8, 3.3 Hz, 4H), 0.90 (t, J=6.7 Hz, 3H). $^{13}$C NMR (101 MHz, Chloroform-d) δ 154.21, 150.82, 139.88, 139.78, 134.26, 129.42, 128.54, 123.72, 119.09, 70.73, 62.37, 59.66, 52.30, 37.37, 34.61, 31.63, 30.34, 27.69, 22.49, 20.92, 14.05.

N20

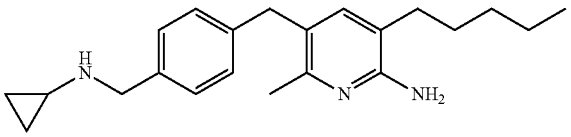

$^{1}$H NMR (400 MHz, Chloroform-d) δ 7.23 (d, J=8.0 Hz, 2H), 7.07 (d, J=7.8 Hz, 2H), 7.03 (s, 1H), 4.39 (s, 2H), 3.86 (s, 2H), 3.82 (s, 2H), 2.39 (d, J=7.6 Hz, 2H), 2.31 (s, 3H), 2.19-2.14 (m, 1H), 1.63-1.55 (m, 2H), 1.35 (dt, J=8.5, 3.2 Hz, 4H), 0.91 (t, J=6.8 Hz, 3H), 0.48-0.38 (m, 4H). $^{13}$C NMR (101 MHz, Chloroform-d) δ 154.36, 151.95, 139.22, 139.11, 138.23, 128.45, 128.31, 124.09, 118.51, 53.40, 37.51, 31.68, 30.52, 30.06, 27.80, 22.51, 21.40, 14.04, 6.44.

N21

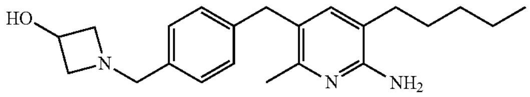

$^{1}$H NMR (400 MHz, Chloroform-d) δ 7.16 (d, J=7.8 Hz, 2H), 7.03 (d, J=7.8 Hz, 2H), 7.01 (s, 1H), 4.45 (m, 3H), 3.81 (s, 2H), 3.68-3.59 (m, 4H), 3.08-2.97 (m, 2H), 2.36 (t, J=7.7 Hz, 2H), 2.25 (s, 3H), 1.62-1.51 (m, 2H), 1.31 (dq, J=7.5, 3.8, 3.4 Hz, 4H), 0.88 (t, J=6.8 Hz, 3H). $^{11}$C NMR (101 MHz, Chloroform-d) δ 154.34, 151.55, 139.67, 139.47, 134.67, 128.80, 128.52, 123.88, 118.72, 63.93, 62.93, 62.06, 37.48, 31.66, 30.43, 27.74, 22.50, 21.22, 14.05.

N22

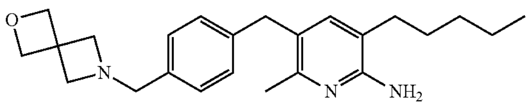

$^{1}$H NMR (400 MHz, Chloroform-d) δ 7.15 (d, J=8.1 Hz, 2H), 7.05 (d, J=7.9 Hz, 2H), 7.02 (s, 1H), 4.75 (s, 4H), 4.39 (s, 2H), 3.85 (s, 2H), 3.51 (s, 2H), 3.38 (s, 4H), 2.40 (t, J=7.6 Hz, 2H), 2.30 (s, 3H), 1.63-1.55 (m, 2H), 1.35 (dq, J=7.5, 3.8, 3.4 Hz, 4H), 0.91 (t, J=6.8 Hz, 3H). $^{13}$C NMR (101 MHz, Chloroform-d) δ 154.33, 151.89, 139.45, 139.27, 135.41, 128.54, 128.47, 124.00, 118.53, 81.41, 63.68, 63.24, 39.06, 37.51, 31.67, 30.50, 27.78, 22.51, 21.42, 14.05.

N23

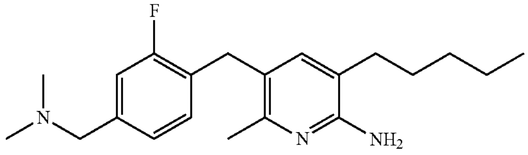

$^{1}$H NMR (400 MHz, Chloroform-d) δ 7.05-6.86 (m, 4H), 4.36 (s, 2H), 3.83 (s, 2H), 3.37 (s, 2H), 2.37 (t, J=7.7 Hz, 2H), 2.31 (s, 3H), 2.23 (s, 6H), 1.58 (q, J=7.3 Hz, 2H), 1.38-1.28 (m, 4H), 0.89 (t, J=6.5 Hz, 3H). $^{13}$C NMR (101 MHz, Chloroform-d) δ 160.89 (J=243.7 Hz),154.46, 151.97, 139.27 (J=7.2 Hz), 139.09, 129.98(J=4.9 Hz), 126.01 (J=15.8 Hz),124.48 (J=3.1 Hz), 122.73, 118.53, 115.62 (J=22.1 Hz), 63.59, 45.33, 31.63, 30.52 (J=3.0 Hz), 30.47, 27.71, 22.49, 21.32, 14.03.

N24

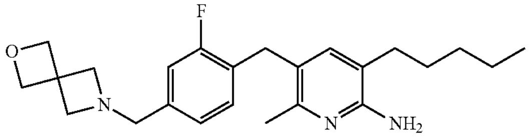

$^{1}$H NMR (400 MHz, Chloroform-d) δ 7.01 (s, 1H), 6.94 (d, J=11.2 Hz, 1H), 6.91-6.84 (m, 2H), 4.74 (s, 4H), 4.44 (s, 2H), 3.82 (s, 2H), 3.48 (s, 2H), 3.36 (s, 4H), 2.37 (t, J=7.7 Hz, 2H), 2.30 (s, 3H), 1.58 (q, J=7.5 Hz, 2H), 1.31 (m, 4H), 0.89 (t, J=6.9 Hz, 3H). $^{11}$C NMR (101 MHz, Chloroform-d) 6160.89 (J=244.0 Hz), 154.46, 151.81, 139.18, 138.13 (J=7.3 Hz), 130.12 (J=5.1 Hz), 126.12 (J=14.8 Hz),123.82 (J=2.9 Hz), 122.54, 118.59, 115.0 (J=22.2 Hz), 81.32, 63.71, 62.7 (J=1.4 Hz), 39.05, 31.62, 30.47, 30.44, 27.70, 22.50, 21.22 14.04.

N25

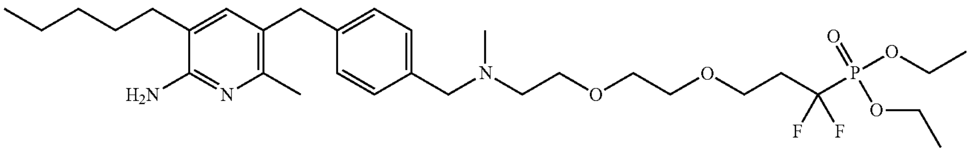

$^1$H NMR (400 MHz, Chloroform-d) δ 7.24 (d, J=7.8 Hz, 2H), 7.06 (s, 1H), 7.05 (d, J=7.8 Hz, 2H), 4.62 (s, 2H), 4.28 (p, J=7.3 Hz, 4H), 3.85 (s, 2H), 3.76 (t, J=7.2 Hz, 2H), 3.63 (m, 6H), 3.57 (s, 2H), 2.66 (t, J=6.0 Hz, 2H), 2.42 (m, 4H), 2.32 (s, 3H), 2.28 (s, 3H), 1.64-1.54 (m, 2H), 1.42-1.32 (m, 10H), 0.91 (t, J=6.5 Hz, 3H). $^{19}$F NMR (376 MHz, Chloroform-d) δ-111.00 (t, J=19.7 Hz), -111.28 (t, J=19.7 Hz). $^{31}$P NMR (162 MHz, Chloroform-d) δ 7.41-7.06 (p, J=7.4 Hz), 6.61 (p, J=7.4 Hz), 5.94 (p, J=7.3 Hz). $^{13}$C NMR (101 MHz, Chloroform-d) 6154.1, 151.06, 139.67, 139.18, 136.02, 129.37, 128.30, 124.03, 121.00,118.95, 118.87, 118.41, 70.45, 70.25, 69.39, 64.54, 64.47, 63.79 (q, J=6.1 Hz),62.23, 56.21, 42.62, 37.38, 34.35 (td, J=20.5, 14.3 Hz),31.63, 30.38, 27.71, 22.49, 20.97, 16.42, 16.37, 14.03. m/z:$[M+H]^+$ 614.5.

N26

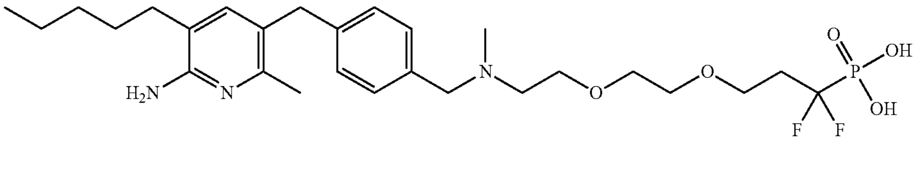

$^1$H NMR (400 MHz, Deuterium Oxide) 6 8.28 (s, 1H), 7.42 (s, 1H), 7.28 (d, J=7.9 Hz, 2H), 7.14 (d, J=7.8 Hz, 2H), 4.18 (s, 2H), 3.76 (s, 2H), 3.57 (t, J=6.5 Hz, 4H), 3.35 (m, 4H), 3.18 (m, 2H), 2.73 (s, 3H), 2.31 (t, J=7.5 Hz, 2H), 2.22 (s, 3H), 2.19-2.06 (m, 2H), 1.39 (q, J=7.4 Hz, 2H), 1.09 (dq, J=8.1, 4.6, 3.3 Hz, 4H), 0.66 (t, J=6.8 Hz, 3H). $^{13}$C NMR (101 MHz, Deuterium Oxide) 6 151.45, 146.70, 146.07, 144.76, 141.84, 141.64, 131.29, 129.11, 127.21, 123.28, 123.21, 69.19, 69.10, 64.27 (m), 63.50, 59.84, 53.99, 40.28, 35.10, 33.24 (td, J=21.0, 17.9 Hz), 30.28, 28.33, 26.19, 21.69, 15.83, 13.20. $^{19}$F NMR (376 MHz, Deuterium Oxide) δ-111.80 (t, J=20.0 Hz),-112.03 (t, J=20.2 Hz). $^{31}$P NMR (162 MHz, Deuterium Oxide) 6 5.42(m), 4.90(m), 4.34(m). m/z:$[M+H]^+$ 558.4.

Example 13: Preparation Method of Compound N27

Compound 16a prepared in Example 7 was used as a raw material. Compound 16a (94.85 mg, 0.3 mmol) was dissolved in 5 mL of dry methanol. Potassium carbonate (82.93 mg, 0.6 mmol) was added. The reaction liquid was stirred at 65° C. for 5 h. After the reaction was completed, the reaction liquid was filtered, and the filtrate was dried over anhydrous sodium sulfate, concentrated under reduced pressure, and purified by silica gel column chromatography (DCM: MeOH=20:1) to obtain a white solid N27, the reaction formula-being as follows:

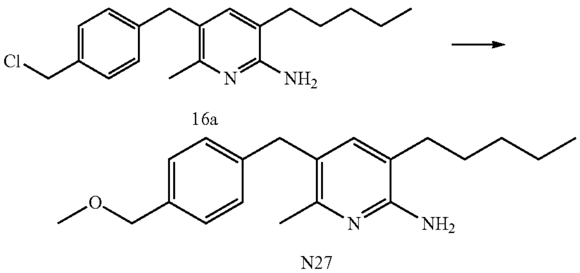

16a

N27

$^1$H NMR (400 MHz, Chloroform-d) δ 7.23 (d, J=7.9 Hz, 2H), 7.08 (d, J=7.8 Hz, 2H), 7.00 (s, 1H), 4.41 (s, 2H), 4.37 (s, 2H), 3.85 (s, 2H), 3.37 (s, 3H), 2.37 (t, J=7.8 Hz 2H), 2.28 (s, 3H), 1.60-1.53 (m, 2H), 1.32 (m, 4H), 0.91-0.86 (t, J=6.8 Hz, 3H). $^{13}$C NMR (101 MHz, Chloroform-d) δ 154.41, 152.04, 140.05, 139.19, 135.83, 128.48, 127.97, 123.95, 118.49, 74.53, 58.07, 37.58, 31.69, 30.54, 27.81, 22.52, 21.46, 14.05. HRMS (ESI) calcd for: $C_{20}H_{28}N_2O$ $[M+H]^+$ 313.2280, found 313.2280.

Example 14: Preparation Method of Compounds N28-N30

Compounds N28-N30 were obtained by replacing the reactant 16a with compound 16b according to the synthesis method of compound N4 in Example 10;

N28

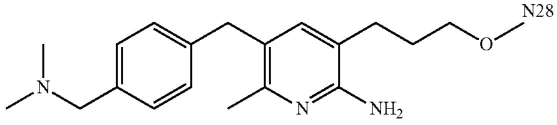

$^1$H NMR (400 MHz, Chloroform-d) δ 7.24 (d, J=7.9 Hz, 2H), 7.07 (d, J=8.0 Hz, 2H), 7.06 (s, 1H), 4.95 (s, 2H), 3.85 (s, 2H), 3.45 (s, 2H), 3.38 (t, J=5.8 Hz, 2H), 3.36 (s, 3H), 2.52 (t, J=7.4 Hz, 2H), 2.33 (s, 3H), 2.28 (s, 6H), 1.88-1.81 (m, 2H). $^{13}$C NMR (101 MHz, Chloroform-d) δ 154.69, 151.3, 140.18, 139.29, 135.9, 129.42, 128.40, 123.79, 118.25, 71.00, 63.81, 58.56, 45.10, 37.31, 28.77, 26.48, 20.94. HRMS (ESI) calcd for: $C_{20}H_{30}N_3O$ $[M+H]^+$ 328.2389, found 328.2388.

N29

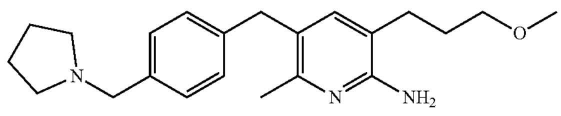

N30

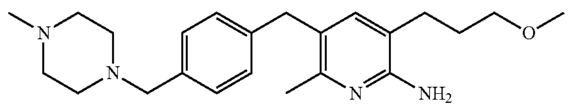

$^1$H NMR (400 MHz, Chloroform-d) δ 7.23 (d, J=7.9 Hz, 2H), 7.08-7.03 (m, 3H), 4.70 (s, 2H), 3.85 (s, 2H), 3.51 (s, 2H), 3.39 (t, J=5.9 Hz, 2H), 3.36 (s, 3H), 2.65-2.30 (m, 16H), 1.88-1.82 (m, 2H). $^{13}$C NMR (101 MHz, Chloroform-d) δ 154.81, 151.96, 139.85, 139.29, 135.61, 129.35, 128.32, 123.93, 117.92, 71.07, 62.57, 58.55, 55.05, 52.73, 45.88, 37.43, 28.81, 26.56, 21.35. HRMS (ESI) calcd for: $C_{23}H_{35}N40$ $[M+H]^+$ 383.2811, found 383.2801.

Example 15: Preparation Method of Compound N31

Compound N31 was obtained according to the synthesis method of compound N4 in Example 10:

N31

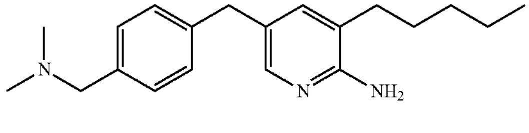

$^1$H NMR (400 MHz, Chloroform-d) δ 7.83 (s, 1H), 7.23 (d, J=8.0 Hz, 2H), 7.13 (d, J=8.0 Hz, 2H), 7.09 (s, 1H), 4.36 (s, 2H), 3.84 (s, 2H), 3.40 (s, 2H), 2.38 (t, J=7.6 Hz, 2H), 2.24 (s, 6H), 1.63-1.56 (m, 2H), 1.35 (m, 4H), 0.90 (t, J=6.8 Hz, 3H). $^{13}$C NMR (101 MHz, Chloroform-d) δ 155.12, 145.15, 139.98, 137.59, 136.50, 129.28, 128.53, 126.98, 121.06, 64.03, 45.31, 37.93, 31.68, 30.95, 27.55, 22.49, 14.02. HRMS (ESI) calcd for: $C_{20}H_{30}N_3$ $[M+H]^+$ 312.2440, found 312.2434.

Example 16: Preparation Method of Compound N32

Compound N32 was obtained according to the synthesis method of compound N4 in Example 10:

N32

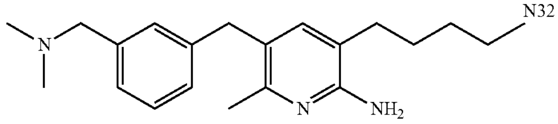 [SMILES: CCCCCc1cc(Cc2cccc(CN(C)C)c2)c(C)nc1N]

$^1$H NMR (400 MHz, Chloroform-d) δ 7.22 (t, J=7.5 Hz, 1H), 7.13 (dt, J=7.7, 1.4 Hz, 1H), 7.08 (s, 1H), 7.02 (s, 1H), 6.96 (dt, J=7.5, 1.5 Hz, 1H), 4.90 (s, 2H), 3.84 (s, 2H), 3.39 (s, 2H), 2.39-2.34 (t, J=7.8, 2H), 2.30 (s, 3H), 2.23 (s, 6H), 1.56 (m, 2H), 1.32 (m, 4H), 0.91-0.86 (t, J=6.8 Hz, 3H). $^{13}$C NMR (101 MHz, Chloroform-d) δ 154.36, 150.95, 140.35, 139.65, 138.70, 129.35, 128.37, 127.23, 127.01, 123.77, 118.88, 64.18, 45.19, 37.59, 31.62, 30.36, 27.66, 22.49, 20.67, 14.02. HRMS (ESI) calcd for: $C_{21}H_{32}N_3[M+H]^+$ 326.2596, found 326.2589.

Example 17: Preparation Method of Compound N33

Compound N33 was obtained according to the synthesis method of compound 14a in Example 7, the reaction formula being as follows:

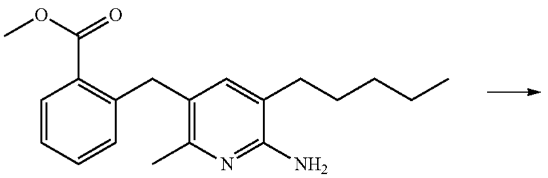

-continued

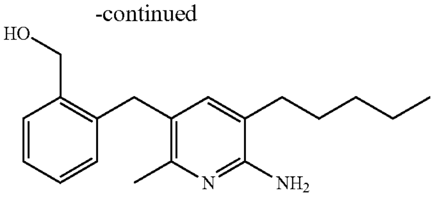

N33

$^1$H NMR (400 MHz, Chloroform-d) δ 7.45 (dd, J=7.1, 1.8 Hz, 1H), 7.24 (m, 2H), 6.94 (dd, J=7.2, 1.7 Hz, 1H), 6.86 (s, 1H), 4.73 (s, 2H), 4.33 (s, 2H), 3.94 (s, 2H), 2.35 (t, J=7.7 Hz, 2H), 2.29 (s, 3H), 1.58-1.50 (m, 2H), 1.30 (m, 4H), 0.89 (t, J=6.8 Hz, 3H). $^{13}$C NMR (101 MHz, Chloroform-d) δ 154.43, 152.14, 138.76, 138.72, 138.26, 129.25, 128.01, 127.95, 126.50, 123.24, 118.54, 63.14, 34.09, 31.64, 30.51, 27.74, 22.50, 21.42, 14.06. HRMS (ESI) calcd for $C_{19}H_{27}N20$ $[M+H]^+$ 299.2123, found 299.2119.

Example 18: Preparation Method of Compounds N34-N36

Compounds N34-N36 were obtained according to the synthesis method of compound N4 in Example 10:

N34

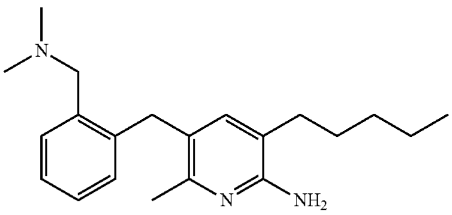

$^1$H NMR (400 MHz, Chloroform-d) δ 7.33-7.29 (m, 1H), 7.23-7.15 (m, 2H), 6.94-6.89 (m, 1H), 6.84 (s, 1H), 4.33 (s, 2H), 4.01 (s, 2H), 3.38 (s, 2H), 2.36 (d, J=7.6 Hz, 2H), 2.33 (s, 3H), 2.24 (s, 6H), 1.59-1.50 (m, 2H), 1.34-1.27 (m, 4H), 0.89 (t, J=6.8 Hz, 3H). $^{13}$C NMR (101 MHz, Chloroform-d) δ 154.20, 152.16, 139.51, 138.77, 137.06, 130.22, 129.26, 127.26, 125.90, 123.98, 118.34, 62.17, 45.58, 34.13, 31.61, 30.53, 27.78, 22.49, 21.45, 14.03. HRMS (ESI) calcd for: $C_{21}H_{32}N_3[M+H]^+$ 326.2596, found 326.2589.

N35

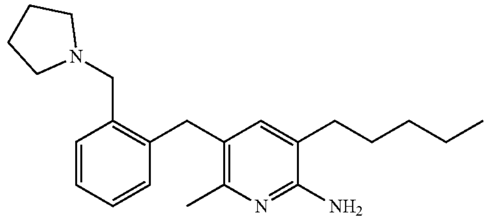

$^1$H NMR (400 MHz, Chloroform-d) δ 7.38-7.34 (m, 1H), 7.18 (tt, J=7.4, 5.5 Hz, 2H), 6.92 (dd, J=7.2, 1.9 Hz, 1H), 6.85 (s, 1H), 4.31 (s, 2H), 4.02 (s, 2H), 3.59 (s, 2H), 2.50 (m, 4H), 2.34 (t, J=7.6 Hz, 2H), 2.32 (s, 2H), 1.78 (m, 4H), 1.60-1.51 (m, 2H), 1.36-1.29 (m, 4H), 0.89 (t, J=6.8 Hz, 3H). $^{13}$C NMR (101 MHz, Chloroform-d) δ 154.19, 152.23, 139.11, 138.76, 137.73, 129.57, 129.12, 127.00, 125.93, 124.05, 118.29, 58.30, 54.29, 34.15, 31.64, 30.57, 27.83, 23.60, 22.50, 21.44, 14.03. m/z:$[M+H]^+$ 352.4.

N36

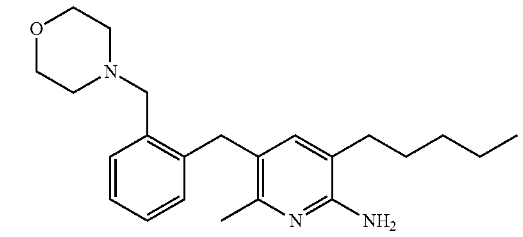

$^1$H NMR (400 MHz, Chloroform-d) δ 7.28 (m, 1H), 7.22-7.16 (m, 2H), 6.95-6.89 (m, 1H), 6.86 (s, 1H), 4.34 (s, 2H), 4.05 (s, 2H), 3.68 (t, J=4.8 Hz, 4H), 3.47 (s, 2H), 2.47-2.40 (t, J=4.8 Hz, 4H), 2.39-2.35 (t, J=7.6 Hz, 2H), 2.31 (s, 3H), 1.60-1.51 (m, 2H), 1.32 (m, 4H), 0.92-0.87 (t, J=6.8 Hz, 3H). $^{13}$C NMR (101 MHz, Chloroform-d) δ 154.30, 152.24, 139.94, 138.82, 135.67, 130.50, 129.28, 127.51, 125.79, 123.78, 118.32, 67.11, 61.56, 53.69, 34.19, 31.65, 30.57, 27.83, 22.52, 21.51, 14.07. HRMS (ESI) calcd for: $C_{23}H_{34}N_3O$ $[M+H]^+$ 368.2702, found 368.2700.

Example 19: Preparation Method of Compound N37

Compound N37 was obtained according to the synthesis method of compound N5 in Example 11:

N37

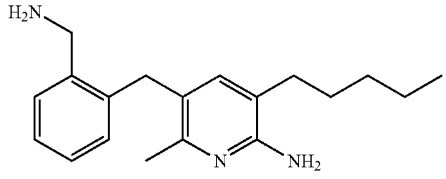

Example 20: Preparation Method of Compound N38, Including the Steps as Follows (1) Compound 12a (326.20 mg, 1 mmol) was dissolved in 3 mL of a mixed solvent ($THF:H_2O$=2:1), and lithium hydroxide monohydrate (125.88 mg, 3 mmol) was added. The reaction liquid was reacted at room temperature overnight and concentrated by rotary evaporation to remove the organic solvent. 2 M HCl was added dropwise in an ice bath to adjust the pH to 5-6. The reaction liquid was extracted three times with ethyl acetate/water. The organic phases were combined and dried over $MgSO_4$, concentrated under reduced pressure, and dried in vacuum to obtain a light yellow solid, i.e., compound 23, the reaction formula being as follows:

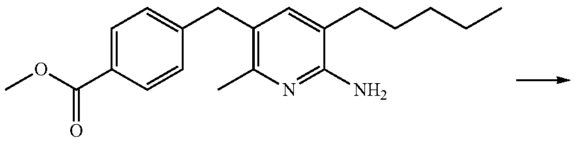

12a

-continued

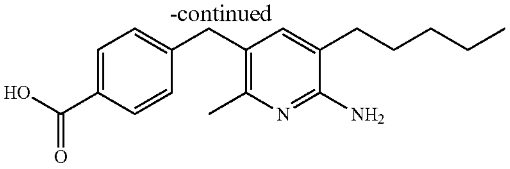

23

(2) Compound 23 (78.05 mg, 0.25 mmol) was dissolved in 2 mL of DMF, and HATU (142.59 mg, 0.38 mmol), DIEA (87.1 μL, 0.5 mmol), and dimethylamine (0.375 mL, 2 M in methanol) were added in sequence. The reaction liquid was reacted at room temperature for 2 h. After the reaction was completed, the reaction liquid was extracted three times with ethyl acetate/water. The organic phases were combined, dried over anhydrous sodium sulfate, concentrated under reduced pressure, and purified by silica gel column chromatography (DCM:MeOH=20:1) to obtain a light yellow solid N38, the reaction formula being as follows:

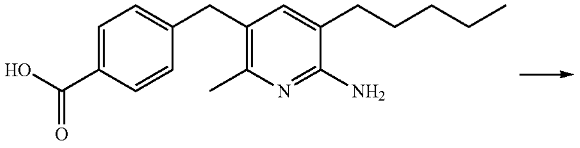

23

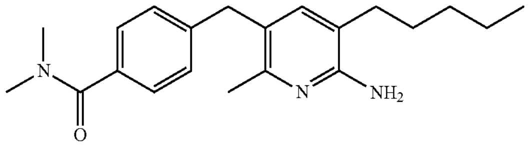

N38

$^1$H NMR (400 MHz, Chloroform-d) δ 7.32 (d, J=7.8 Hz, 2H), 7.12 (d, J=7.8 Hz, 2H), 6.99 (s, 1H), 4.32 (s, 2H), 3.87 (s, 2H), 3.09 (s, 3H), 2.97 (s, 3H), 2.37 (t, J=7.8 Hz, 2H), 2.27 (s, 3H), 1.57 (m, 2H), 1.33 (m, 4H), 0.88 (d, J=6.8 Hz, 3H). $^{13}$C NMR (101 MHz, Chloroform-d) δ 171.6, 154.6, 152.2, 142.3, 139.1, 134.0, 128.4, 127.3, 123.4, 118.5, 39.6, 37.7, 35.4, 31.7, 30.6, 27.8, 22.5, 21.6, 14.03. HRMS (ESI) calcd for: $C_{21}H_{30}N_30$ $[M+H]^+$ 340.2389, found 340.2394.

Example 21: Preparation Method of Compounds N39-N41

Compounds N39-N41 were obtained by replacing the reactant dimethylamine with tetrahydropyrrole, morpholine, and N-methylpiperazine according to the synthesis method of compound N38 in Example 20:

N39

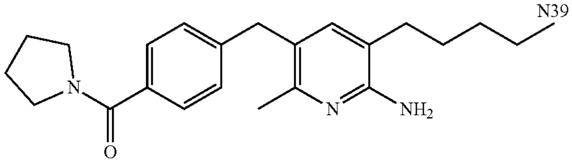 [SMILES: CCCCCc1cc(Cc2ccc(C(=O)N3CCCC3)cc2)c(C)nc1N]

$^1$H NMR (400 MHz, Chloroform-d) δ 7.42 (d, J=8.0 Hz, 2H), 7.11 (d, J=8.0 Hz, 2H), 6.99 (s, 1H), 4.39 (s, 2H), 3.87 (s, 2H), 3.63 (t, J=6.8 Hz, 2H), 3.41 (t, J=6.6 Hz, 2H), 2.37 (t, J=7.8 Hz, 2H), 2.26 (s, 3H), 1.94 (m, 2H), 1.85 (m, 2H), 1.57 (td, J=13.0, 10.5, 7.2 Hz, 2H), 1.33 (dq, J=7.2, 3.8, 3.3 Hz, 4H), 0.88 (t, J=6.8 Hz, 3H). $^{13}C$ NMR (101 MHz, Chloroform-d) δ 169.66, 154.53, 151.98, 142.51, 139.21, 134.95, 128.26, 127.36, 123.41, 118.61, 49.64, 46.19, 37.73, 31.69, 30.52, 27.80, 26.41, 24.45, 22.50, 21.42, 14.04. HRMS (ESI) calcd for: $C_{23}H_{32}N_3O$ $[M+H]^+$ 366.2545, found 366.2547.

N40

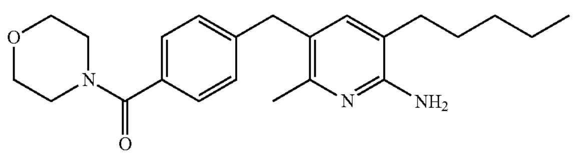

m/z:$[M+H]^+$ 382.3.

N41

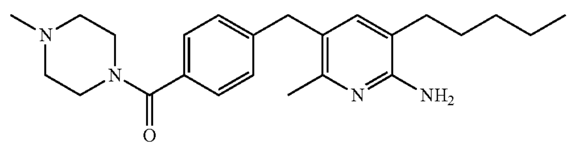

$^1H$ NMR (400 MHz, Chloroform-d) δ 7.33 (d, J=7.8 Hz, 2H), 7.15 (d, J=7.8 Hz, 2H), 7.02 (s, 2H), 4.37 (s, 2H), 3.89 (s, 2H), 3.80 (br, 2H), 3.46 (br, 2H), 2.54-2.21 (m, 12H), 1.60 (dqd, J=12.1, 5.9, 4.7, 2.2 Hz, 2H), 1.35 (dq, J=7.2, 3.7, 3.2 Hz, 4H), 0.90 (t, J=6.8 Hz, 3H). $^{13}C$ NMR (101 MHz, Chloroform-d) δ 170.3, 154.59, 152.2, 142.51, 139.12, 133.5, 128.46, 127.31, 123.33, 118.54, 56.2, 54.7, 47.7, 46.05, 42.2, 37.74, 31.69, 30.55, 27.81, 22.50, 21.54, 14.05. m/z:$[M+H]^+$ 394.5.

Example 22: Preparation Method of Compound 25, Including the Steps as Follows (1) Under nitrogen atmosphere, methyl 3-methoxy-4-bromomethylbenzoate (1360.28 mg, 5.25 mmol) was dissolved in 15 mL of dry tetrahydrofuran, and zinc powder (686.6 mg, 10.5 mmol) was added. The reaction liquid was stirred at 0° C. for 5 h. After the reaction was completed, the reaction liquid was filtered to obtain zinc reagent. Compound 9 (900.11 mg, 3.5 mmol) was taken, and bis(dibenzylideneacetone)palladium (40.25 mg, 0.07 mmol), Q-Phos (49.7 mg, 0.07 mmol), and zinc reagent were added in sequence. The reaction liquid was heated to 80° C. and stirred for 3 h. After the reaction was completed, the reaction liquid was cooled to room temperature and filtered. The filtrate was dried over anhydrous sodium sulfate, concentrated under reduced pressure, and purified by silica gel column chromatography (DCM:MeOH=20:1) to obtain compound 24, the reaction formula being as follows:

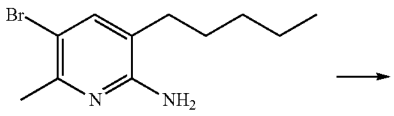

-continued

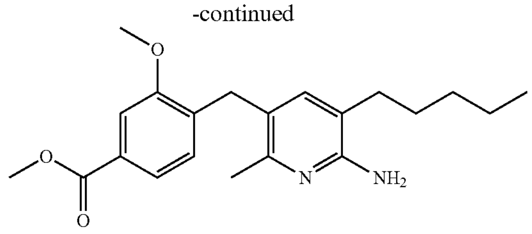

24

(2) Compound 24 (534.3 mg, 1.5 mmol) was dissolved in 10 mL of dry tetrahydrofuran and cooled to 0° C. Lithium aluminum hydride (114.0 mg, 3.0 mmol) was slowly added in batches. The mixture was successively stirred at 0° C. for 1.0 h. After the reaction was completed, 114 μL of water, 114 μL of 10% aqueous NaOH solution, and 342 μL of water were added to the reaction liquid in sequence to quench the reaction. Sonication was performed for 10 min, and then the reaction liquid was filtered. The filter residue was washed with acetone, and the filtrate was dried over anhydrous sodium sulfate, concentrated under reduced pressure, and purified by silica gel column chromatography (DCM:MeOH=15:1) to obtain compound 25, the reaction formula being as follows:

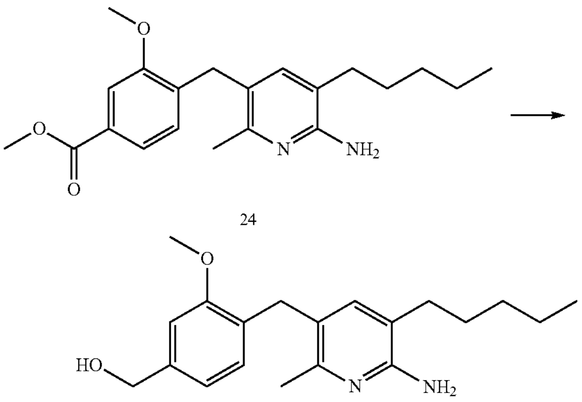

24

25

$^1H$ NMR (400 MHz, Chloroform-d) δ 7.01 (s, 1H), 6.95 (s, 1H), 6.83 (d, J=8 Hz, 2H), 6.90 (d, J=8 Hz, 2H), 4.69 (s, 2H), 4.41 (s, 2H), 3.84 (s, 3H), 3.65 (s, 2H), 2.36 (t, J=7.7 Hz, 2H), 2.26 (s, 3H), 1.59 (m, 2H), 1.34 (m, 4H), 0.91 (t, J=6.8 Hz, 3H). $^{13}C$ NMR (101 MHz, Chloroform-d) δ 157.43, 154.24, 151.88, 140.70, 139.43, 129.27, 127.99, 123.52, 118.78, 118.50, 108.86, 64.88, 55.27, 31.65, 31.58, 30.45, 27.77, 22.52, 21.04, 14.04. m/z:$[M+H]^+$ 329.4.

Example 23: Preparation Method of Compound 26

Compound 25 (328.22 mg, 1 mmol) was dissolved in 5 mL of dry dichloromethane, and thionyl chloride (108.9 μL, 1.5 mmol) was slowly added dropwise. The reaction liquid was stirred at room temperature for 0.5 h. After the reaction was completed, the reaction liquid was concentrated under reduced pressure and dried to obtain a yellow solid 26, which was used directly without purification, the reaction formula being as follows:

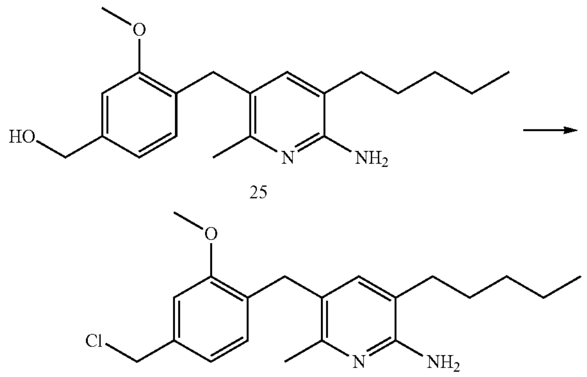

25

26

Example 24: Preparation Method of Compound N42

Compound 26 prepared in Example 23 was used as a raw material. Compound 26 (103.85 mg, 0.3 mmol) was dissolved in 5 mL of dry methanol. Dimethylamine (0.450 mL, 2 M in methanol) and potassium carbonate (82.93 mg, 0.6 mmol) were added in sequence. The reaction liquid was stirred at 45° C. for 3 h. After the reaction was completed, the reaction liquid was filtered, and the filtrate was dried over anhydrous sodium sulfate, concentrated under reduced pressure, and purified by silica gel column chromatography (DCM:MeOH=10:1) to obtain a white solid N42, the reaction formula being as follows:

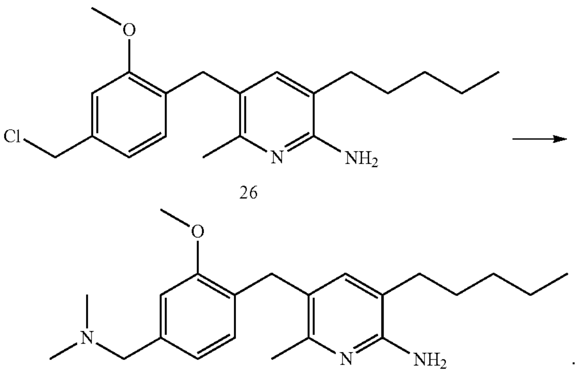

26

N42

$^1$H NMR (400 MHz, Chloroform-d) δ 7.00 (s, 1H), 6.88 (s, 1H), 6.81 (d, J=7.6 Hz, 1H), 6.76 (d, J=7.7 Hz, 1H), 4.33 (s, 2H), 3.86 (s, 3H), 3.81 (s, 2H), 3.40 (s, 2H), 2.37 (t, J=7.7 Hz, 2H), 2.32 (s, 3H), 2.26 (s, 6H), 1.62-1.53 (m, 2H), 1.33 (dq, J=7.7, 3.9, 3.4 Hz, 4H), 0.90 (t, J=6.8 Hz, 3H). $^{13}$C NMR (101 MHz, Chloroform-d) δ 157.34, 154.18, 152.17, 139.22, 138.18, 129.06, 127.69, 123.77, 121.04, 118.29, 110.69, 64.49, 55.34, 45.44, 31.64, 31.63, 30.50, 27.78, 22.52, 21.37, 14.03. HRMS (ESI) calcd for $C_{22}H_{34}N_3O$ [M+H]$^+$ 356.2702, found 356.2696.

Example 25: Preparation Method of Compounds N43-N45

Compounds N43-N45 were obtained by replacing the raw material dimethylamine with tetrahydropyrrole, morpholine, or N-methylpiperazine according to the synthesis method of compound N42 in Example 24:

N43

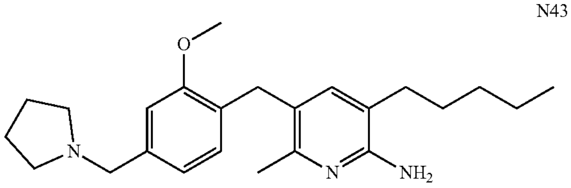 [SMILES: CCCCCc1cc(Cc2ccc(CN3CCCC3)cc2OC)c(C)nc1N]

$^1$H NMR (400 MHz, Chloroform-d) δ 7.01 (s, 1H), 6.93 (s, 1H), 6.80 (m, 2H), 4.37 (s, 2H), 3.86 (s, 3H), 3.80 (s, 2H), 3.63 (s, 2H), 2.56 (td, J=5.1, 4.3, 2.3 Hz, 4H), 2.40-2.35 (t, J=7.6 Hz, 2H), 2.32 (s, 3H), 1.82 (m, 4H), 1.58 (m, 2H), 1.33 (m, 4H), 0.94-0.87 (t, J=6.8 Hz, 3H). $^{13}$C NMR (101 MHz, Chloroform-d) δ 157.30, 154.16, 152.1, 139.30, 138.24, 129.07, 127.58, 123.75, 120.85, 118.35, 110.77, 60.73, 55.38, 54.17, 31.64, 31.60, 30.49, 27.77, 23.43, 22.52, 21.29, 14.03. m/z:[M+H]$^+$ 382.5.

N44

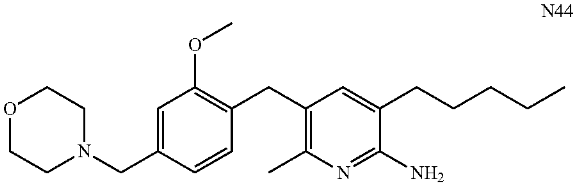 [SMILES: CCCCCc1cc(Cc2ccc(CN3CCOCC3)cc2OC)c(C)nc1N]

m/z:[M+H]$^+$ 398.3.

N45

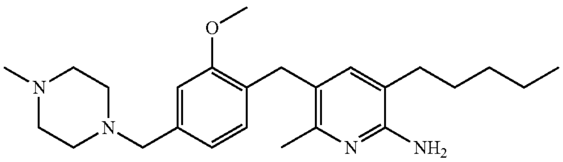

$^1$H NMR (400 MHz, Chloroform-d) δ 7.04 (s, 1H), 6.87 (s, 1H), 6.82-6.76 (m, 2H), 4.65 (s, 2H), 3.85 (s, 3H), 3.79 (s, 2H), 3.49 (s, 2H), 2.64-2.29 (m, 16H), 1.57 (m, 2H), 1.36-1.29 (m, 4H), 0.91-0.87 (t, J=6.8 Hz, 3H). $^{13}$C NMR (101 MHz, Chloroform-d) δ 157.25, 153.96, 151.1, 139.79, 137.47, 129.07, 127.42, 123.64, 121.12, 118.72, 110.88, 62.94, 55.33, 55.06, 52.92, 45.94, 31.59, 31.53, 30.33, 27.67, 22.50, 20.82, 14.03. HRMS (ESI) calcd for $C_{25}H_{39}N40$ [M+H]$^+$ 411.3124, found 411.3115.

Example 26: Preparation Method of Compound N46

Compound N42 (35.53 mg, 0.1 mmol) was dissolved in 2 mL of dry dichloromethane and cooled to 0° C. Boron tribromide (47.27 μL, 0.5 mmol) was slowly added dropwise. After the addition was completed, the reaction liquid was heated to room temperature and stirred for 3 h. After the reaction was completed, excessive methanol was added in an ice bath to quench the reaction. The reaction liquid was concentrated under reduced pressure and purified by silica gel column chromatography (DCM:MeOH=5:1) to obtain compound N46, the reaction formula being as follows:

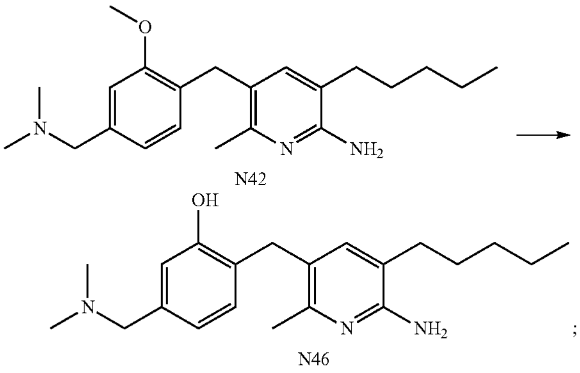

N42 N46 ;

$^1$H NMR (400 MHz, Methanol-$d_4$) δ 7.59 (s, 1H), 7.19 (d, J=7.6 Hz, 1H), 7.00 (d, J=1.7 Hz, 1H), 6.97 (dd, J=7.6, 1.8 Hz, 1H), 4.25 (s, 2H), 3.90 (s, 2H), 2.85 (s, 6H), 2.53 (t, J=7.6 Hz, 2H), 2.50 (s, 3H), 1.60 (m, 2H), 1.39-1.33 (m, 4H), 0.91 (d, J=7.0 Hz, 3H). $^{13}$C NMR (101 MHz, Methanol-$d_4$) δ 155.8, 152.0, 144.44, 142.3, 130.67, 129.6, 127.6, 123.3, 122.7, 121.59, 116.90, 60.59, 41.61, 30.89, 30.1, 28.63, 27.09, 22.11, 15.7, 14.0. HRMS (ESI) calcd for $C_{21}H_{32}N_3O$ [M+H]$^+$ 342.2545, found 342.2544.

Example 27: Preparation Method of Compounds N47-N50

Compounds N47-N49 were obtained by replacing compound N42 with N43, N44 or N45 according to the synthesis method of compound N46 in Example 26:

N47

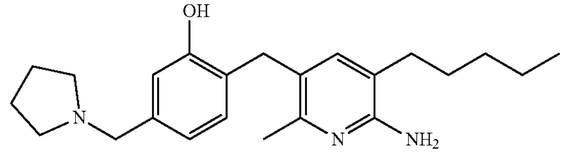

$^1$H NMR (400 MHz, Methanol-$d_4$) δ 7.28 (s, 1H), 7.01 (d, J=7.7 Hz, 1H), 6.96 (d, J=1.7 Hz, 1H), 6.90 (dd, J=7.7, 1.8 Hz, 1H), 4.21 (s, 2H), 3.85 (s, 2H), 3.30-3.20 (t, J=6.4 Hz, 4H), 2.46 (t, J=7.6 Hz, 2H), 2.35 (s, 3H), 2.07 (dq, J=10.2, 6.7, 5.1 Hz, 4H), 1.59 (m, 2H), 1.36 (m, 4H), 0.92 (t, J=6.8 Hz, 3H). $^{13}$C NMR (101 MHz, Methanol-$d_4$) δ 155.62, 153.89, 147.62, 141.31, 130.21, 128.25, 127.09, 122.98, 120.80, 120.25, 116.15, 57.93, 53.39, 31.13, 30.55, 29.28, 27.39, 22.38, 22.17, 18.05, 12.99. HRMS (ESI) calcd for $C_{23}H_{34}N_3O$ [M+H]$^+$ 368.2702, found 368.2702.

N48

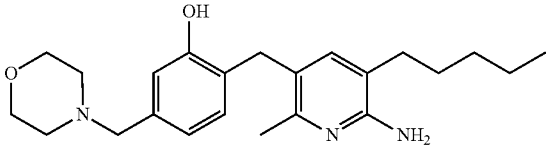

$^1$H NMR (400 MHz, Methanol-$d_4$) δ 7.36 (s, 1H), 7.01 (d, J=7.6 Hz, 1H), 6.92 (d, J=1.8 Hz, 1H), 6.88 (d, J=7.6 Hz, 1H), 4.09 (s, 2H), 3.77 (s, 2H), 3.73 (t, J=4.9 Hz, 4H), 2.43 (t, J=4.8 Hz, 4H), 2.40 (t, J=7.6 Hz, 2H), 2.38 (s, 3H), 1.65-1.59 (m, 2H), 1.41-1.36 (m, 4H), 0.91 (t, J=6.7 Hz, 3H). m/z: [M+H]$^+$ 384.3.

N49

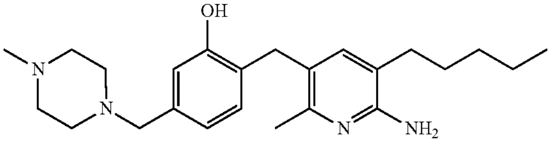

$^1$H NMR (400 MHz, Methanol-$d_4$) δ 7.58 (s, 1H), 7.03 (d, J=7.6 Hz, 1H), 6.87 (s, 1H), 6.83-6.79 (d, J=7.6 Hz, 1H), 3.83 (s, 2H), 3.61 (s, 2H), 3.21 (m, 4H), 2.81 (s, 7H), 2.51 (m, 6H), 1.57 (m, 2H), 1.34 (m, 4H), 0.91 (t, J=6.7 Hz, 3H). $^{13}$C NMR (101 MHz, Methanol-$d_4$) δ 155.2, 152.0, 144.32, 142.4, 136.1, 129.84, 124.9, 123.9, 122.4, 120.30, 115.63, 61.03, 53.40, 49.86, 42.63, 30.87, 30.11, 28.65, 27.07, 22.13, 15.9, 13.00. HRMS (ESI) calcd for: $C_{24}H_{37}N40$ [M+H]$^+$ 397.2967, found 397.2962.

Example 28: Preparation Method of Compound N50

Compound N46 (17.06 mg, 0.05 mmol) was dissolved in 1 mL of dry dichloromethane and cooled to 0° C. Acetyl chloride (4.24 μL, 0.06 mmol) was slowly added dropwise, and then triethylamine (13.86 μL, 0.1 mmol) was added dropwise. After the addition was completed, the reaction liquid was heated to room temperature and stirred for 0.5 h. After the reaction was completed, excessive water was added in an ice bath to quench the reaction. The reaction liquid was extracted with dichloromethane. The organic phases were combined, dried over anhydrous sodium sulfate, concentrated under reduced pressure, and purified by silica gel column chromatography (DCM:MeOH=10:1) to obtain compound N50, the reaction formula being as follows:

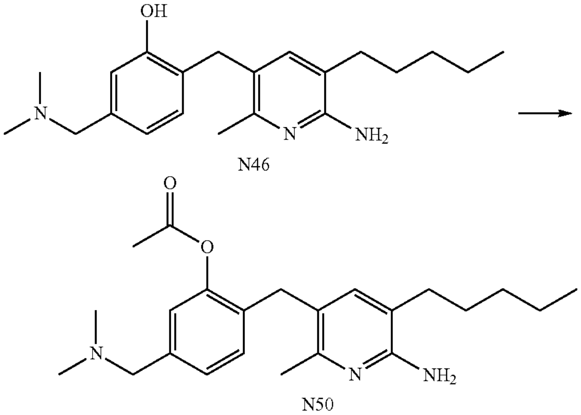

N46 N50

$^1$H NMR (400 MHz, Chloroform-d) δ 7.08 (dd, J=7.8, 1.7 Hz, 1H), 7.06 (d, J=1.6 Hz, 1H), 6.98 (s, 1H), 6.90 (d, J=7.8 Hz, 1H), 4.56 (s, 2H), 3.74 (s, 2H), 3.43 (s, 2H), 2.38 (t, J=7.7 Hz, 2H), 2.29 (s, 3H), 2.28 (s, 3H), 2.26 (s, 6H), 1.57 (m, 2H), 1.33 (m, 4H), 0.90 (t, J=6.8 Hz, 3H). $^{13}$C NMR (101 MHz, Chloroform-d) δ 169.23, 154.39, 151.49, 148.88, 139.43, 138.25, 130.99, 129.64, 126.79, 122.78, 122.43, 118.83, 63.50, 45.26, 31.65, 31.63, 30.39, 27.66, 22.49, 21.02, 20.87, 14.02. HRMS (ESI) calcd for: $C_{23}H_{34}N_3O_2$ $[M+H]^+$ 384.2651, found 384.2649.

Example 29: Preparation Method of Compounds N51-N53

Compounds N51-N53 were obtained by replacing compound N46 with N47, N48 or N49 according to the synthesis method of compound N50 in Example 28:

N51

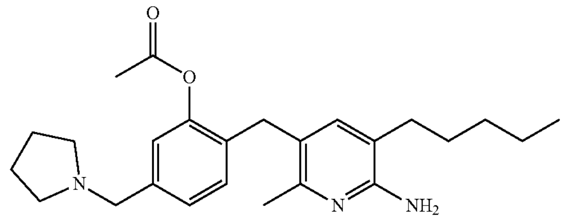

m/z:$[M+H]^+$ 410.4.

N52

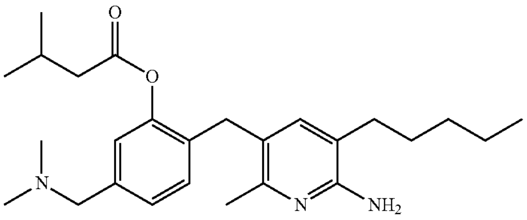

$^1$H NMR (400 MHz, Chloroform-d) δ 7.08 (dd, J=7.8, 1.7 Hz, 1H), 7.05 (d, J=1.3 Hz, 1H), 6.99 (s, 1H), 6.88 (d, J=7.8 Hz, 1H), 4.66 (s, 2H), 3.73 (s, 2H), 3.44 (s, 2H), 2.44 (d, J=7.1 Hz, 2H), 2.40-2.36 (t, J=7.8 Hz, 2H), 2.30 (s, 3H), 2.27 (s, 6H), 2.23 (m, 1H), 1.57 (m, 2H), 1.34 (m, 4H), 1.07 (s, 3H), 1.05 (s, 3H), 0.91 (t, J=6.8 Hz, 3H). $^{13}$C NMR (101 MHz, Chloroform-d) δ 171.33, 154.37, 151.40, 148.92, 139.48, 138.16, 130.95, 129.59, 126.74, 122.83, 122.47, 118.86, 63.53, 60.41, 45.24, 43.22, 31.63, 31.60, 30.37, 27.66, 25.74, 22.49, 20.91, 14.02.HRMS (ESI) calcd for: $C_{26}H_{39}N_3O_2$ $[M+H]^+$ 426.3121, found 426.3117.

N53

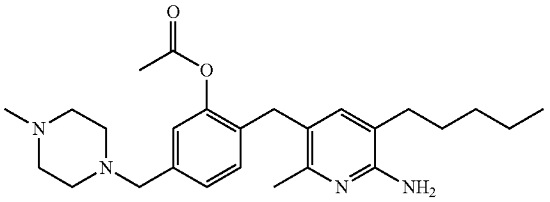

$^1$H NMR (400 MHz, Chloroform-d) δ 7.10-7.02 (m, 3H), 6.87 (d, J=7.8 Hz, 1H), 5.00 (s, 2H), 3.71 (s, 2H), 3.51 (s, 2H), 2.60 (m, 8H), 2.41 (s, 3H), 2.39 (t, J=7.6 Hz, 2H), 2.32 (s, 3H), 2.29 (s, 3H), 1.56 (m, 2H), 1.32 (m, 4H), 0.89 (t, J=6.8 Hz, 3H). $^{13}$C NMR (101 MHz, Chloroform-d) δ 169.3, 154.32, 150.86, 148.86, 139.76, 137.76, 130.85, 129.57, 126.85, 122.76, 122.27, 119.11, 62.06, 54.85, 52.53, 45.63, 31.60, 31.54, 30.29, 27.60, 22.48, 20.90, 20.63, 14.02. HRMS (ESI) calcd for: $C_{26}H_{39}N_4O_2$ $[M+H]^+$ 439.3073, found 439.3066.

Example 30: Preparation Method of Compound N54, Including the Steps as Follows (1) Under nitrogen atmosphere, compound 9 (900.11 mg, 3.5 mmol) was dissolved in 6 mL of a mixed solvent (DMF:DIEA=2:1), and methyl 4-ethynylbenzoate (320.10 mg, 7 mmol), tetrakis(triphenylphosphine)palladium (404.60 mg, 0.35 mmol), and cuprous iodide (76.30 mg, 0.7 mmol) were added in sequence. The reaction liquid was stirred at room temperature overnight. After the reaction was completed, the reaction liquid was filtered, concentrated under reduced pressure, and purified by silica gel column chromatography (PE:EA=2:1) to obtain compound 27, the reaction formula being as follows:

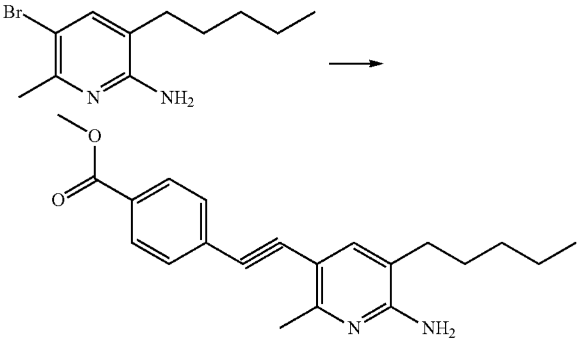

27

(2) Compound 27 (672.36 mg, 2 mmol) was dissolved in 10 mL of methanol, and 10% palladium/carbon (2128.4 mg, 2 mmol) was added. The reaction liquid was stirred in a hydrogen reactor under a pressure of 0.4 mPa overnight. After the reaction was completed, the reaction liquid was filtered, concentrated under reduced pressure, and purified by silica gel column chromatography (DCM:MeOH=20:1) to obtain compound 28, the reaction formula being as follows:

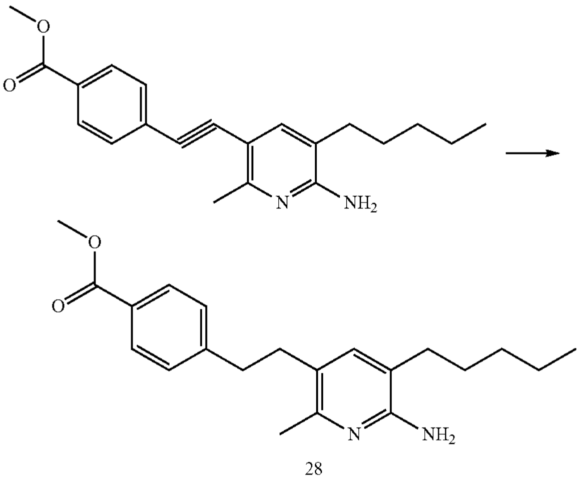

28

(3) Compound 28 (510.32 mg, 1.5 mmol) was dissolved in 10 mL of dry tetrahydrofuran and cooled to 0° C. Lithium aluminum hydride (114.0 mg, 3.0 mmol) was slowly added in batches. The mixture was successively stirred at 0° C. for 1.0 h. After the reaction was completed, 114 μL of water, 114 μL of 10% aqueous NaOH solution, and 342 μL of water were added to the reaction liquid in sequence to quench the reaction. Sonication was performed for 10 min, and then the reaction liquid was filtered. The filter residue was washed with acetone, and the filtrate was dried over anhydrous sodium sulfate, concentrated under reduced pressure, and purified by silica gel column chromatography (DCM: MeOH—15:1) to obtain compound 29, the reaction formula being as follows:

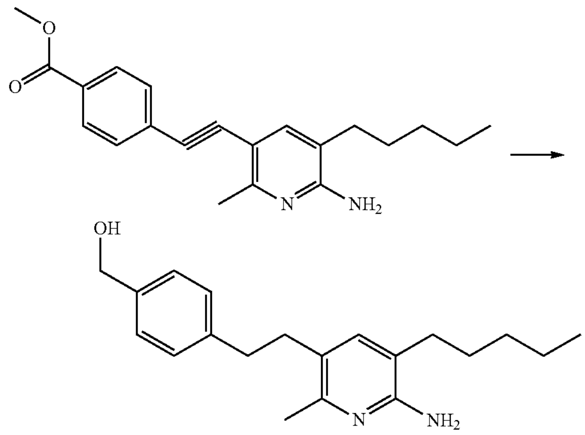

29

(4) Compound 29 (312.22 mg, 1 mmol) was dissolved in 5 mL of dry dichloromethane, and thionyl chloride (108.9 μL, 1.5 mmol) was slowly added dropwise. The reaction liquid was stirred at room temperature for 0.5 h. After the reaction was completed, the reaction liquid was concentrated under reduced pressure and dried to obtain a yellow solid 30, which was used directly without purification, the reaction formula being as follows:

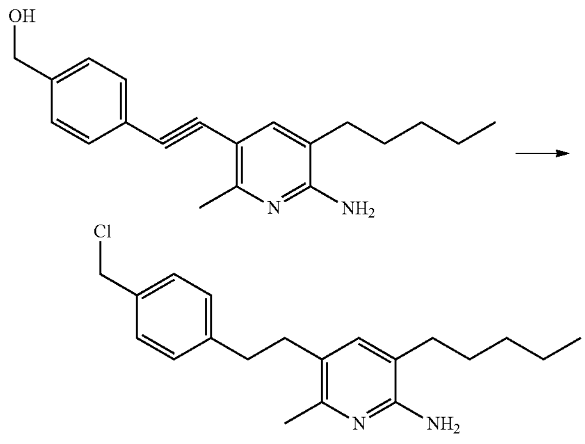

30

(5) Preparation method of compound N54: compound 30 (99.06 mg, 0.3 mmol) was dissolved in 5 mL of dry methanol. Dimethylamine (0.450 mL, 2 M in methanol) and potassium carbonate (82.93 mg, 0.6 mmol) were added in sequence. The reaction liquid was stirred at 45° C. for 3 h. After the reaction was completed, the reaction liquid was filtered, and the filtrate was dried over anhydrous sodium sulfate, concentrated under reduced pressure, and purified by silica gel column chromatography (DCM:MeOH=10:1) to obtain a white solid N54, the reaction formula being as follows:

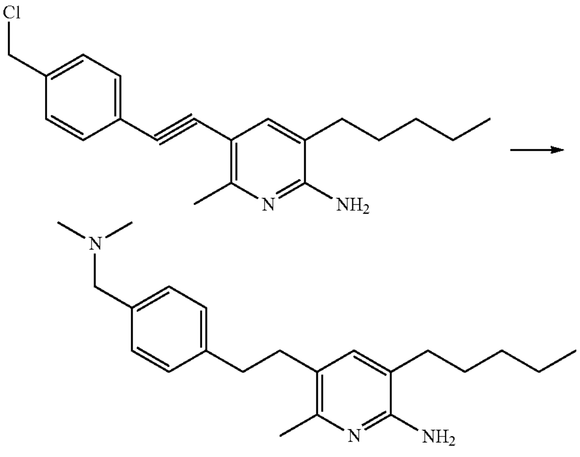

N54

$^1$H NMR (400 MHz, Chloroform-d) δ 7.29 (d, J=7.8 Hz, 2H), 7.11 (d, J=7.8 Hz, 2H), 7.06 (s, 1H), 5.52 (s, 2H), 3.58 (s, 2H), 2.79 (tt, J=7.9, 3.9 Hz, 4H), 2.39 (t, J=7.7 Hz, 2H), 2.36 (s, 6H), 2.34 (s, 3H), 1.56 (dd, J=14.3, 6.9 Hz, 2H), 1.35 (m, 4H), 0.92 (t, J=6.7 Hz, 3H). $^{13}$C NMR (101 MHz, Chloroform-d) δ 153.31, 147.41, 143.3, 140.50, 134.4, 129.72, 128.66, 124.25, 120.15, 63.29, 44.53, 36.36, 33.27, 31.54, 29.93, 27.54, 22.47, 18.93, 14.00. HRMS (ESI) calcd for: $C_{22}H_{34}N_3$ $[M+H]^+$ 340.2753, found 340.2756.

Example 31: Preparation Method of Compound 13a, Including the Steps as Follows Compound 13a was prepared from 5-bromo-$N_3$-butylpyridine-2,3-diamine as a raw material according to the preparation method of compound 12a in Example 5.

13a

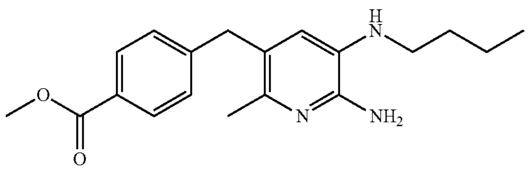

$^1$H NMR (400 MHz, Chloroform-d) δ 7.95 (d, J=8.2 Hz, 2H), 7.17 (d, J=8.2 Hz, 2H), 6.85 (s, 2H), 6.52 (s, 1H), 4.81 (t, J=5.2 Hz, 1H), 3.90 (s, 3H), 387 (s, 2H), 3.00 (td, J=7.2, 5.0 Hz, 2H), 2.42 (s, 3H), 1.64 (q, J=7.3 Hz, 2H), 1.35 (h, J=7.3 Hz, 2H), 0.86 (t, J=7.4 Hz, 3H). $^{13}$C NMR (101 MHz, Chloroform-d) δ 166.85, 144.40, 144.01, 132.01, 130.04, 129.40, 128.57, 128.44, 123.00, 119.52, 52.14, 43.75, 36.79, 30.29, 20.39, 16.38, 13.82.

Example 32: Preparation Method of Compound 15a, Including the Steps as Follows The compound was obtained using compound 13a as a raw material according to the synthesis method of compound 14a in Example 7:

15a

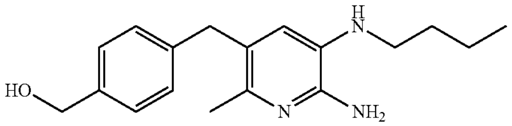

(4-((6-amino-5-(butylamino)-2-methylpyridin-3-yl)methyl)phenyl)methanol $^{1}$H NMR (400 MHz, Chloroform-d) δ 7.29 (d, J=7.9 Hz, 2H), 7.10 (d, J=7.8 Hz, 2H), 6.61 (s, 1H), 4.68 (s, 4H), 3.87 (s, 2H), 3.36 (s, 1H), 3.02 (t, J=7.2 Hz, 2H), 2.26 (s, 3H), 1.66-1.60 (m, 2H), 1.48-1.39 (m, 4H), 0.96 (t, J=7.3 Hz, 3H).

Example 33: Compounds N55-N60 were Obtained According to the Synthesis Method of Compound N4 in Example 10

N55

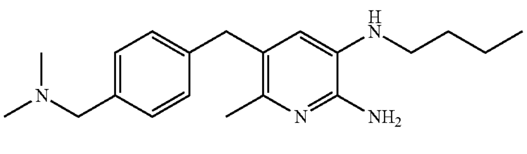

$^{1}$H NMR (400 MHz, Chloroform-d) δ 7.19 (d, J=7.9 Hz, 2H), 7.05 (d, J=7.8 Hz, 2H), 6.56 (s, 1H), 4.42 (s, 2H), 3.84 (s, 2H), 3.37 (s, 2H), 3.20 (s, 1H), 2.97 (t, J=7.2 Hz, 2H), 2.26 (s, 3H), 2.21 (s, 6H), 1.57 (dtd, J=8.7, 7.4, 5.9 Hz, 2H), 1.40 (dt, J=14.9, 7.4 Hz, 2H), 0.91 (t, J=7.3 Hz, 3H). $^{13}$C NMR (101 MHz, Chloroform-d) δ 146.50, 141.78, 139.38, 136.39, 130.39, 129.20, 128.33, 124.96, 120.26, 64.05, 45.31, 43.88, 37.92, 31.52, 20.56, 20.36, 13.93.

N56

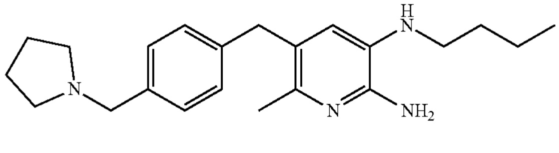

$^{1}$H NMR (400 MHz, Chloroform-d) δ 7.26 (d, J=7.8 Hz, 2H), 7.08 (d, J=7.8 Hz, 2H), 6.60 (s, 1H), 4.25 (s, 2H), 3.88 (s, 2H), 3.63 (s, 2H), 3.08 (s, 1H), 3.01 (t, J=7.1 Hz, 2H), 2.57-2.52 (m, 4H), 2.29 (s, 3H), 1.81 (p, J=3.1 Hz, 4H), 1.65-1.58 (m, 2H), 1.43 (q, J=7.4 Hz, 2H), 0.96 (t, J=7.3 Hz, 3H). $^{13}$C NMR (101 MHz, Chloroform-d) δ 146.50, 142.27, 139.43, 136.35, 130.37, 129.10, 128.36, 125.08, 120.43, 60.27, 54.07, 43.92, 37.95, 31.60, 23.40, 20.71, 20.37, 13.94.

N57

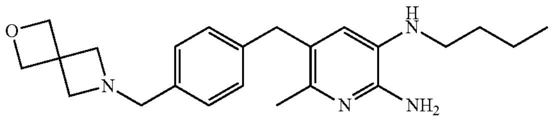

$^{1}$H NMR (400 MHz, Chloroform-d) δ 7.13 (d, J=8.1 Hz, 2H), 7.05 (d, J=8.0 Hz, 2H), 6.58 (s, 1H), 4.72 (s, 4H), 4.35 (s, 2H), 3.84 (s, 2H), 3.49 (s, 2H), 3.35 (s, 4H), 3.16 (s, 1H), 2.99 (t, J=7.3 Hz, 2H), 2.26 (s, 3H), 1.59 (q, J=7.2 Hz, 2H), 1.41 (h, J=7.3 Hz, 2H), 0.94 (t, J=7.3 Hz, 3H). $^{13}$C NMR (101 MHz, Chloroform-d) δ 146.51, 141.83, 139.52, 135.37, 130.40, 128.51, 128.44, 124.87, 120.34, 81.39, 63.66, 63.24, 43.90, 39.06, 37.90, 31.55, 20.54, 20.37, 13.93.

N58

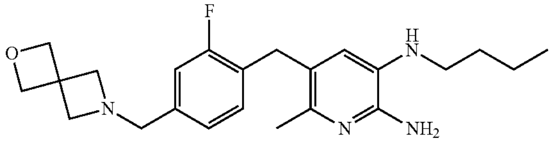

$^{1}$H NMR (400 MHz, Chloroform-d) δ 6.99-6.85 (m, 3H), 6.59 (s, 1H), 4.73 (s, 4H), 4.43 (s, 2H), 3.84 (s, 2H), 3.48 (s, 2H), 3.35 (s, 4H), 3.19 (s, 1H), 3.00 (t, J=7.4 Hz, 2H), 2.28 (s, 3H), 1.61 (q, J=7.0 Hz, 2H), 1.42 (h, J=7.3 Hz, 2H), 0.94 (t, J=7.3 Hz, 3H). $^{13}$C NMR (101 MHz, Chloroform-d) δ160.9 (J=243.0 Hz), 146.6, 141.5, 138.2 (J=7.2 Hz), 130.5, 130.1(J=4.9 Hz),126.2 (J=16.0 Hz),123.8 (J=3.1 Hz), 123.5, 120.3, 115.0 (J=22.3 Hz), 81.34, 63.74, 62.74, 43.88, 39.11, 31.50, 30.80 (J=3.0 Hz), 20.37, 20.27, 13.93. $^{19}$F NMR (376 MHz, Chloroform-d) δ-117.78.

BIOLOGICAL TEST EXAMPLES

Example 1: $EC_{50}$ Assay for Small Molecule Agonists

Reagents used for cell culture and detection for HEK-Blue™ hTLR7, HEK-Blue™ hTLR8 and control HEK-Blue Null2k were as follows: DMEM (4.5 g/L glucose), bovine serum FBS, streptomycin (50 μg/mL), penicillin (50 U/mL), Blasticidin (10 mg/mL), Zeocin™ (10 mg/mL), Normocin (50 mg/mL), and HEK-Blue™ Detection. Basal medium was as follows: DMEM+10% FBS+streptomycin+penicillin+Normocin (100 μg/mE); selective medium for resistance genes was as follows: DMEM+10% FBS+streptomycin+penicillin+Normocin (100 μg/mL)+Blasticidin (100 μg/mL)+Zeocin™ (100 g/mL).

Cell preparation: HEK-Blue™ hTLR7 and HEK-Blue™ hTLR8 cell lines were purchased from Invivogen. The cells frozen in liquid nitrogen were taken, quickly placed in a water bath at 37° C., shaken occasionally, and completely melted within 1 min. The cells were transferred to 15 mL of pre-heated basal medium and resuspended; centrifuged at 1,000 r/min for 5 min, supernatant discarded; resuspended with 1 mL of basal medium, transferred to a T25 culture flask, supplemented to 5 mL with the medium, and incubated in an incubator at 37° C.; after stable passage twice, and subjected to selective antibiotic screening: HEK-Blue™ hTLR7 or HEK-Blue™ hTLR8: 100 μg/mL Zeocin+Blasticidin (30 μg/mL), HEK-Blue Null2-k: 100 μg/mL Zeocin.

The fluid was changed 3 times a week. When the number of cells reached 70%-80%, PBS was added, and the cells were exfoliated by gently pipetting.

Activity assay steps: (1) adding a test sample to a 96-well plate at 20 μL/well (triplicate wells were set); (2) adding 20 μL of positive control (e.g., R848), and adding 20 μL of negative control (e.g., $ddH_2O$); (3) removing a T75 culture flask from the incubator, discarding the medium, adding 5-10 mL of pre-heated PBS, and gently pipetting the cells; adding 2-5 mL of PBS to the culture flask, incubating the culture flask in the incubator for 1-2 min, and then gently pipetting the cells to make them exfoliated; (4) mixing the mixture well, and counting the cells, without centrifugation; resuspending the cells with HEK-Blue™ assay solution and adjusting the cell number, taking care not to incubate for a long time to avoid too deep background or false positive. HEK-Blue hTLR cell number was about $2.2\times10^5$/mL, 180 μL/well (about 40000 cells), and HEK-Blue Null2-k cell number was about $2.8\times10^5$/mL, 180 μL/well (about 50000 cells). (5) incubating the cells in the incubator at 37° C. for 6-16 h, and detecting at 620-655 nm for SEAP readings.

Effect %=(mean OD of the administration group—mean OD of the $H_2O$ group at each concentration)/(mean $OD_{max}$ of the positive drug group—mean OD of the $H_2O$ group)×100. $EC_{50}$ was calculated by fitting Lg [concentration]-effect curves using GraphPad Prism5 software.

Experimental results: the concentration for 50% of maximal effect ($EC_{50}$) refers to a corresponding concentration of small molecules that can cause 50% of the maximal agonistic effect. The experimental results show that the concentration for 50% of maximal effect of the positive control VTX2337 was HLR8 (102 nM), whereas that of compound N55 of the present invention was hTLR8 (15 nM), and that of compound N9 was HLR8 (40 nM). $EC_{50}$ represents a potency for agonizing the TLR8 receptor, with smaller values indicating better efficacy. The TLR8 agonists included in the present invention have no detected agonist activity to the HTLR7 cell line at a concentration of 25 μM (nd represents that $EC_{50}$ is larger than 25 M), and thus these TLR8 agonists are specific. In the following table, the unit of the agonist activity is nanomole, unless otherwise specified.

TABLE 1

| Test results | | |
|---|---|---|
| Compound No. | hTLR7($EC_{50}$) | hTLR8($EC_{50}$) |
| VTX2337 (Positive control) | >3000 nM | 102 nM |
| N1 | nd | 398 nM |
| N2 | nd | 480 nM |
| N3 | nd | 1582 nM |
| N4 | nd | 58 nM |
| N5 | nd | 122 nM |
| N6 | nd | 84 nM |
| N7 | nd | 63 nM |
| N8 | nd | 428 nM |
| N9 | nd | 54 nM |
| N10 | nd | 134 nM |
| N11 | nd | 151 nM |
| N12 | nd | 109 nM |
| N13 | nd | 3000 nM |
| N14 | nd | >4000 nM |
| N15 | nd | 628 nM |
| N16 | nd | >4000 nM |
| N17 | nd | 121 nM |
| N18 | nd | 124 nM |
| N19 | nd | 104 nM |

TABLE 1-continued

| Test results | | |
|---|---|---|
| Compound No. | hTLR7($EC_{50}$) | hTLR8($EC_{50}$) |
| N20 | nd | 130 nM |
| N21 | nd | 117 nM |
| N22 | nd | 81 nM |
| N23 | nd | 80 nM |
| N24 | nd | 113 nM |
| N25 | nd | >4000 nM |
| N26 | nd | >4000 nM |
| N27 | nd | >4000 nM |
| N28 | nd | >4000 nM |
| N29 | nd | >4000 nM |
| N30 | nd | >4000 nM |
| N31 | nd | 248 nM |
| N32 | nd | 290 nM |
| N33 | nd | >4000 nM |
| N34 | nd | >4000 nM |
| N35 | nd | >4000 nM |
| N36 | nd | >4000 nM |
| N37 | nd | >4000 nM |
| N38 | nd | >4000 nM |
| N39 | nd | >4000 nM |
| N40 | nd | >4000 nM |
| N41 | nd | >4000 nM |
| N42 | nd | 87 nM |
| N43 | nd | 102 nM |
| N44 | nd | 1125 nM |
| N45 | nd | 166 nM |
| N46 | nd | 351 nM |
| N47 | nd | 473 nM |
| N48 | nd | >4000 nM |
| N49 | nd | 627 nM |
| N50 | nd | 105 nM |
| N51 | nd | 175 nM |
| N52 | nd | 252 nM |
| N53 | nd | 273 nM |
| N54 | nd | 518 nM |
| N55 | nd | 15 nM |
| N56 | nd | 28 nM |
| N57 | nd | 16 nM |
| N58 | nd | 40 nM |

The above description is only for the purpose of illustrating the preferred examples of the present invention, and is not intended to limit the scope of the present invention. Any modifications, equivalents, and the like made without departing from the spirit and principle of the present invention shall fall in the protection scope of the present invention.

The foregoing examples and methods described herein may vary based on the abilities, experience, and preferences of those skilled in the art.

The certain order in which the steps of the method are listed in the present invention does not constitute any limitation on the order of the steps of the method.

The invention claimed is:

1. A compound of the formula (I):

(I)

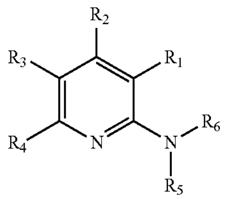

or a pharmaceutically acceptable salt thereof, wherein:

$R_1$ is $C_1$-$C_{12}$ alkyl, $C_1$-$C_{12}$ alkylene-cycloalkyl, $C_1$-$C_{12}$ alkylene-aryl, $C_1$-$C_{12}$ alkylene-heterocyclyl, $C_2$-$C_{12}$ alkenyl, or $NHC_1$-$C_{12}$ alkyl;

wherein the $C_1$-$C_{12}$ alkyl or $C_1$-$C_{12}$ alkylene is optionally substituted with one or more substituents independently selected from the group consisting of halogen, CN, $NO_2$, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', and $S(O)_2R'$;

wherein the $C_2$-$C_{12}$ alkenyl is optionally substituted with one or more substituents independently selected from the group consisting of halogen, CN, $NO_2$, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', $S(O)_2R'$, $C_3$-$C_{10}$ cycloalkyl, aryl, and heterocyclyl; and wherein the cycloalkyl, aryl, or heterocyclyl of $C_1$-$C_{12}$ alkylene-cycloalkyl, $C_1$-$C_{12}$ alkylene-aryl, or $C_1$-$C_{12}$ alkylene-heterocyclyl is optionally substituted with one or more substituents independently selected from the group consisting of halogen, CN, $NO_2$, $C_1$-$C_{12}$ alkyl, $C_2$-$C_{12}$ alkenyl, $C_2$-$C_{12}$ alkynyl, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', $S(O)_2R'$, $C_3$-$C_{10}$ cycloalkyl, aryl, and heterocyclyl;

$R_2$ is H;

$R_3$ is $C_1$-$C_{12}$ alkylene-aryl;

wherein the $C_1$-$C_{12}$ alkylene is optionally substituted with one or more substituents independently selected from the group consisting of halogen, CN, $NO_2$, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', and $S(O)_2R'$; and wherein the aryl of $C_1$-$C_{12}$ alkylene-aryl is substituted with one or more substituents independently selected from the group consisting of halogen, CN, $NO_2$, $C_1$-$C_{12}$ alkyl, $C_2$-$C_{12}$ alkenyl, $C_2$-$C_{12}$ alkynyl, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', $S(O)_2R'$, $C_3$-$C_{10}$ cycloalkyl, aryl, and heterocyclyl;

$R_4$ is $C_1$-$C_{12}$ alkyl, $C_1$-$C_{12}$ alkylene-cycloalkyl, $C_1$-$C_{12}$ alkylene-aryl, $C_1$-$C_{12}$ alkylene-heterocyclyl, or $C_2$-$C_{12}$ alkenyl;

wherein the $C_1$-$C_{12}$ alkyl or $C_1$-$C_{12}$ alkylene is optionally substituted with one or more substituents independently selected from the group consisting of halogen, CN, $NO_2$, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', and $S(O)_2R'$;

wherein the $C_2$-$C_{12}$ alkenyl is optionally substituted with one or more substituents independently selected from the group consisting of halogen, CN, $NO_2$, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', $S(O)_2R'$, $C_3$-$C_{10}$ cycloalkyl, aryl, and heterocyclyl; and wherein the cycloalkyl, aryl, or heterocyclyl of $C_1$-$C_{12}$ alkylene-cycloalkyl, $C_1$-$C_{12}$ alkylene-aryl, or $C_1$-$C_{12}$ alkylene-heterocyclyl is optionally substituted with one or more substituents independently selected from the group consisting of halogen, CN, $NO_2$, $C_1$-$C_{12}$ alkyl, $C_2$-$C_{12}$ alkenyl, $C_2$-$C_{12}$ alkynyl, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', $S(O)_2R'$, $C_3$-$C_{10}$ cycloalkyl, aryl, and heterocyclyl;

$R_5$ is H;

$R_6$ is H; and each R' is independently H, halogen, CN, $NO_2$, $C_1$-$C_{12}$ alkyl, $C_2$-$C_{12}$ alkenyl, $C_2$-$C_{12}$ alkynyl, C(O)H, C(O)$C_1$-$C_{12}$ alkyl, C(O)OH, $NH_2$, OH, SH, $C_3$-$C_{10}$ cycloalkyl, aryl, or heterocyclyl.

2. The compound according to claim 1, or a pharmaceutically acceptable salt thereof, wherein $R_1$ is $NHC_1$-$C_{12}$ alkyl.

3. The compound according to claim 2, or a pharmaceutically acceptable salt thereof, wherein $R_1$ is $C_1$-$C_{12}$ alkyl, $C_1$-$C_{12}$ alkylene-cycloalkyl, $C_1$-$C_{12}$ alkylene-aryl, or $C_1$-$C_{12}$ alkylene-heterocyclyl;

wherein the $C_1$-$C_{12}$ alkyl or $C_1$-$C_{12}$ alkylene is optionally substituted with one or more substituents independently selected from the group consisting of halogen, CN, $NO_2$, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', and $S(O)_2R'$; and wherein the cycloalkyl, aryl, or heterocyclyl of $C_1$-$C_{12}$ alkylene-cycloalkyl, $C_1$-$C_{12}$ alkylene-aryl, or $C_1$-$C_{12}$ alkylene-heterocyclyl is optionally substituted with one or more substituents independently selected from the group consisting of halogen, CN, $NO_2$, $C_1$-$C_{12}$ alkyl, $C_2$-$C_{12}$ alkenyl, $C_2$-$C_{12}$ alkynyl, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', $S(O)_2R'$, $C_3$-$C_{10}$ cycloalkyl, aryl, and heterocyclyl.

4. The compound according to claim 1, or a pharmaceutically acceptable salt thereof, wherein $R_1$ is $CH_2CH_2CH_2OCH_3$, $CH_2CH_2CH_2CH_2CH_3$, or $NHCH_2CH_2CH_2CH_3$.

5. The compound according to claim 1, wherein the compound is of formula (III):

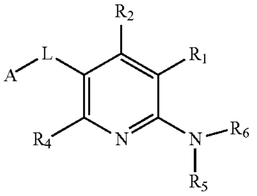

(III)

or a pharmaceutically acceptable salt thereof, wherein:

A is phenylene-$R_A$ or naphthalenylene-$R_A$;

each $R_A$ is independently H, halogen, CN, $NO_2$, $C_1$-$C_{12}$ alkyl, $C_2$-$C_{12}$ alkenyl, $C_2$-$C_{12}$ alkynyl, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', $S(O)_2R'$, $C_3$-$C_{10}$ cycloalkyl, aryl, or heterocyclyl;

L is $-(CH_2)_m-X-(CH_2)_n-$;

m is 0, 1, 2, 3, 4, or 5;

n is 0, 1, 2, 3, 4, 5, or 6;

X is $-CR_7R_8-$;

$R_7$ is H or $C_1$-$C_4$ alkyl; and $R_8$ is H or $C_1$-$C_4$ alkyl.

6. The compound according to claim 5, wherein the compound is of the following formula:

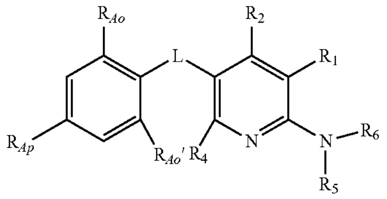

or a pharmaceutically acceptable salt thereof, wherein:

$R_{Ao}$ is H, halogen, CN, $NO_2$, $C_1$-$C_{12}$ alkyl, C(O)R', C(O)NHR', C(O)OR', NR'R', NHC(O)R', OR', OC(O)R', SR', S(O)R', $S(O)_2R'$, $C_3$-$C_{10}$ cycloalkyl, aryl, or heterocyclyl;

$R_{Ao'}$ is H, halogen, CN, $NO_2$, $C_1$-$C_{12}$ alkyl, C(O)R', C(O)NHR', C(O)OR', NR'R', NHC(O)R', OR', OC(O)R', SR', S(O)R', $S(O)_2R'$, $C_3$-$C_{10}$ cycloalkyl, aryl, or heterocyclyl; and $R_{Ap}$ is H, halogen, CN, $NO_2$, $C_1$-$C_{12}$ alkyl, C(O)R', C(O)NHR', C(O)OR', NR'R', NHC(O)R', OR', OC(O)R', SR', S(O)R', $S(O)_2R'$, $C_3$-$C_{10}$ cycloalkyl, aryl, or heterocyclyl.

7. The compound according to claim 6, or a pharmaceutically acceptable salt thereof, wherein:

$R_{Ao}$ is H, F, Cl, Br, C(O)R', C(O)OR', NR'R', OR', OC(O)R', azetidin-1-yl, pyrrolidin-1-yl, piperidin-1-yl, azepan-1-yl, piperazin-1-yl, morpholin-4-yl, or 2-oxa-6-azaspiro[3.3]heptan-6-yl;

$R_{Ao}'$ is H, F, Cl, Br, C(O)R', C(O)OR', NR'R', OR', OC(O)R', azetidin-1-yl, pyrrolidin-1-yl, piperidin-1-yl, azepan-1-yl, piperazin-1-yl, morpholin-4-yl, or 2-oxa-6-azaspiro[3.3]heptan-6-yl;

$R_{Ap}$ is H, F, Cl, Br, C(O)R', C(O)OR', NR'R', OR', OC(O)R', azetidin-1-yl, pyrrolidin-1-yl, piperidin-1-yl, azepan-1-yl, piperazin-1-yl, morpholin-4-yl, or 2-oxa-6-azaspiro[3.3]heptan-6-yl; and each R' is independently H, $C_1$-$C_{12}$ alkyl, or $C_3$-$C_{10}$ cycloalkyl.

8. The compound according to claim 7, or a pharmaceutically acceptable salt thereof, wherein:

$R_{Ao}$ is H, F, Cl, Br, C(O)OH, $C(O)OC_1$-$C_{10}$ alkyl, $NH_2$, NH $C_1$-$C_{10}$ alkyl, $NHC_3$-$C_{10}$ cycloalkyl, $N(C_1$-$C_{10}$ alkyl)($C_1$-$C_{10}$ alkyl), OH, $OC_1$-$C_{10}$ alkyl, azetidin-1-yl, pyrrolidin-1-yl, piperidin-1-yl, azepan-1-yl, piperazin-1-yl, morpholin-4-yl, or 2-oxa-6-azaspiro[3.3]heptan-6-yl;

$R_{Ao}'$ is H, F, Cl, Br, C(O)OH, $C(O)OC_1$-$C_{10}$ alkyl, $NH_2$, $NHC_1$-$C_{10}$ alkyl, $NHC_3$-$C_{10}$ cycloalkyl, $N(C_1$-$C_{10}$ alkyl)($C_1$-$C_{10}$ alkyl), OH, $OC_1$-$C_{10}$ alkyl, azetidin-1-yl, pyrrolidin-1-yl, piperidin-1-yl, azepan-1-yl, piperazin-1-yl, morpholin-4-yl, or 2-oxa-6-azaspiro[3.3]heptan-6-yl; and $R_{Ap}$ is H, F, Cl, Br, C(O)OH, $C(O)OC_1$-$C_{10}$ alkyl, $NH_2$, $NHC_1$-$C_{10}$ alkyl, $NHC_3$-$C_{10}$ cycloalkyl, $N(C_1$-$C_{10}$ alkyl)($C_1$-$C_{10}$ alkyl), OH, $OC_1$-$C_{10}$ alkyl, azetidin-1-yl, pyrrolidin-1-yl, piperidin-1-yl, azepan-1-yl, piperazin-1-yl, morpholin-4-yl, or 2-oxa-6-azaspiro[3.3]heptan-6-yl.

9. The compound according to claim 6, or a pharmaceutically acceptable salt thereof, wherein:

m is 0, 1, 2, or 3; and n is 0, 1, 2, or 3.

10. The compound according to claim 9, or a pharmaceutically acceptable salt thereof, wherein:

m is 0 or 1; and n is 0 or 1.

11. The compound according to claim 1, or a pharmaceutically acceptable salt thereof, wherein $R_4$ is $C_1$-$C_{10}$ alkyl, wherein the $C_1$-$C_{10}$ alkyl is optionally substituted with one or more substituents independently selected from the group consisting of halogen, CN, $NO_2$, C(O)R', C(O)NR'R', C(O)NR'OR', $C(O)NR'S(O)_2R'$, C(O)OR', NR'R', NR'C(NR')NR'R', NR'C(O)R', $NR'S(O)_2R'$, $N[C(O)R']_2$, =NR', $N_3$, OR', OC(O)R', OC(O)NR'R', OC(O)OR', =O, $OS(O)_2R'$, $OS(O)_3R'$, P(O)R'OR', P(O)NR'R'OR', P(O)OR'OR', SR', S(O)R', and $S(O)_2R'$.

12. The compound according to claim 1, or a pharmaceutically acceptable salt thereof, wherein $R_4$ is $C_1$-$C_6$ alkyl.

13. The compound according to claim 12, or a pharmaceutically acceptable salt thereof, wherein $R_4$ is $CH_3$.

14. A pharmaceutical composition comprising a pharmaceutically acceptable excipient and a compound according to claim 1, or a pharmaceutically acceptable salt thereof.

15. A method for enhancing (a) an anti-HIV effect; (b) a chemotherapeutic effect; or (c) an immune response in a subject, wherein the method comprises administering to the subject in need thereof a therapeutically effective amount of a compound according to claim 1, or a pharmaceutically acceptable salt thereof.

16. A method for inhibiting toll-like receptor 8 (TLR8) activity in a subject, wherein the method comprises administering to the subject in need thereof a therapeutically effective amount of a compound according to claim 1, or a pharmaceutically acceptable salt thereof.

17. The method according to claim 16, wherein the subject has a disease selected from the group consisting of a disease caused by a pathogen infection, a disease associated with a pathogen infection, an immunological disease, an inflammatory disease, and a tumor.
18. A compound selected from the group consisting of:
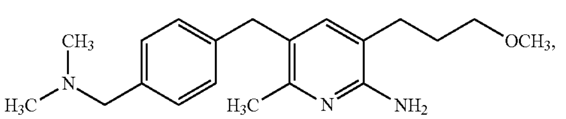
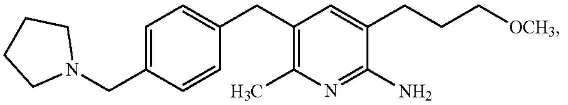
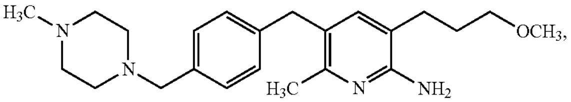
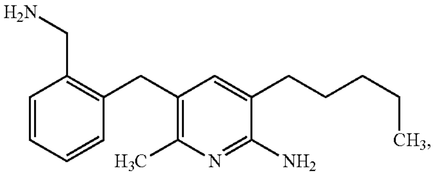
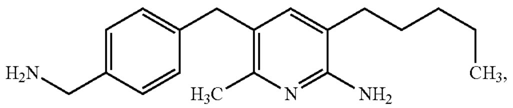
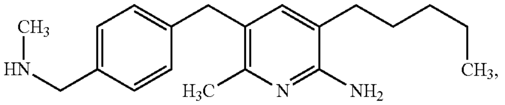
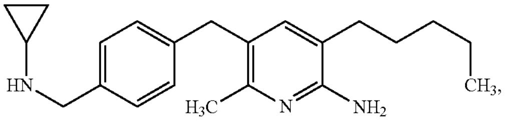
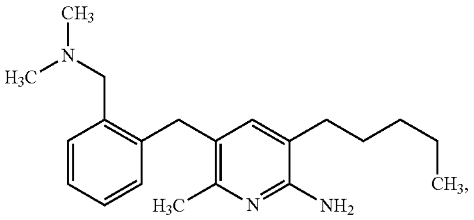
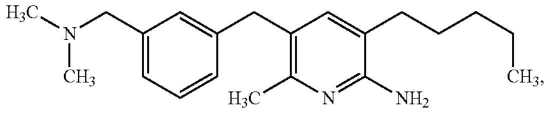
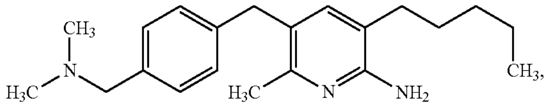
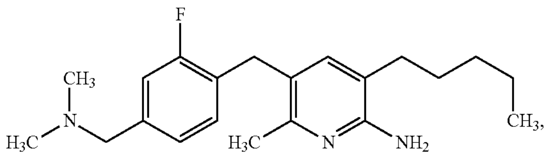
-continued
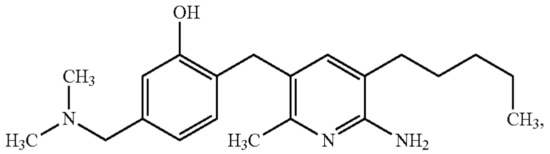
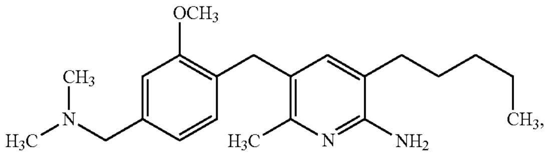
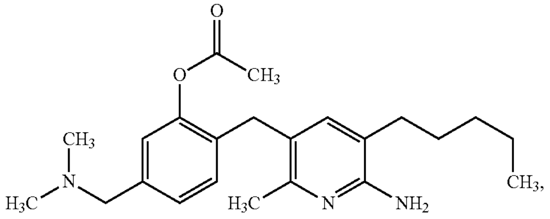
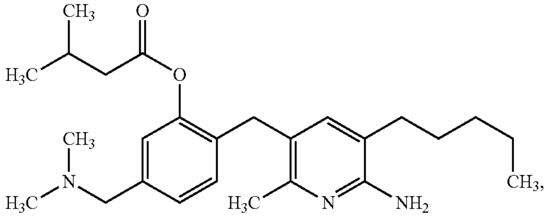
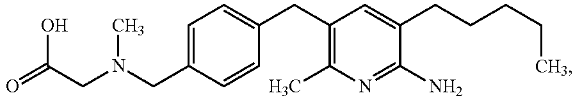
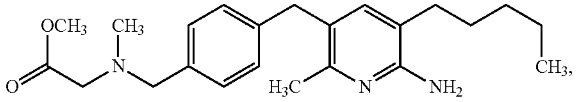
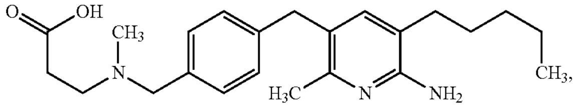
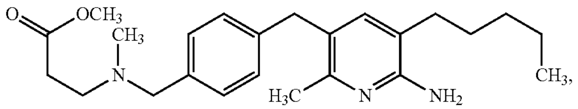
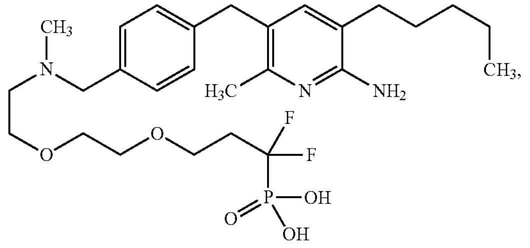
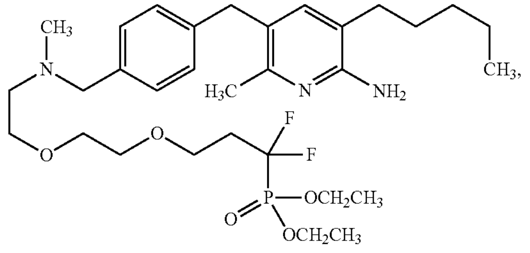

-continued
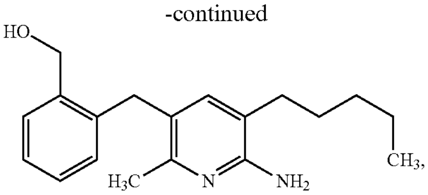
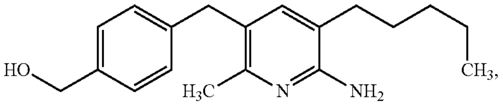
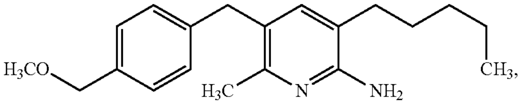
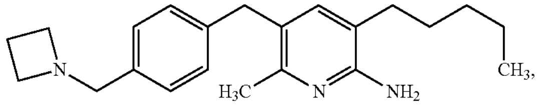
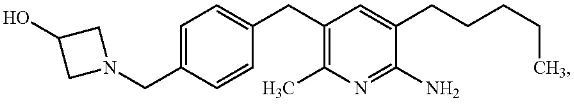
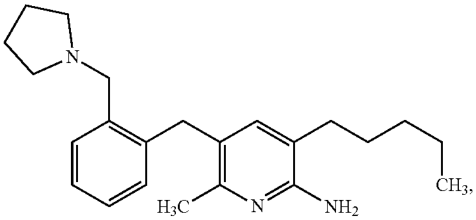
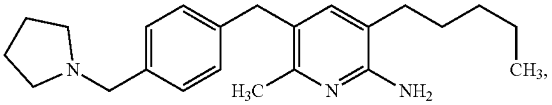
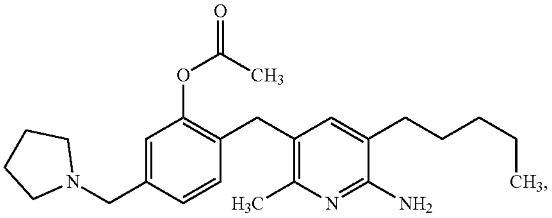
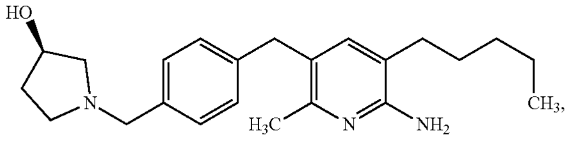
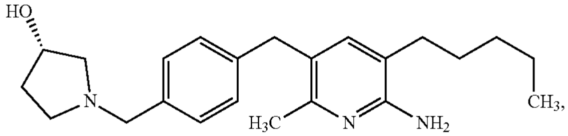
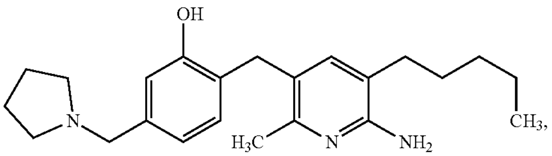
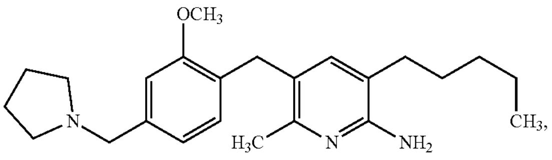
-continued
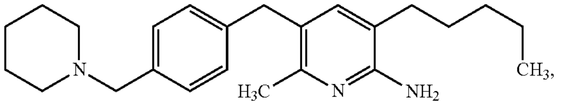
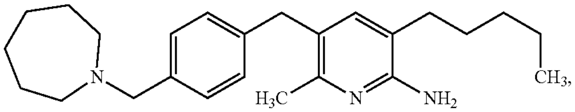
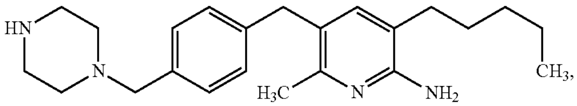
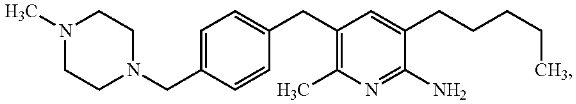
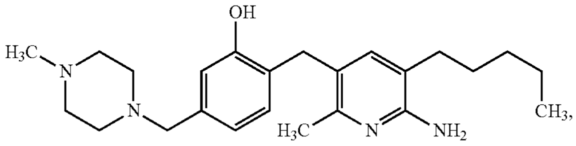
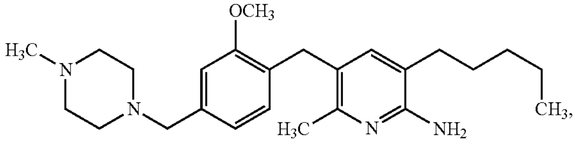
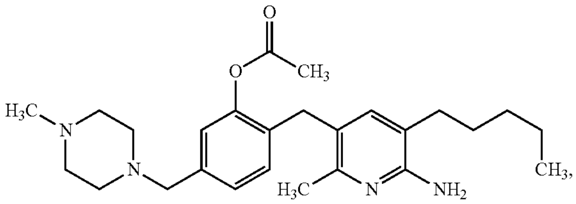
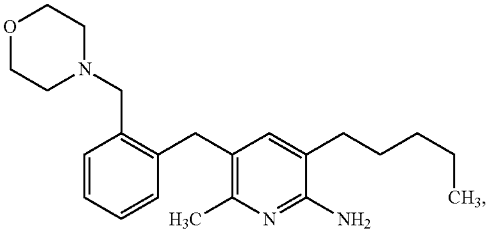
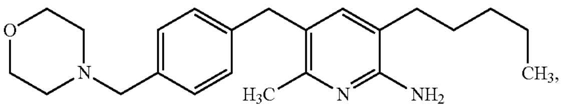
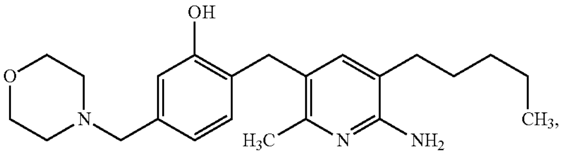
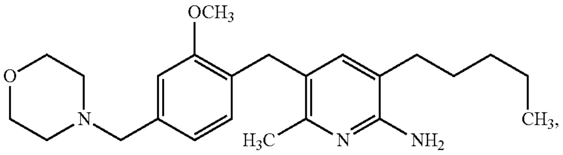
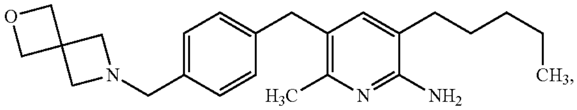

-continued
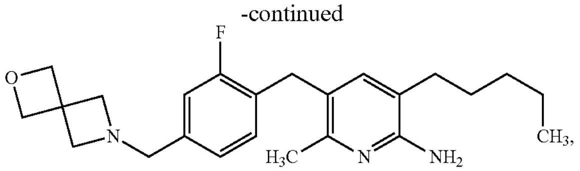
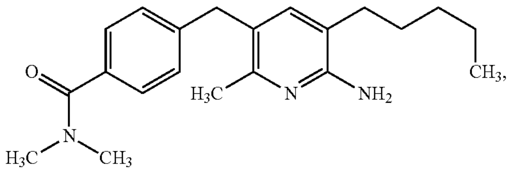
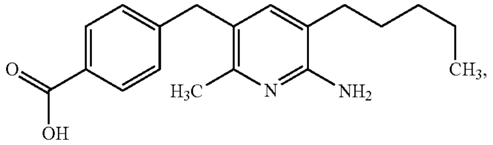
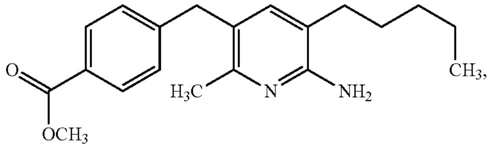
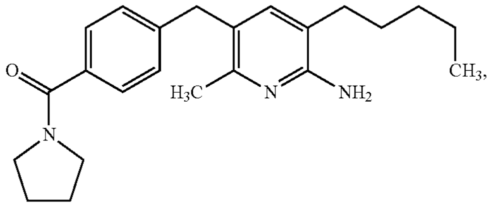
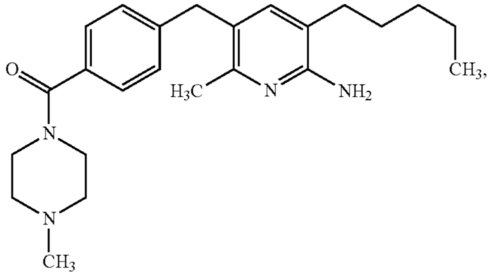
-continued
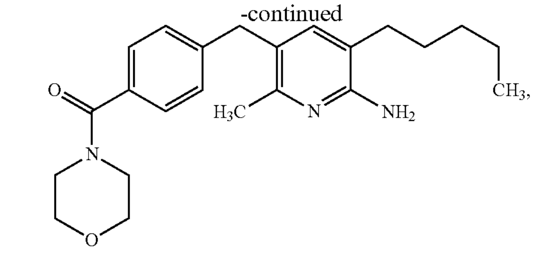
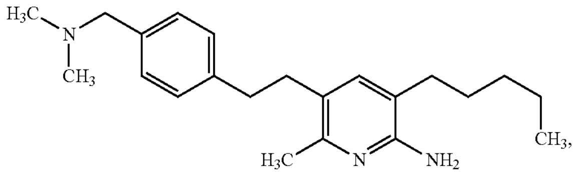
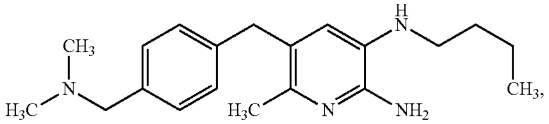
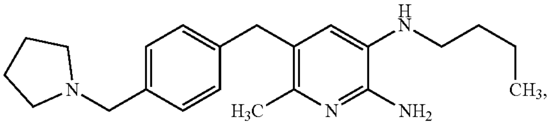
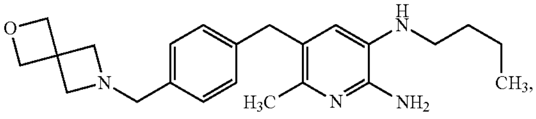
and
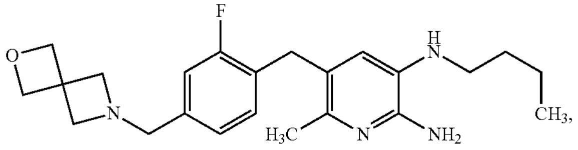
or a pharmaceutically acceptable salt thereof.
* * * * *